United States Patent
Iyer et al.

(10) Patent No.: US 12,283,381 B2
(45) Date of Patent: Apr. 22, 2025

(54) SYSTEMS AND METHODS FOR CONTINUOUS GLUCOSE MONITORING OUTCOME PREDICTIONS

(71) Applicant: Welldoc, Inc, Columbia, MD (US)

(72) Inventors: Anand K. Iyer, Potomac, MD (US); Abhimanyu Kumbara, Columbia, MD (US); Mansur E. Shomali, Columbia, MD (US); Junjie Luo, Columbia, MD (US); Guodong Gao, Clarksville, MD (US)

(73) Assignee: Welldoc, Inc., Columbia, MD (US)

( * ) Notice: Subject to any disclaimer, the term of this patent is extended or adjusted under 35 U.S.C. 154(b) by 0 days.

(21) Appl. No.: 18/891,466

(22) Filed: Sep. 20, 2024

(65) Prior Publication Data
US 2025/0014760 A1    Jan. 9, 2025

Related U.S. Application Data

(63) Continuation of application No. PCT/US2024/023736, filed on Apr. 9, 2024.
(Continued)

(51) Int. Cl.
*G16H 50/30*    (2018.01)
*G16H 10/60*    (2018.01)

(52) U.S. Cl.
CPC .............. *G16H 50/30* (2018.01); *G16H 10/60* (2018.01)

(58) Field of Classification Search
CPC ............................... G16H 10/60; G16H 50/30
(Continued)

(56) References Cited

U.S. PATENT DOCUMENTS

2003/0208113 A1* 11/2003 Mault ............... G16H 40/63
                                                    600/316
2018/0043096 A1*  2/2018 Dobbles ............ A61B 5/14532
(Continued)

FOREIGN PATENT DOCUMENTS

WO   WO-2009048462 A1 *  4/2009  ......... A61B 5/14532
WO        2013032965 A1    3/2013
(Continued)

OTHER PUBLICATIONS

Bertachi, Arthur; Prediction of Nocturnal Hypoglycemia in Adults with Type 1 Diabetes under Multiple Daily Injections Using Continuous Glucose Monitoring and Physical Activity Monitor; Sensors 20.6: 1705. MDPI AG. (2020) (Year: 2020).*
(Continued)

*Primary Examiner* — Hiep V Nguyen
(74) *Attorney, Agent, or Firm* — Bookoff McAndrews, PLLC

(57) ABSTRACT

Methods and devices include predicting future glucose and engagement levels for a user by receiving the user's glucose levels collected by a continuous glucose monitoring (CGM) device over a time period, receiving engagement data associated with the user, wherein the engagement data are associated with the user's medication intake, diet, physical activity, laboratory results, and education activity, determining a first glycemia risk index (GRI) value, determining, using a machine learning model and responsive to the user's glucose levels and the engagement data collected over the time period, one or more predictions for future glucose levels for the user including a prediction that a future GRI value is greater than or less than the first GRI value, and determining, using the machine learning model and responsive to the user's engagement data collected over the time period, one or more predictions for future engagement levels.

17 Claims, 47 Drawing Sheets

Related U.S. Application Data

(60) Provisional application No. 63/495,468, filed on Apr. 11, 2023.

(58) Field of Classification Search
USPC .................................................................. 705/2
See application file for complete search history.

(56) References Cited

U.S. PATENT DOCUMENTS

| | | | | |
|---|---|---|---|---|
| 2020/0176121 A1* | 6/2020 | Dalal | ................ | G16H 20/60 |
| 2021/0050085 A1* | 2/2021 | Hayter | ................ | G16H 10/60 |

FOREIGN PATENT DOCUMENTS

| | | | |
|---|---|---|---|
| WO | 2017192397 A8 | 9/2017 | |
| WO | 2017192397 A1 | 11/2017 | |
| WO | 2018175935 A1 | 9/2018 | |
| WO | 2022169856 A1 | 8/2022 | |

OTHER PUBLICATIONS

Pai, Amruta; A Computational Analysis of Meal Events Using Food Diaries and Continuous Glucose Monitors; : Rice University, ProQuest Dissertations & Theses, 2023. 31532958 (Year: 2023).*

Ramesh, Jayroop ; A remote healthcare monitoring framework for diabetes prediction using machine learning; Healthcare Technology Letters 8.3: 45-57. John Wiley & Sons, Inc. (Jun. 1, 2021) (Year: 2021).*

Klonoff et al., "A Glycemia Risk Index (GRI) of Hypoglycemia and Hyperglycemia for Continuous Glucose Monitoring Validated by Clinician Ratings", Journal of Diabetes Science and Technology. Mar. 29, 2022. doi:10.1177/19322968221085273.

Quinn et al., "Cluster-randomized trial of a mobile phone personalized behavioral intervention for blood glucose control", Diabetes Care. Sep. 2011;34(9):1934-42. doi: 10.2337/dc11-0366.

* cited by examiner

| QUESTION | OUTCOME VARIABLE TO OBSERVE | QUESTION # | SCENARIO |
|---|---|---|---|
| CAN WE USE EARLY STAGE DIGITAL HEALTH & CGM ENGAGEMENT TO PREDICT FUTURE TIR OUTCOMES? | TIR | 1 | 2-STATE DIRECTION PREDICTION: GETTING BETTER OR WORSE? |
| | TIR | 2 | 3-STATE DIRECTION PREDICTION: GETTING BETTER, REMAINING SAME, GETTING WORSE |
| | TIR | 3 | 2-STATE VALUE PREDICTION: PREDICTING IF THE FUTURE TIR VALUE WILL BE > OR < 70% (GOAL) |
| CAN WE USE EARLY STAGE DIGITAL HEALTH & CGM ENGAGEMENT TO PREDICT FUTURE TIR OUTCOMES? | GRI | 4 | 2-STATE DIRECTION PREDICTION: GETTING BETTER OR WORSE? |
| | GRI | 5 | 3-STATE DIRECTION PREDICTION: GETTING BETTER, REMAINING SAME, GETTING WORSE |
| | GRI | 6 | 2-STATE VALUE PREDICTION: PREDICTING IF THE FUTURE GRI VALUE WILL BE > OR < 40 (GOAL) |
| CAN WE USE EARLY STAGE DIGITAL HEALTH & CGM ENGAGEMENT TO PREDICT FUTURE DIGITAL HEALTH ENGAGEMENT? | MEDAL ENGAGEMENT | 7 | 2-STATE DIRECTION PREDICTION: IS FUTURE ENGAGEMENT HIGH OR LOW FOR EACH OF MEDICATIONS, EDUCATION, DIET, ACTIVITY, LABS? |
| | MANUAL ENTRY MEDAL ENGAGEMENT | 8 | 2-STATE DIRECTION PREDICTION: IS FUTURE ENGAGEMENT HIGH OR LOW FOR EACH OF MEDICATIONS, EDUCATION, DIET, LABS? |
| | CGM WEAR TIME | 9 | 2-STATE VALUE PREDICTION: IS FUTURE CGM WEAR > OR < 70% OF TIME (I.E., 70% OF THE TOTAL 2880 POSSIBLE READINGS IN A WEEK) |

FIG. 7B

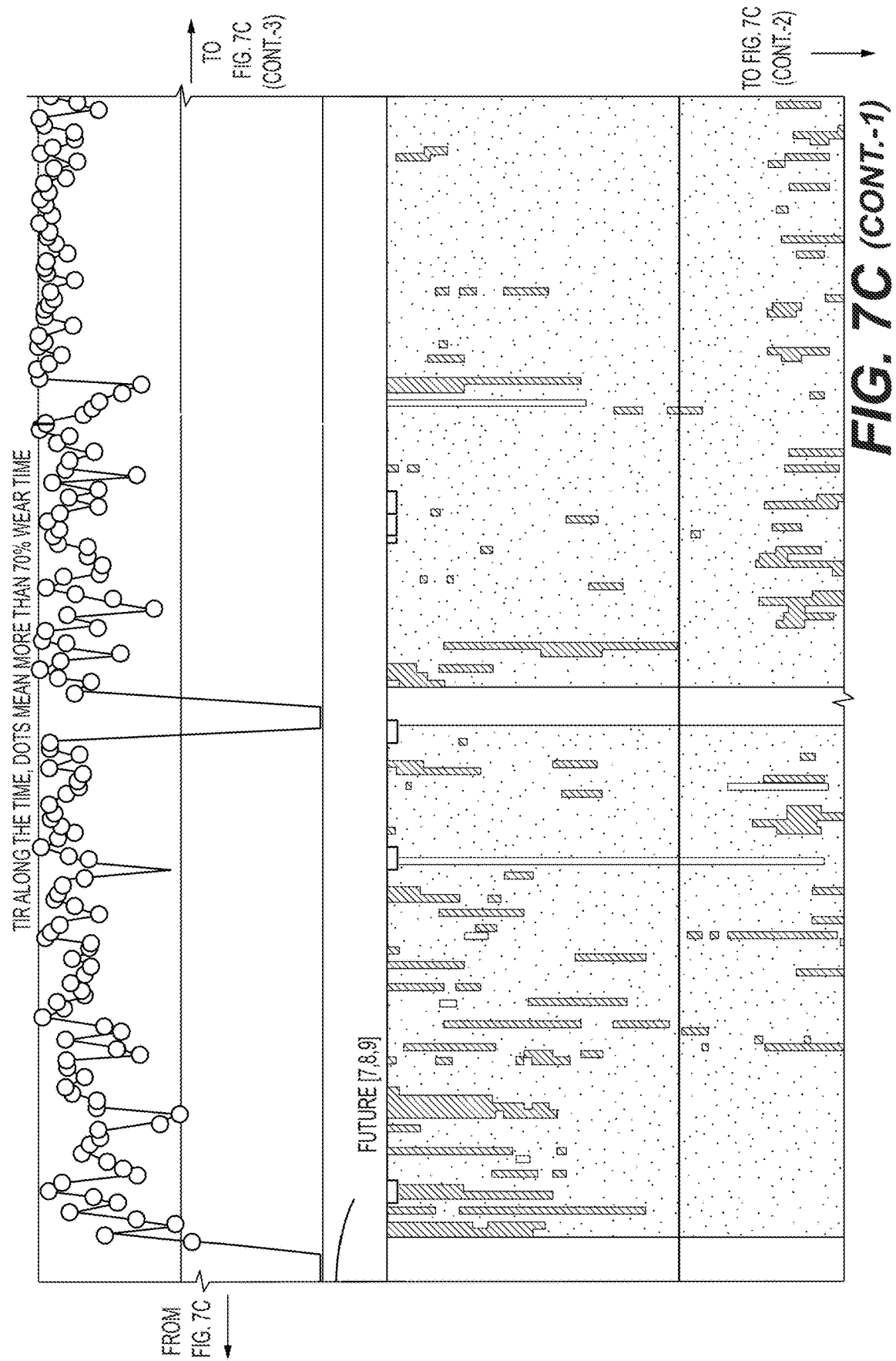

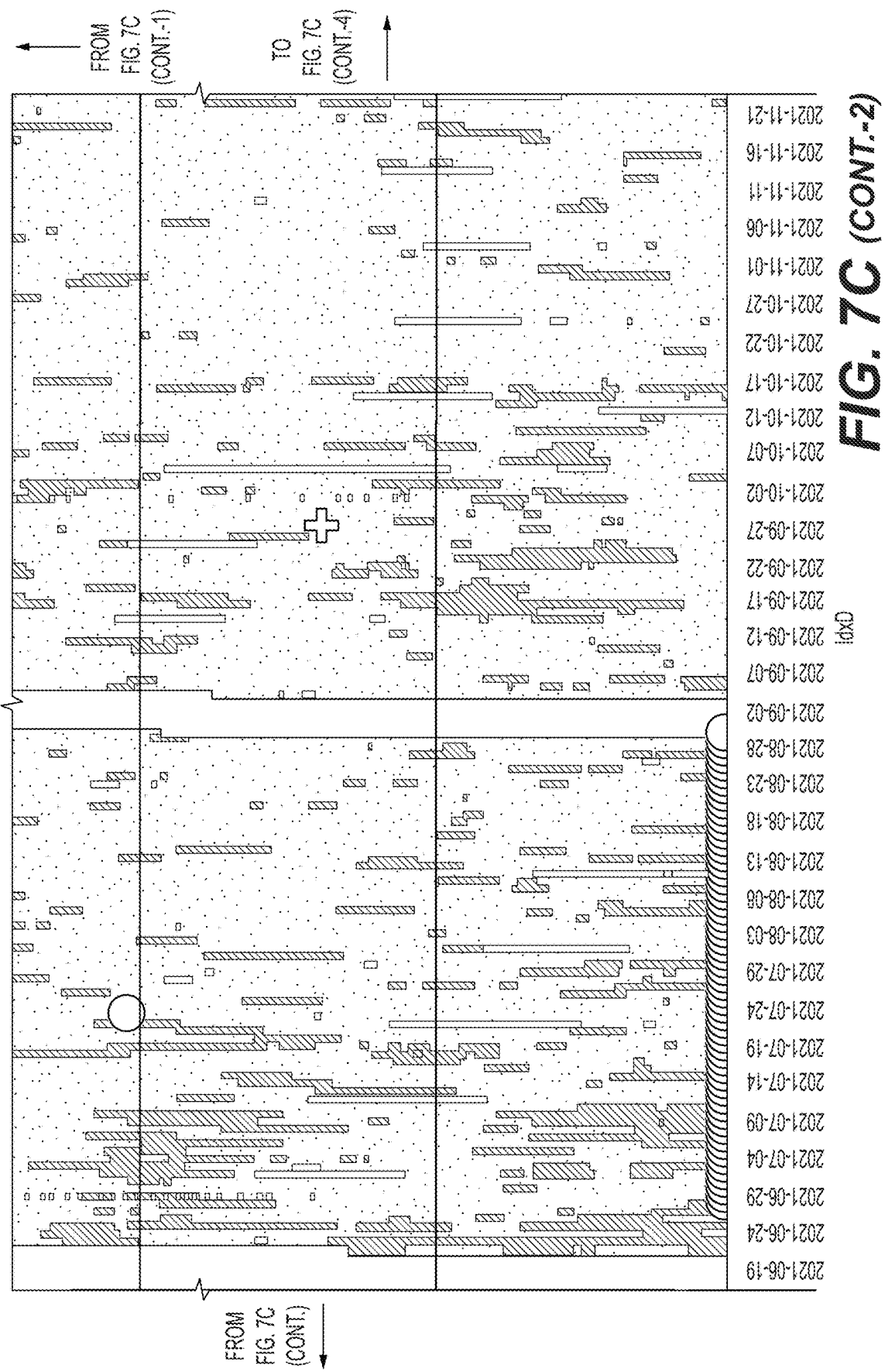

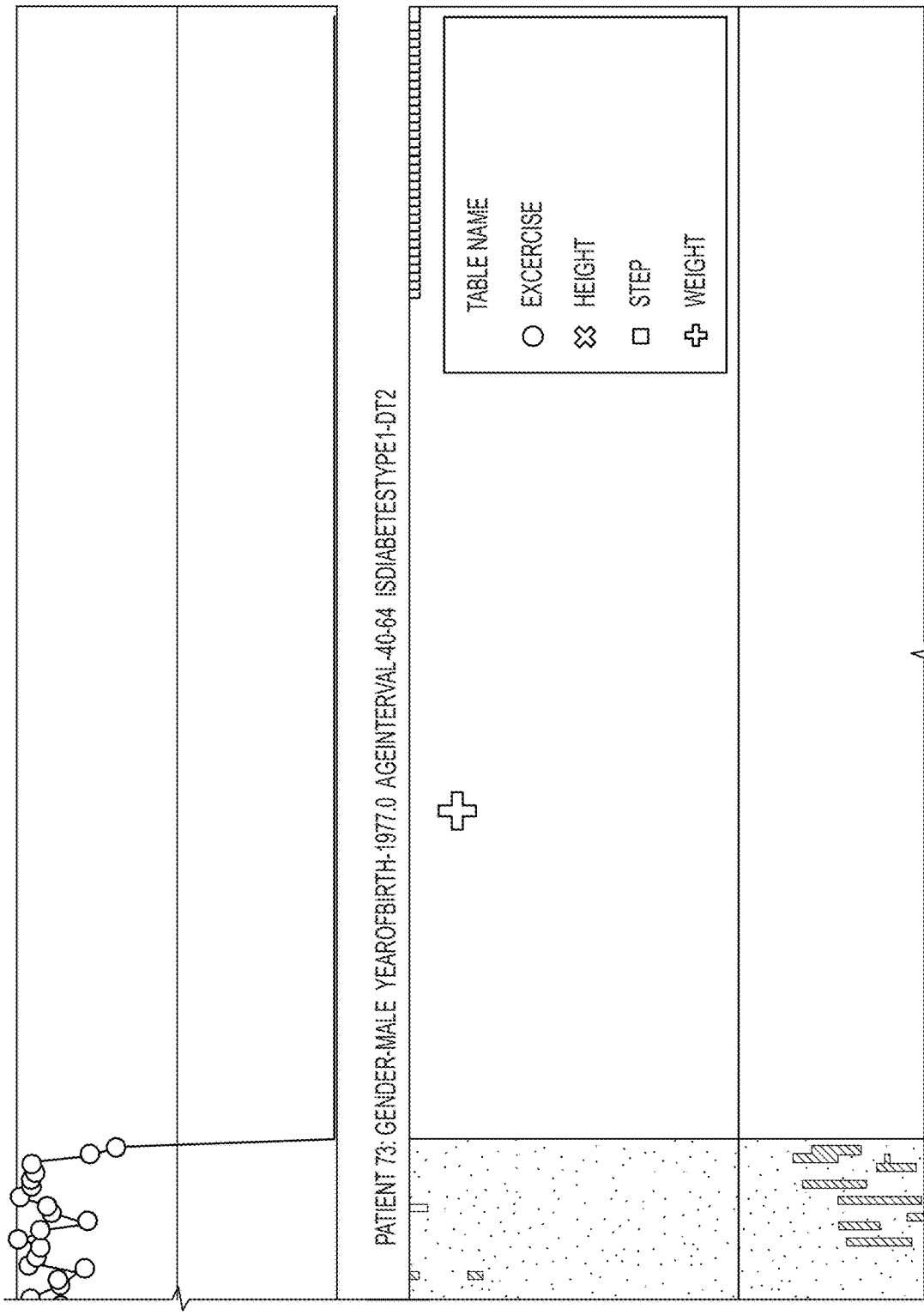

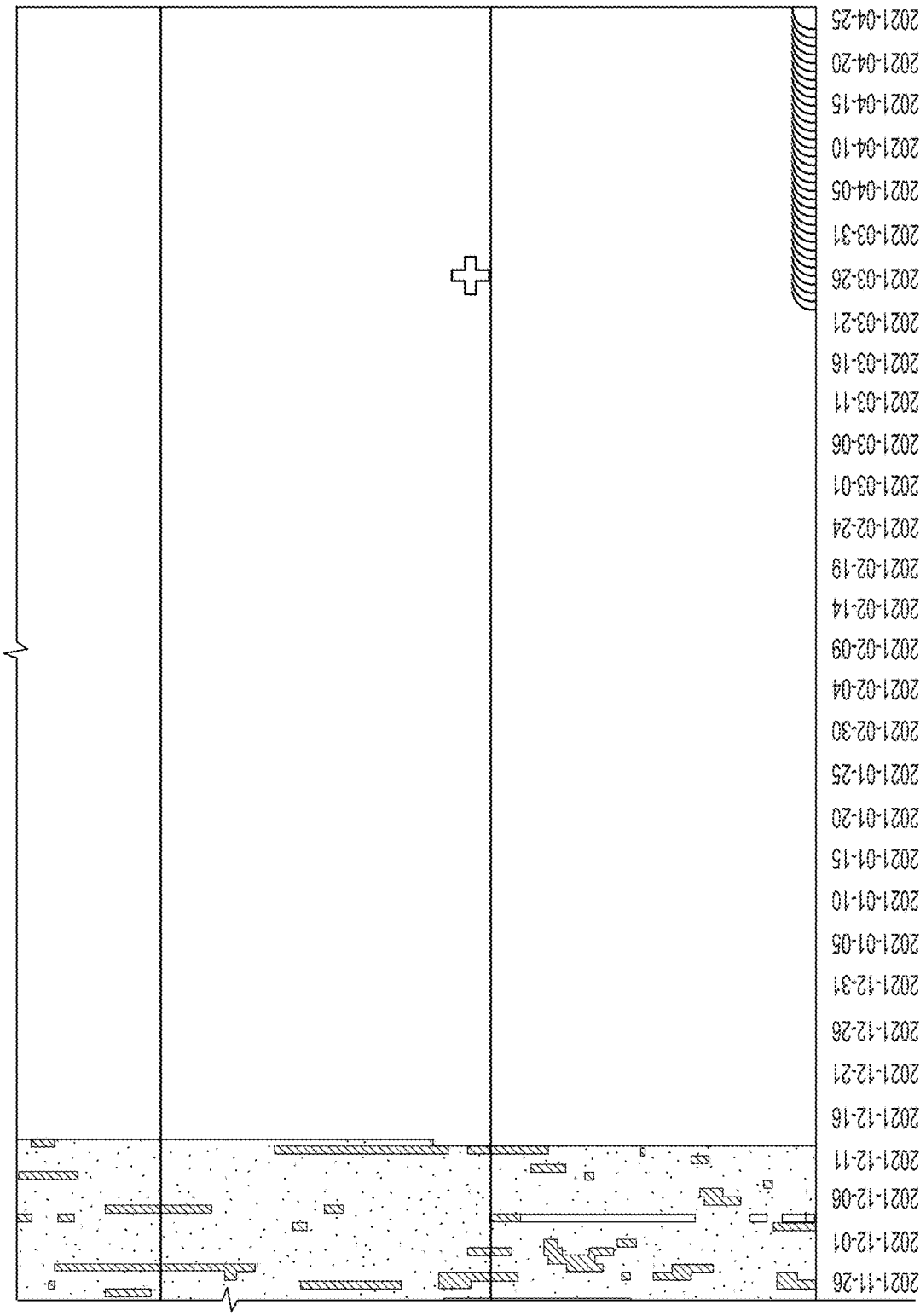

INPUT PERIODS: [1, 2, 3]
INPUT: CGM RECORD > 2880, MEDAL RECORD > 0
OUTPUT: CGM RECORD > 2880, MEDAL RECORD > 0

TIR_DELTA: C3

| DIABETES TYPE | FUTURE PERIOD | SAMPLE SIZE | LABEL DESCRIPTION | MODEL | ACCURACY | AUC | RECALL | PREC. | F1 |
|---|---|---|---|---|---|---|---|---|---|
| ALL | [7, 8, 9] | 209 | {1:84, 2:41, 3:84} | RANDOM FOREST CLASSIFIER | 51.59% | 63.79% | 51.59% | 50.60% | 48.87% |
| ALL | [10, 11, 12] | 183 | {1:73, 2:37, 3:73} | RANDOM FOREST CLASSIFIER | 47.36% | 52.26% | 47.36% | 43.00% | 43.26% |
| ALL | [7, 8, 9, 10, 11, 12] | 210 | {1:84, 2:42, 3:84} | ADA BOOST CLASSIFIER | 48.11% | 56.53% | 48.11% | 49.27% | 45.77% |
| DT1 | [7, 8, 9] | 116 | {1:47, 2:23, 3:46} | LINEAR DISCRIMINANT ANALYSIS | 55.24% | 61.74% | 55.24% | 53.40% | 51.65% |
| DT2 | [7, 8, 9] | 93 | {1:37, 2:19, 3:37} | RIDGE CLASSIFIER | 43.00% | 0.00% | 43.00% | 36.38% | 36.35% |

TIR_DELTA: C2

| DIABETES TYPE | FUTURE PERIOD | SAMPLE SIZE | LABEL DESCRIPTION | MODEL | ACCURACY | AUC | RECALL | PREC. | F1 |
|---|---|---|---|---|---|---|---|---|---|
| ALL | [7, 8, 9] | 209 | {0:105, 1:104} | LOGISTIC REGRESSION | 62.95% | 65.56% | 60.67% | 62.61% | 58.31% |
| ALL | [10, 11, 12] | 183 | {0:93, 1:90} | RIDGE CLASSIFIER | 60.55% | 0.00% | 57.67% | 66.67% | 60.41% |
| ALL | [7, 8, 9, 10, 11, 12] | 210 | {0:114, 1:96} | LOGISTIC REGRESSION | 58.33% | 58.63% | 53.67% | 55.00% | 53.38% |
| DT1 | [7, 8, 9] | 116 | {0:58, 1:58} | DECISION TREE CLASSIFIER | 62.14% | 62.92% | 65.00% | 68.33% | 63.24% |
| DT2 | [7, 8, 9] | 93 | {0:47, 1:46} | RIDGE CLASSIFIER | 64.33% | 0.00% | 60.00% | 67.67% | 60.88% |

FIG. 9A

INPUT PERIODS: [1, 2, 3]; OUTPUT PERIODS: [7, 8, 9]
INPUT: CGM RECORD > 0, MEDAL RECORD > 0
OUTPUT: CGM RECORD > 0, MEDAL RECORD > 0

ENGAGEMENT OF CGM: C2

| DIABETES TYPE | SAMPLE SIZE | LABEL DESCRIPTION | MODEL | ACCURACY | AUC | RECALL | PREC. | F1 |
|---|---|---|---|---|---|---|---|---|
| DT1 | 273 | {0: 116, 1: 157} | GRADIENT BOOSTING CLASSIFIER | 76.25% | 80.09% | 88.75% | 75.85% | 81.47% |
| DT2 | 226 | {0: 90, 1: 136} | RANDOM FOREST CLASSIFIER | 79.29% | 80.42% | 97.50% | 76.62% | 85.57% |

ENGAGEMENT OF mHEALTH APPLICATION: C2

| DIABETES TYPE | SAMPLE SIZE | LABEL DESCRIPTION | MODEL | ACCURACY | AUC | RECALL | PREC. | F1 |
|---|---|---|---|---|---|---|---|---|
| DT1 | 273 | {0: 215, 1: 58} | LOGISTIC REGRESSION | 90.08% | 81.98% | 72.50% | 84.33% | 75.86% |
| DT2 | 226 | {0: 166, 1: 60} | RANDOM FOREST CLASSIFIER | 89.68% | 88.26% | 74.17% | 85.83% | 78.64% |

FIG. 9B

INPUT PERIODS: [1, 2, 3]; OUTPUT PERIODS: [7, 8, 9]
INPUT: CGM RECORD > 2880, MEDAL RECORD > 0
OUTPUT: CGM RECORD > 2880, MEDAL RECORD > 0

HEALTH: TIR-C3

920

| DIABETES TYPE | SAMPLE SIZE | LABEL DESCRIPTION | MODEL | ACCURACY | AUC | RECALL | PREC. | F1 |
|---|---|---|---|---|---|---|---|---|
| PROFILE+CGM+MEDAL | 209 | {1: 84, 2: 41, 3:84} | RANDOM FOREST CLASSIFIER | 51.59% | 63.79% | 51.59% | 50.60% | 48.87% |
| PROFILE+CGM | 209 | {1: 84, 2: 41, 3:84} | DECISION TREE CLASSIFIER | 47.58% | 58.93% | 47.58% | 49.94% | 47.10% |

HEALTH: TIR-C2

922

| DIABETES TYPE | SAMPLE SIZE | LABEL DESCRIPTION | MODEL | ACCURACY | AUC | RECALL | PREC. | F1 |
|---|---|---|---|---|---|---|---|---|
| PROFILE+CGM+MEDAL | 209 | {0: 105, 1: 104} | LOGISTIC REGRESSION | 62.95% | 65.56% | 60.67% | 62.61% | 58.31% |
| PROFILE+CGM | 209 | {0: 105, 1: 104} | GRADIENT BOOSTING CLASSIFIER | 62.21% | 60.28% | 53.67% | 62.89% | 59.09% |

*FIG. 9C*

HEALTH: TIR-C3

INPUT PERIODS: [1, 2, 3]; OUTPUT PERIODS: [7, 8, 9]
INPUT: CGM RECORD > 2880, MEDAL RECORD > 5
OUTPUT: CGM RECORD > 2880, MEDAL RECORD > 0

| DIABETES TYPE | SAMPLE SIZE | LABEL DESCRIPTION | MODEL | ACCURACY | AUC | RECALL | PREC. | F1 |
|---|---|---|---|---|---|---|---|---|
| PROFILE+CGM+MEDAL | 75 | {1: 30, 2: 15, 3: 30} | GRADIENT BOOSTING CLASSIFIER | 68.50% | 50.50% | 68.50% | 63.29% | 63.33% |
| PROFILE+CGM | 75 | {1: 30, 2: 15, 3: 30} | K NEIGHBORS CLASSIFIER | 46.50% | 36.87% | 46.50% | 34.52% | 36.79% |

930

FOCUS ON THE PATIENTS HAVE BOTH CGM
AND MEDAL IN INPUT PERIODS.

HEALTH: TIR-C2

| DIABETES TYPE | SAMPLE SIZE | LABEL DESCRIPTION | MODEL | ACCURACY | AUC | RECALL | PREC. | F1 |
|---|---|---|---|---|---|---|---|---|
| PROFILE+CGM+MEDAL | 75 | {0: 39, 1: 36} | DECISION TREE CLASSIFIER | 65.50% | 64.17% | 50.00% | 53.33% | 49.33% |
| PROFILE+CGM | 75 | {0: 39, 1: 36} | DECISION TREE CLASSIFIER | 61.00% | 62.50% | 65.00% | 60.00% | 57.00% |

INPUT PERIODS: [1, 2, 3]; OUTPUT PERIODS: [7, 8, 9]
INPUT: CGM RECORD > 0, MEDAL RECORD > 5
OUTPUT: CGM RECORD > 0, MEDAL RECORD > 0

ENGAGEMENT OF CGM: C2

| DIABETES TYPE | SAMPLE SIZE | LABEL DESCRIPTION | MODEL | ACCURACY | AUC | RECALL | PREC. | F1 |
|---|---|---|---|---|---|---|---|---|
| PROFILE+CGM+MEDAL | 169 | {0: 56, 1: 113} | EXTREME GRADIENT BOOSTING | 78.78% | 80.18% | 95.24% | 79.19% | 85.91% |
| PROFILE+CGM | 169 | {0: 56, 1: 113} | EXTRA TREES CLASSIFIER | 77.78% | 74.72% | 89.29% | 82.20% | 84.18% |

940

ENAGEMENT OF mHEALTH APPLICATION: C2

| DIABETES TYPE | SAMPLE SIZE | LABEL DESCRIPTION | MODEL | ACCURACY | AUC | RECALL | PREC. | F1 |
|---|---|---|---|---|---|---|---|---|
| PROFILE+CGM+MEDAL | 169 | {0: 64, 1: 105} | RANDOM FOREST CLASSIFIER | 69.11% | 75.71% | 85.00% | 73.04% | 77.52% |
| PROFILE+CGM | 169 | {0: 64, 1: 105} | LINEAR DISCRIMINANT ANALYSIS | 67.89% | 67.39% | 72.67% | 77.71% | 73.63% |

TIR DELTA - C3

| QUESTION VARIANTS | DATA (COHORT NUMBER, TRAIN/TEST, FEATURES) | BEST MODEL | ACCURACY | AUC | PRECISE | RECALL | F1 |
|---|---|---|---|---|---|---|---|
| Q1: BASELINE | 227 | RANDOM FOREST CLASSIFIER | 0.5696 | 0.6873 | 0.5587 | 0.5204 | 0.5373 |
| Q2: T2D | 102 | RANDOM FOREST CLASSIFIER | 0.4625 | 0.6795 | 0.4879 | 0.4667 | 0.4426 |
| Q3: T1D | 125 | RANDOM FOREST CLASSIFIER | 0.5153 | 0.6412 | 0.3941 | 0.3256 | 0.4395 |
| Q4: NO MEDAL | 227 | RANDOM FOREST CLASSIFIER | 0.4871 | 0.6624 | 0.4767 | 0.4451 | 0.4654 |

*FIG. 9F*

TIR DELTA - C2

| QUESTION VARIANTS | DATA (COHORT NUMBER) | BEST MODEL | ACCURACY | AUC | PRECISE | RECALL | F1 |
|---|---|---|---|---|---|---|---|
| Q1: BASELINE | 227 | LIGHT GRADIENT BOOSTING MACHINE | 0.6892 | 0.7229 | 0.6554 | 0.6554 | 0.6607 |
| Q2: T2D | 102 | QUADRATIC DISCRIMINANT ANALYSIS | 0.6071 | 0.6125 | 0.5750 | 0.6250 | 0.5783 |
| Q3: T1D | 125 | NAIVE BAYES | 0.5292 | 0.5919 | 0.5444 | 0.6550 | 0.5647 |
| Q4: NO MEDAL | 227 | LIGHT GRADIENT BOOSTING MACHINE | 0.6579 | 0.7139 | 0.6306 | 0.6286 | 0.6255 |

*FIG. 9G*

TIR STATUS - C2

| QUESTION VARIANTS | DATA (COHORT NUMBER, TRAIN/TEST, FEATURES) | BEST MODEL | ACCURACY | AUC | PRECISE | RECALL | F1 |
|---|---|---|---|---|---|---|---|
| Q1: BASELINE | 304 | LIGHT GRADIENT BOOSTING MACHINE | 0.7970 | 0.8813 | 0.8248 | 0.7500 | 0.7812 |
| Q2: T2D | 140 | RANDOM FOREST CLASSIFIER | 0.7956 | 0.8740 | 0.8198 | 0.7700 | 0.7833 |
| Q3: T1D | 125 | EXTRA TREES CLASSIFIER | 0.8403 | 0.9050 | 0.8539 | 0.8850 | 0.8504 |
| Q4: NO MEDAL | 304 | LIGHT GRADIENT BOOSTING MACHINE | 0.8206 | 0.8799 | 0.8528 | 0.7700 | 0.8035 |

FIG. 9I

GRI DELTA - C2

| QUESTION VARIANTS | DATA (COHORT NUMBER) | BEST MODEL | ACCURACY | AUC | PRECISE | RECALL | F1 |
|---|---|---|---|---|---|---|---|
| Q1: BASELINE | 227 | EXTREME GRADIENT BOOSTING | 0.6467 | 0.6993 | 0.6534 | 0.5911 | 0.6029 |
| Q2: T2D | 102 | GRADIENT BOOSTING CLASSIFIER | 0.5214 | 0.5625 | 0.4450 | 0.4917 | 0.4452 |
| Q3: T1D | 125 | ADA BOOST CLASSIFIER | 0.5986 | 0.6588 | 0.5667 | 0.6000 | 0.5676 |
| Q4: NO MEDAL | 227 | GRADIENT BOOSTING CLASSIFIER | 0.6392 | 0.6945 | 0.6234 | 0.6036 | 0.6018 |

FIG. 9K

GRI DELTA - C3

| QUESTION VARIANTS | DATA (SIZE, TRAIN/TEST) | BEST MODEL | ACCURACY | AUC | PRECISE | RECALL | F1 |
|---|---|---|---|---|---|---|---|
| Q1: BASELINE | 227 | EXTRA TREES CLASSIFIER | 0.5946 | 0.6411 | 0.4772 | 0.5946 | 0.5186 |
| Q2: T2D | 102 | RANDOM FOREST CLASSIFIER | 0.5625 | 0.6166 | 0.4597 | 0.5625 | 0.4941 |
| Q3: T1D | 125 | EXTREME GRADIENT BOOSTING | 0.6347 | 0.6175 | 0.5031 | 0.6347 | 0.5575 |
| Q4: NO MEDAL | 227 | NAIVE BAYES | 0.4046 | 0.6883 | 0.4046 | 0.6698 | 0.4145 |

GRI STATUTS - C2

| QUESTION VARIANTS | DATA (COHORT NUMBER, TRAIN/TEST, FEATURES) | BEST MODEL | ACCURACY | AUC | PRECISE | RECALL | F1 |
|---|---|---|---|---|---|---|---|
| Q1: BASELINE | 304 | GRADIENT BOOSTING CLASSIFIER | 0.8353 | 0.9135 | 0.7355 | 0.7405 | 0.7287 |
| Q2: T2D | 140 | EXTREME GRADIENT BOOSTING | 0.8033 | 0.8932 | 0.7988 | 0.785 | 0.7728 |
| Q3: T1D | 125 | LIGHT GRADIENT BOOSTING MACHINE | 0.8864 | 0.9389 | 0.7917 | 0.7167 | 0.7157 |
| Q4: NO MEDAL | 304 | EXTREME GRADIENT BOOSTING | 0.8392 | 0.9210 | 0.7631 | 0.7381 | 0.7354 |

FIG. 9M

ENGAGEMENT OF mHEALTH APPLICATION - C2

| QUESTION VARIANTS | DATA (SIZE, TRAIN/TEST) | BEST MODEL | ACCURACY | AUC | PRECISE | RECALL | F1 |
|---|---|---|---|---|---|---|---|
| Q1: ALL | 499 | RANDOM FOREST CLASSIFIER | 0.8710 | 0.8958 | 0.8167 | 0.7150 | 0.7440 |
| Q2: T2D | 226 | RANDOM FOREST CLASSIFIER | 0.8667 | 0.8944 | 0.8167 | 0.7150 | 0.7440 |
| Q3: T1D | 273 | EXTRA TREES CLASSIFIER | 0.9000 | 0.9358 | 0.8117 | 0.7500 | 0.7621 |
| Q4: ONLY CGM AND DEMO INFO | 499 | RANDOM FOREST CLASSIFIER | 0.7422 | 0.5510 | 0.3333 | 0.0708 | 0.1116 |

*FIG. 9N*

MANUAL ENGAGEMENT OF mHEALTH APPLICATION - C2

| QUESTION VARIANTS | DATA (SIZE, TRAIN/TEST) | BEST MODEL | ACCURACY | AUC | PRECISE | RECALL | F1 |
|---|---|---|---|---|---|---|---|
| Q1: ALL | 499 | RANDOM FOREST CLASSIFIER | 0.9313 | 0.8896 | 0.7250 | 0.4583 | 0.5317 |
| Q2: T2D | 226 | EXTRA TREES CLASSIFIER | 0.9179 | 0.8634 | 0.6667 | 0.5500 | 0.5767 |
| Q3: T1D | 273 | RANDOM FOREST CLASSIFIER | 0.9479 | 0.8917 | 0.2500 | 0.3000 | 0.2667 |
| Q4: ONLY CGM AND DEMO INFO | 499 | RANDOM FOREST CLASSIFIER | 0.8164 | 0.6639 | 0.1927 | 0.3333 | 0.2406 |

CGM ENGAGEMENT - C2

| QUESTION VARIANTS | DATA (SIZE) | BEST MODEL | ACCURACY | AUC | PRECISE | RECALL | F1 |
|---|---|---|---|---|---|---|---|
| Q1: ALL | 499 | RANDOM FOREST CLASSIFIER | 0.8224 | 0.8643 | 0.8169 | 0.9152 | 0.8622 |
| Q2: T2D | 226 | EXTRA TREES CLASSIFIER | 0.8542 | 0.8873 | 0.8486 | 0.9389 | 0.8897 |
| Q3: T1D | 273 | RANDOM FOREST CLASSIFIER | 0.8058 | 0.8118 | 0.8147 | 0.8795 | 0.8440 |
| Q4: ONLY CGM AND DEMO INFO | 499 | EXTRA TREES CLASSIFIER | 0.8282 | 0.8555 | 0.8260 | 0.9106 | 0.8650 |

CGM ENGAGEMENT BASED ON MEDAL DATA - C2

| QUESTION VARIANTS | DATA (SIZE, TRAIN/TEST) | BEST MODEL | ACCURACY | AUC | PRECISE | RECALL | F1 |
|---|---|---|---|---|---|---|---|
| Q1: ALL | (499, 306) (349, 306) (150, 306) | RANDOM FOREST CLASSIFIER | 0.5845 | 0.5180 | 0.6212 | 0.8123 | 0.7028 |
| Q2: T2D | (226, 314) (158, 314) (68, 314) | LIGHT GRADIENT BOOSTING MACHINE | 0.5871 | 0.4807 | 0.6122 | 0.8944 | 0.7247 |
| Q3: T1D | (273, 264) (191, 264) (82, 264) | LIGHT GRADIENT BOOSTING MACHINE | 0.6432 | 0.5807 | 0.6884 | 0.7280 | 0.7006 |

FIG. 9T

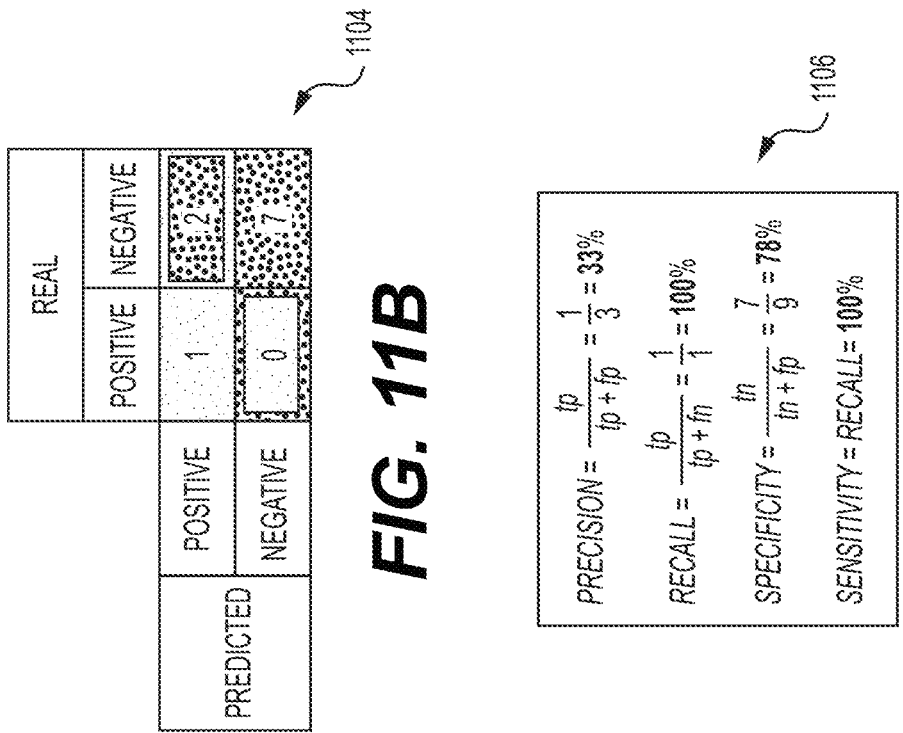
FIG. 11B
FIG. 11C
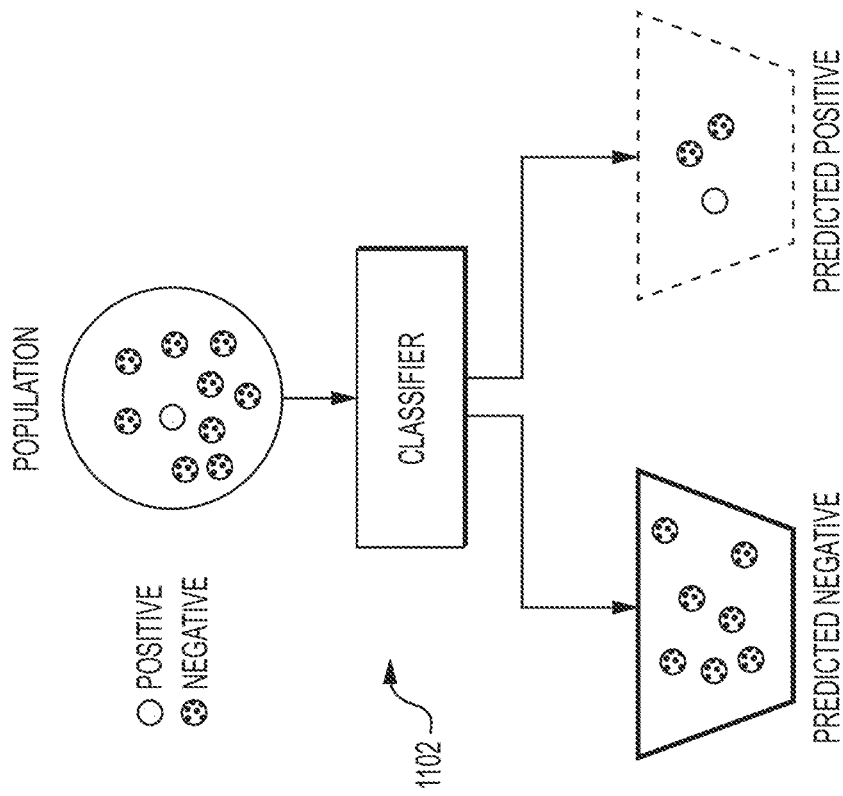
FIG. 11A

SYSTEMS AND METHODS FOR CONTINUOUS GLUCOSE MONITORING OUTCOME PREDICTIONS

CROSS-REFERENCE TO RELATED APPLICATION(S)

This patent application is a continuation of and claims the benefit of priority to International Application No. PCT/US2024/023736, filed on Apr. 9, 2024, which claims priority to U.S. Provisional Application No. 63/495,468, filed Apr. 11, 2023, the entire disclosure of each of which is hereby incorporated by reference in its entirety.

TECHNICAL FIELD

The present disclosure relates generally to predicting a user's future glucose and engagement levels, and, in some embodiments, more specifically to using one or more machine learning models to determine health and engagement predictions.

BACKGROUND

Increased healthcare costs have limited user access to appropriate care. At the same time, healthcare companies have increased provider workloads and limited physician-user interactions. Diabetes treatment often relies on sporadic readings (e.g., blood glucose readings) that do not provide ample data to effectively provide treatment options or sufficient data for making predictions of health and/or engagement outcomes. Such readings are often used in isolation such that changes are recommended based on one or two readings. Any medical, dietary, and/or lifestyle changes recommended as a result of a given reading are limited given the limited data received via the sporadic readings.

The introduction provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

This disclosure is directed to a computer-implemented method for predicting health and engagement levels for a user. The method includes receiving the user's glucose levels collected by a continuous glucose monitoring (CGM) device over a time period. The method further includes receiving engagement data associated with the user, the engagement data collected by a computing device over the time period, wherein the engagement data are associated with the user's medication intake, diet, physical activity, laboratory results, and education activity. The method also includes determining a first glycemia risk index (GRI) value based on a first amount of time the user is hypoglycemic during the time period and a second amount of time the user is hyperglycemic during the time period. The method further yet includes determining, using a machine learning model and responsive to the user's glucose levels and the engagement data collected over the time period, one or more predictions for future glucose levels for the user including a prediction that a future GRI value is greater than or less than the first GRI value, and determining, using the machine learning model and responsive to the user's engagement data collected over the time period, one or more predictions for future engagement levels.

This disclosure is directed to a computer-implemented method for training a machine learning model for predicting health and engagement levels for a user. The method includes receiving first glucose levels of the user collected by a continuous glucose monitoring (CGM) device over a first time period, receiving second glucose levels of the user collected by the CGM device over a second time period subsequent to the first period of time, receiving first engagement data associated with the user, the first engagement data collected by a computing device over the first time period, and receiving second engagement data associated with the user, the second engagement data collected by the computing device over the second time period, wherein the first engagement data and the second engagement data are associated with one or more of the user's medication intake, diet, physical activity, laboratory results, and education activity. The method further includes training a machine learning model to generate a trained machine learning model based on a machine learning algorithm and using training data comprising the first glucose levels, the second glucose levels, the first engagement data, and the second engagement data, and determining one or more patterns in the training data.

This disclosure is also directed to a system for predicting glucose levels and engagement, the system including a memory having processor-readable instructions stored therein, and a processor configured to access the memory and execute the processor-readable instructions, which, when executed by the processor configures the processor to perform a method. The method includes receiving the user's glucose levels over a time period using a continuous glucose monitoring (CGM) device configured to obtain glucose values using a component that penetrates a skin of the user, and receiving engagement data associated with the user, the engagement data collected by one or more electronic sensors via a computing device over the time period, wherein the engagement data are associated with one or more of the user's medication intake, diet, physical activity, laboratory results, and education activity. The method further includes determining a first glycemia risk index (GRI) value based on a first amount of time the user is hypoglycemic during the time period and a second amount of time the user is hyperglycemic during the time period. The method also includes determining, using a machine learning model and responsive to the user's glucose levels and the engagement data collected over the time period, one or more predictions for future glucose levels for the user including a prediction that a future GRI value is greater than or less than the first GRI value, and determining, using the machine learning model and responsive to the user's engagement data collected over the time period, one or more predictions for future engagement levels.

BRIEF DESCRIPTION OF THE DRAWINGS

The accompanying drawings, which are incorporated in and constitute a part of this specification, illustrate examples of the disclosure and together with the description, serve to explain the principles of the disclosure.

FIG. 7A-7C show diagrams depicting the use of glucose and engagement data to predict future health and engagement outcomes, in accordance with one or more embodiments.

FIGS. 11A-11C are diagrams depicting relationships between precision, recall, specificity, and sensitivity, in accordance with one or more embodiments.

DETAILED DESCRIPTION

Reference will now be made in detail to examples of the disclosure, which are illustrated in the accompanying drawings. Wherever possible, the same reference numbers will be used throughout the drawings to refer to the same or like parts.

In the discussion that follows, relative terms such as "about," "substantially," "approximately," etc. are used to indicate a possible variation of +10% in a stated numeric value. It should be noted that the description set forth herein is merely illustrative in nature and is not intended to limit the examples of the subject matter, or the application and uses of such examples. Any embodiments described herein as exemplary is not to be construed as preferred or advantageous over other embodiments. Rather, as alluded to above, the term "exemplary" is used in the sense of example or "illustrative," rather than "ideal." The terms "comprise," "include," "have," "with," and any variations thereof are used synonymously to denote or describe a non-exclusive inclusion. As such, a process, method, article, or apparatus that uses such terms does not include only those steps, structure or elements but may include other steps, structures or elements not expressly listed or inherent to such process, method, article, or apparatus. Further, the terms "first," "second," and the like, herein do not denote any order, quantity, or importance, but rather are used to distinguish one element from another. Moreover, the terms "a" and "an" herein do not denote a limitation of quantity, but rather denote the presence of at least one of the referenced item.

Healthcare and Computing Environment

Figure 1:
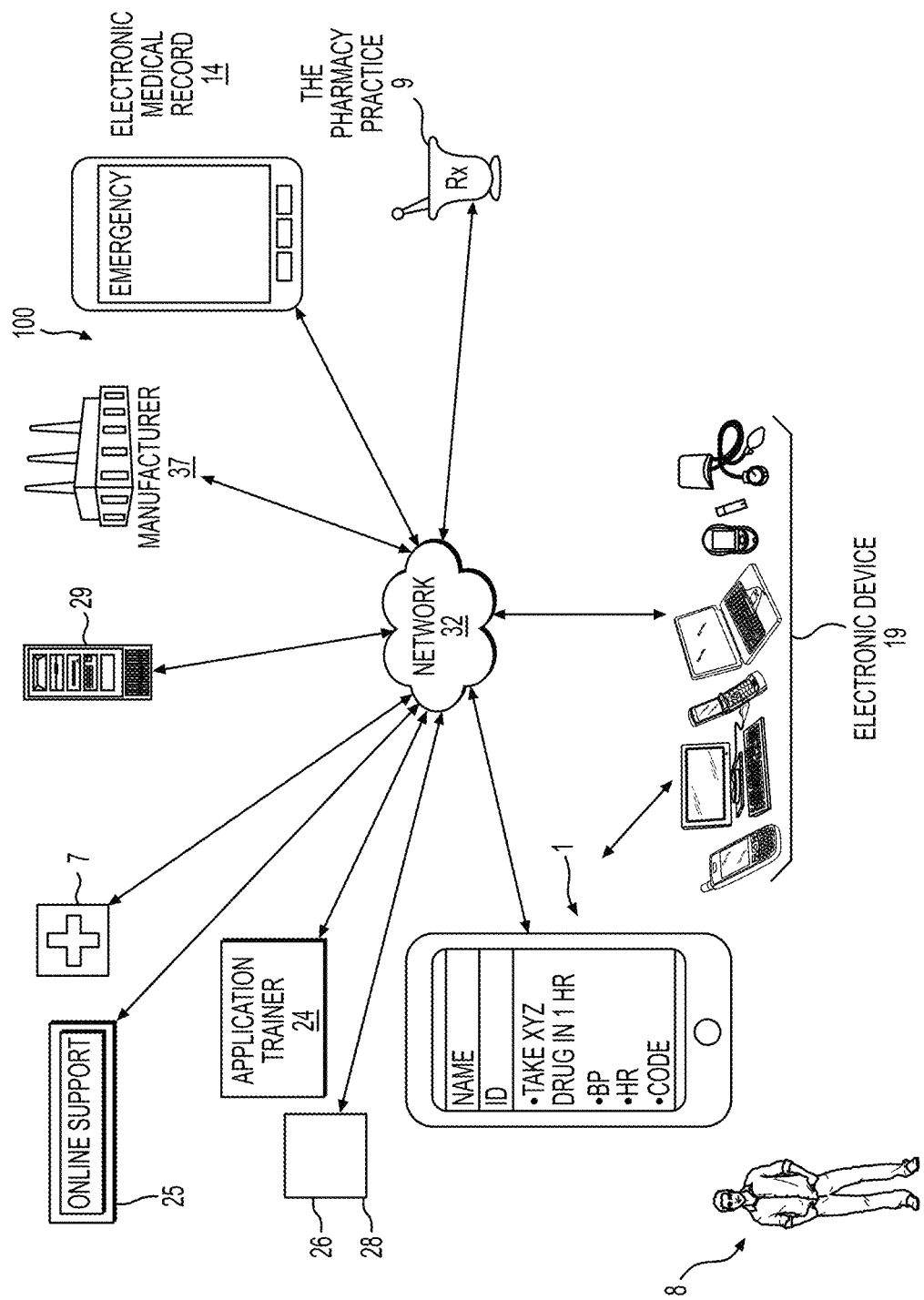
FIG. 1 shows a schematic illustration of a health management system, in accordance with one or more embodiments.

FIG. 1 is a block diagram of a health management system 100, according to an example of the present disclosure. A user (e.g., a patient, consumer, or the like) 8 having an electronic device 19, such as a mobile device, computer, medical device, or any other electronic device configured to access an electronic network 32, such as the Internet, may communicate with or otherwise access a mobile health (mHealth) application 1. In some examples, network 32 may include wireless or wired links, such as mobile telephone networks, Wi-Fi, LANs, WANs, Bluetooth, near-field communication (NFC), or other suitable forms of network communication. Multiple electronic devices 19 may be configured to access electronic network 32. A user 8 may access mHealth application 1 with a single account linked to multiple electronic devices 19 (e.g., via one or more of a mobile phone, a tablet, and a laptop computer). Electronic device 19 also may include, but is not limited to, mobile health devices, a desktop computer or workstation, a laptop computer, a mobile handset, a personal digital assistant (PDA), a cellular telephone, a network appliance, a camera, a smart phone, a smart watch, an enhanced general packet radio service (EGPRS) mobile phone, a media player, a navigation device, a game console, a set-top box, a biometric sensing device with communication capabilities, a smart TV, or any combination of these or other types of computing devices having at least one processor, a local memory, a display (e.g., a monitor or touchscreen display), one or more user input devices, and a network communication interface. The electronic device 19 may include any type or combination of input/output devices, such as a display monitor, keyboard, touchpad, accelerometer, gyroscope, mouse, touchscreen, camera, a projector, a touch panel, a pointing device, a scrolling device, a button, a switch, a motion sensor, an audio sensor, a pressure sensor, a thermal sensor, and/or microphone. Electronic devices 19 also may communicate with each other by any suitable wired or wireless means (e.g., via Wi-Fi, radio frequency (RF), infrared (IR), Bluetooth, Near Field Communication, or any other suitable means) to send and receive information.

mHealth application 1 may be implemented in communication with other entities or networks to send and receive information. In some examples, mHealth application 1 may communicate with one or more applications associated with the user 8 such as, e.g., exercise tracking (e.g., step tracking) applications and/or other health-related applications. mHealth application 1 may be configured to import data from the other applications to analyze and use in generating treatment plans for the user 8. For example, mHealth application 1 may import activity tracking data from another application and use that data to identify patterns between user 8 exercise and glucose values collected prior to the use of mHealth application 1. mHealth application 1 also may import any other suitable data from other mobile health applications such as, e.g., blood pressure, body mass index (BMI), glycated hemoglobin (A1C), exercise type, exercise duration, exercise distance, calories burned, total steps, exercise date, exercise start and stop times, and sleep. mHealth application 1 also may export data to other mobile applications, including, e.g., other mobile health applications having social or interactive features. A healthcare provider 7, such as a physician, may prescribe the application. However, it is also contemplated that mHealth application 1 may not require a prescription, e.g., that it may be a commercially available consumer application accessible without a prescription from a digital distribution platform for computer software. mHealth application 1 may be tailored to a specific user 8 and may be activated in person by the user 8 by visiting a pharmacy 9 or other authorized entity. For example, the user 8 may receive an access code from the pharmacy that authorizes access to mHealth application 1. The user 8 may receive training on using mHealth application 1 by a mHealth support system 25 and/or application trainer 24. mHealth application 1 may include programming 28 of various forms, such as machine learning programming algorithms 26. The user treatment plan may include a prescription (e.g., for a drug, device, and/or therapy), which may be dispensed by the pharmacy 9. The pharmacy 9 may allow the refill of the prescribed product/therapy after receiving authorization based on the user's compliance with his/her healthcare treatment plan. The authorization may be received by the pharmacy 9 by a communication from mHealth application 1, via, e.g., the network 32 and various servers 29. Use of the drug or other medical product/therapy also may be sent to the manufacturer 37 over the network 32 to inform the manufacturer 37 of the amount of medical product or therapy being used by user 8. This information may assist the manufacturer 37 in assessing demand and planning supply of the medical product or therapy. The healthcare provider 7 also may receive a report based on the user information received by mHealth application 1, and may update the user treatment plan based on this information. The user's electronic medical record (EMR) 14 also may be automatically updated via the network 32 based on the user information, which may include electronically transmitted user 8 feedback on the application, received by mHealth application 1. Healthcare provider 7 may be any suitable healthcare provider including, e.g., a doctor, specialist, nurse, educator, social worker, medical assistant (MA), physician assistant or associate (PA), or the like.

Figure 2:
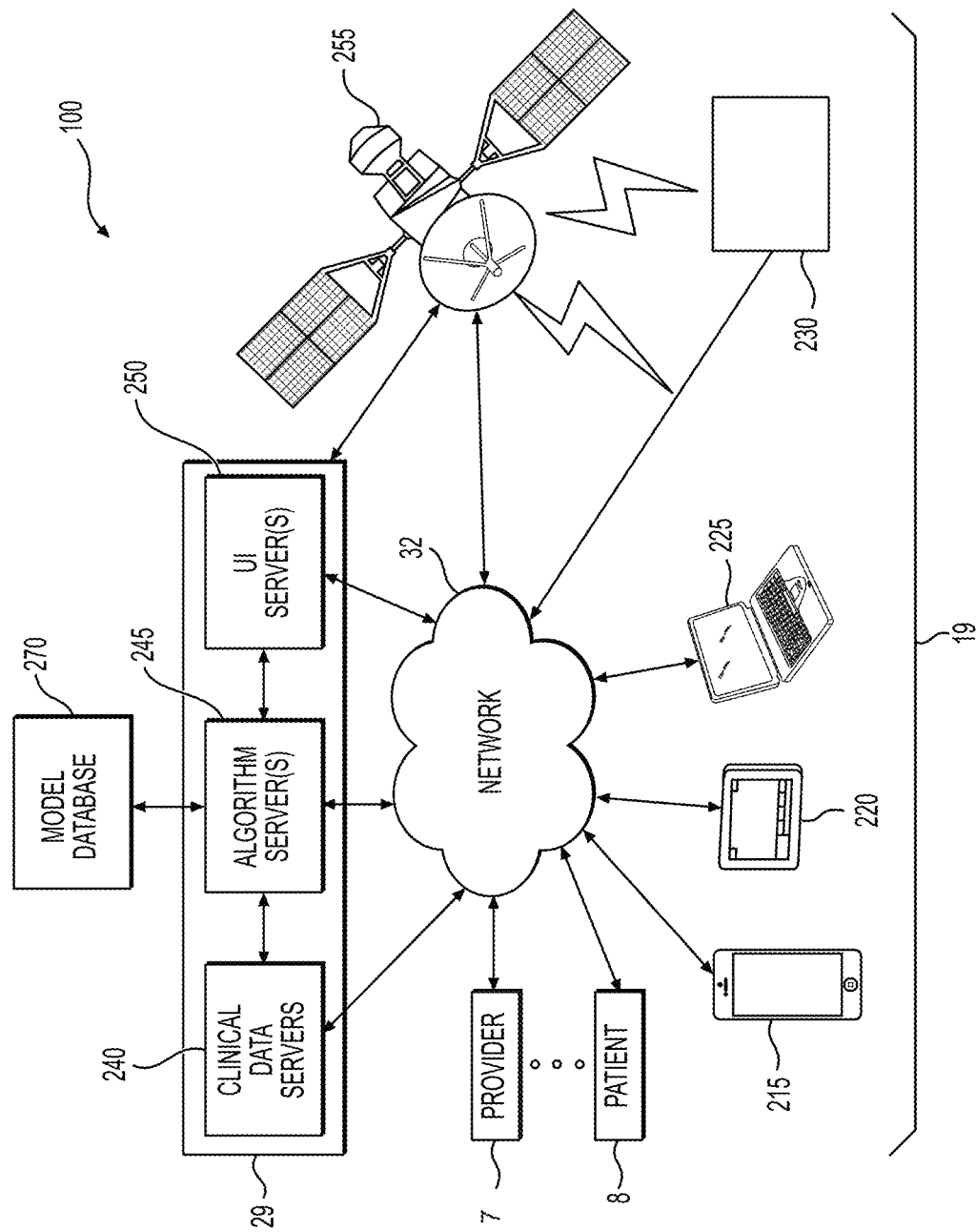
FIG. 2 shows a schematic illustration of a portion of the health management system of FIG. 1, in accordance with one or more embodiments.

FIG. 2 is a schematic diagram of additional aspects of system 100. For example, the system 100 may access decision models stored on a decision model database 270 via network 32. The retrieved decision models may be used for display and/or processing by one or more electronic devices 19, such as a mobile device 215, a tablet device 220, a computer (e.g., a laptop or desktop) 225, a kiosk 230 (e.g., at a kiosk, pharmacy, clinic, or hospital having medical and/or prescription information), and/or any device connected to network 32.

In the example shown in FIG. 2, mobile device 215, tablet device 220, and computer 225 each may be equipped with or include, for example, a global positioning system (GPS) receiver for obtaining and reporting location information, e.g., GPS data, via network 32 to and from any of servers 29 and/or one or more GPS satellites 255.

Each of electronic devices 19, including mobile device 215, tablet device 220, computer 225, and/or kiosk 230, may be configured to send and receive data (e.g., clinical information) to and from a system of servers 29 over network 32. Each of devices 19 may receive information, such as clinical data via the network 32 from servers 29. Servers 29 may include clinical data servers 240, algorithm servers 245, user interface (UI) servers 250, and/or any other suitable servers. Electronic device 19 may include a user interface that is in data communication with UI server 250 via network 32. Each server may access the decision model database 270 to retrieve decision models. Each server may include memory, a processor, and/or a database. For example, the clinical data server 240 may have a processor configured to retrieve clinical data from a provider's database and/or a patient's electronic medical record. The algorithm server 245 may have a database that includes various algorithms, and a processor configured to process the clinical data. The UI server 250 may be configured to receive and process user 8 input, such as clinical decision preferences. The satellite 255 may be configured to send and receive information between servers 29 and devices 19.

The clinical data server 240 may receive clinical data, such as data regarding the user from the electronic device 19 via the network 32 or indirectly via the UI server 250. The clinical data server 240 may save the information in memory, such as a computer readable memory.

The clinical data server 240 also may be in communication with one or more other servers, such as the algorithm server 245 and/or external servers. The servers 29 may include data about provider preferences, and/or user 8 health history. In addition, the clinical data server 240 may include data from other users. The algorithm server 245 may include machine learning, and/or other suitable algorithms. The algorithm server 245 also may be in communication with other external servers and may be updated as desired. For example, the algorithm server 245 may be updated with new algorithms, more powerful programming, and/or more data. The clinical data server 240 and/or the algorithm server 245 may process the information and transmit data to the model database 270 for processing. In one example, algorithm server(s) 245 may obtain a pattern definition in a simple format, predict several time steps in the future by using models, e.g., Markov models, Gaussian, Bayesian, PCA (principal component analysis), multi-variate linear or non-linear regression, and/or classification models such as linear discriminant functions, nonlinear discriminant functions, synthetic discriminant functions random forest algorithms and the like, optimize results based on its predictions, detect transition between patterns, obtain abstract data and extract information to infer higher levels of knowledge, combine higher and lower levels of information to understand about the user 8 and clinical behaviors, infer from multi-temporal (e.g., different time scales) data and associated information, use variable order Markov models, and/or reduce noise over time by employing slope-based and curve smoothing algorithms, clustering algorithms, such as k-means clustering.

Each server in the system of servers 29, including clinical data server 240, algorithm server 245, and UI server 250, may represent any of various types of servers including, but not limited to, a web server, an application server, a proxy server, a network server, or a server farm. Each server in the system of servers 29 may be implemented using, for example, any general-purpose computer capable of serving data to other computing devices including, but not limited to, devices 19 or any other computing device (not shown) via network 32. Such a general-purpose computer can include, but is not limited to, a server device having a processor and memory for executing and storing instructions. The memory may include any type of random access memory (RAM) or read-only memory (ROM) embodied in a physical storage medium, such as magnetic storage including floppy disk, hard disk, or magnetic tape; semiconductor storage such as solid-state disk (SSD) or flash memory; optical disc storage; or magneto-optical disc storage. Software may include one or more applications and an operating system. Hardware can include, but is not limited to, a processor, memory, and graphical UI display. Each server also may have multiple processors and multiple shared or separate memory components that are configured to function together within, for example, a clustered computing environment or server farm.

Figure 3A:
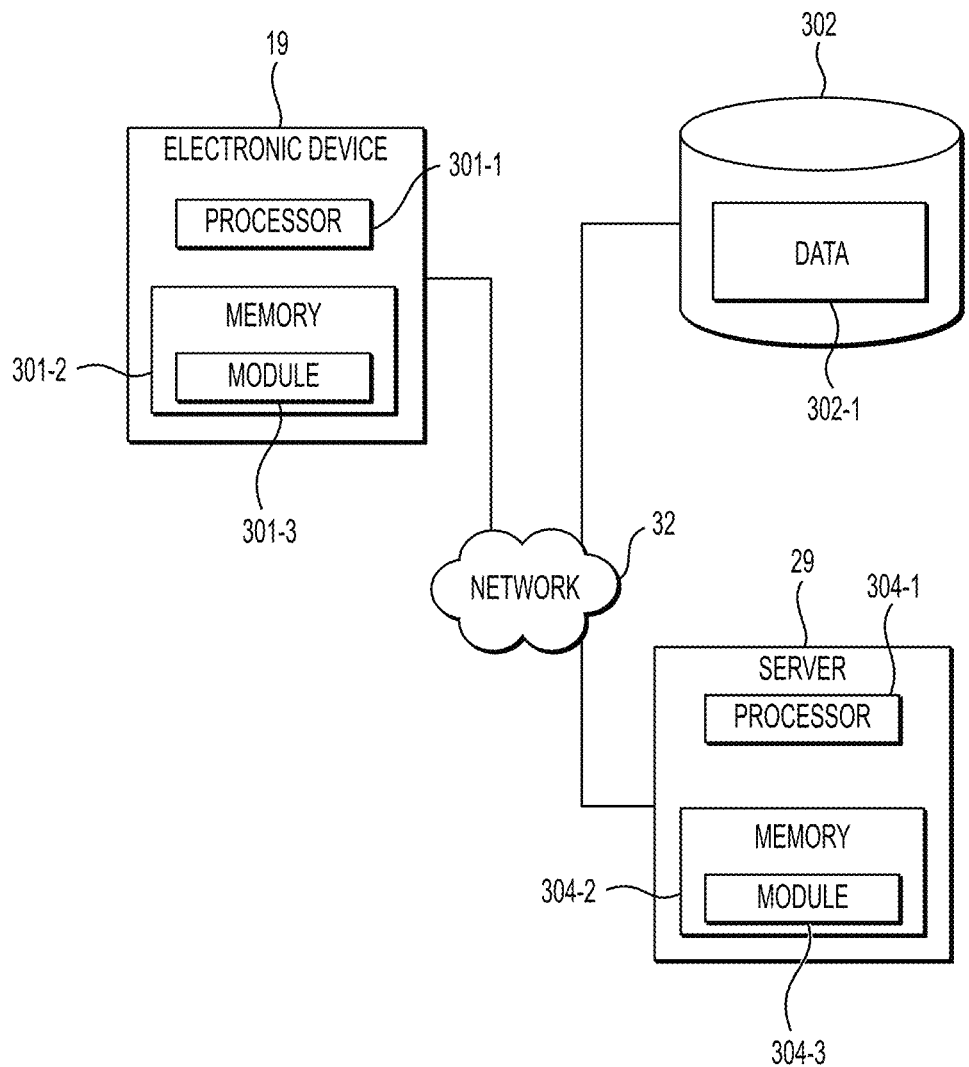
FIG. 3A shows a schematic illustration of another portion of the health management system of FIG. 1, in accordance with one or more embodiments.

FIG. 3A is another representation of a portion of system 100 showing additional details of electronic device 19 and a server 29. Electronic device 19 and server 29 each may contain one or more processors, such as processors 301-1 and 304-1. Processors 301-1 and 304-1 each may be a central processing unit, a microprocessor, a general purpose processor, an application specific processor, or any device that executes instructions. Electronic device 19 and server 29 also may include one or more memories, such as memories 301-2 and 304-2 that store one or more software modules. Memories 301-2 and 304-2 may be implemented using any computer-readable storage medium, such as hard drives, CDs, DVDs, flash memory, RAM, ROM, etc. Memory 301-2 may store a module 301-3, which may be executed by processor 301-1. Similarly, memory 304-2 may store a module 304-3, which may be executed by processor 304-1.

Electronic device 19 may further comprise one or more UIs. The UI may allow one or more interfaces to present information to a user 8, such as a plan or intervention. The UI may be web-based, such as a web page, or a stand-alone application. The UI also may be configured to accept information about a user 8, such as data inputs and user feedback. The user 8 may manually enter the information, or it may be entered automatically. In an example, the user 8 (or the user's caretaker) may enter information such as when medication was taken or what food and drink the user 8 consumed. Electronic device 19 also may include testing equipment (not shown) or an interface for receiving information from testing equipment. Testing equipment may include, for example, a blood glucose meter, glucose meter, heart rate monitor, weight scale, blood pressure cuff, or the like. The electronic device 19 also may include one or more sensors (not shown), such as a camera, microphone, or accelerometer, for collecting feedback from a user 8. In one example, the device may include a glucose meter for reading and automatically reporting the user's glucose levels.

Electronic device 19 also may include a presentation layer. The presentation layer may be a web browser, application, messaging interface (e.g., e-mail, instant message, SMS, etc.), etc. The electronic device 19 may present notifications, alerts, reading materials, references, guides, reminders, or suggestions to a user 8 via presentation layer. For example, the presentation layer may present articles that are determined to be relevant to the user 8, reminders to purchase medications, tutorials on topics (e.g., a tutorial on carbohydrates), testimonials from others with similar symptoms, and/or one or more goals (e.g., a carbohydrate counting goal). The presentation layer also may present information such as a tutorial (e.g., a user guide or instructional video) and/or enable communications between the healthcare provider, and the user 8, e.g., patient. The communications between the healthcare provider, and the user 8, e.g., patient, may be via electronic messaging (e.g., e-mail or SMS), voice, or real-time video. One or more of these items may be presented based on a treatment plan or an updated treatment plan, as described later. The presentation layer also may be used to receive feedback from a user.

The system 100 also may include one or more databases, such as a database 302. Database 302 may be implemented using any database technology known to one of ordinary skill in the art, such as relational database technology or object-oriented database technology. Database 302 may store data 302-1. Data 302-1 may include a knowledge base for making inferences, statistical models, and/or user information. Data 302-1, or portions thereof, may be alternatively or simultaneously stored in server 29 or electronic device 19.

System 100 can be used for a wide range of applications, including, for example, addressing a user's healthcare, maintaining a user's finances, and monitoring and tracking a user's nutrition and/or sleep. In some embodiments of system 100, any received data may be stored in the databases in an encrypted form to increase security of the data against unauthorized access and complying with HIPAA privacy, and/or other legal, healthcare, financial, or other regulations.

For any server or server systems 29 depicted in system 100, the server or server system may include one or more databases. In an example, databases may be any type of data store or recording medium that may be used to store any type of data. For example, database 302 may store data received by or processed by server 29 including information related to a user's treatment plan, including timings and dosages associated with each prescribed medication of a treatment plan. Database 302 also may store information related to the user 8 including their literacy level related to each of a plurality of prescribed medications.

Figure 3B:
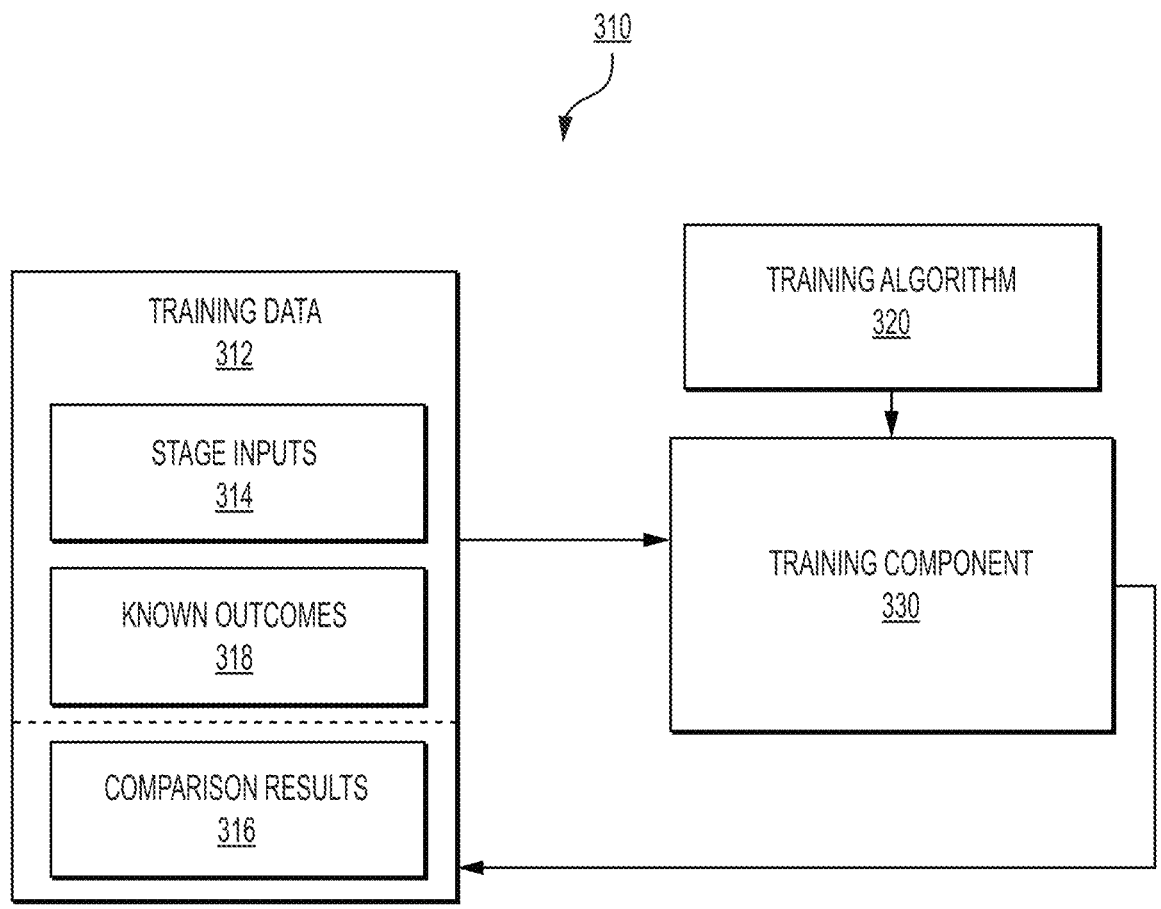
FIG. 3B shows a schematic illustration of training an exemplary machine learning model, in accordance with one or more embodiments.

As further disclosed herein, one or more components of the disclosed subject matter may be implemented using a machine learning model. FIG. 3B shows an example training module 310 to train one or more of the machine learning models disclosed herein. It will be understood that a different training module may be used to train each of the machine learning models disclosed herein and/or a single training module 310 may be used to train two or more machine learning models.

As shown in FIG. 3B, training data 312 may include one or more of stage inputs 314 and known outcomes 318 related to a machine learning model to be trained. The stage inputs 314 may be from any applicable source including a healthcare provider 7, one or more servers 29, electronic devices 19, EMR 14, an output from a step (e.g., one or more outputs from a step from flowchart 500 of FIG. 5 or flowchart 600 of FIG. 6, time in range (TIR) values, time above range (TAR) values, time below range (TBR) values, severity score, continuous glucose monitoring (CGM) classification, GRI values, engagement data, etc.). The known outcomes 318 may be included for machine learning models generated based on supervised or semi-supervised training. An unsupervised machine learning model may not be trained using known outcomes 318. Known outputs 318 may include known or desired outputs for future inputs similar to or in the same category as stage inputs 314 that do not have corresponding known outputs.

The training data 312 and a training algorithm 320 may be provided to a training component 330 that may apply the training data 312 to the training algorithm 320 to generate a machine learning model. According to an embodiment, the training component 330 may be provided comparison results 316 that compare a previous output of the corresponding machine learning model to apply the previous result to re-train the machine learning model. The comparison result 316 may be used by the training component 330 to update the corresponding machine learning model. The training algorithm 320 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, and/or discriminative models such as Decision Forests and maximum margin methods, or the like.

Health Conditions

Diabetes mellitus (commonly referred to as diabetes) may be a chronic, lifelong metabolic disease (or condition) in which a patient's body is unable to produce any or enough insulin, or is unable to use the insulin it does produce (insulin resistance), leading to elevated levels of glucose in the patient's blood. The three most identifiable types of diagnosed diabetes include: pre-diabetes, type 1 diabetes, and type 2 diabetes. Pre-diabetes is a condition in which blood sugar is high, but not high enough to be type 2 diabetes. Type 2 diabetes is a chronic condition that affects the way the body processes blood sugar. Lastly, type 1 diabetes is a chronic condition in which the pancreas produces little or no insulin.

Diabetes generally is diagnosed in several ways. Diagnosing diabetes may require repeated testing on multiple days to confirm the positive diagnosis of a types of diabetes. Some health parameters that doctors or other suitable healthcare providers use when confirming a diabetes diagnosis include glycated hemoglobin (A1C) levels in the blood, fasting plasma glucose (FPG) levels, oral glucose tolerance tests, and/or random plasma glucose tests. Commonly, a healthcare provider is interested in a patient's A1C level to assist in the diagnosis of diabetes. Glycated hemoglobin is a form of hemoglobin that is measured primarily to identify the three-month average plasma glucose concentration that may be used by doctors and/or other suitable healthcare providers include weight, age, nutritional intake, exercise activity, cholesterol levels, triglyceride levels, obesity, tobacco use, and family history.

Once a diagnosis of a type of diabetes is confirmed by a doctor or other suitable healthcare provider, the patient may undergo treatment to manage their diabetes. Patients having their diabetes tracked or monitored by a doctor or other healthcare provider may be treated by a combination of controlling their blood sugar through diet, exercise, oral medications, and/or insulin treatment. Regular screening for complications is also required for some patients. Depending on how long a patient has been diagnosed with diabetes, mHealth application 1 may suggest a specific treatment plan to manage their condition(s). Oral medications typically include pills taken by mouth to decrease the production of glucose by the liver and make muscle more sensitive to insulin. In other instances, where the diabetes is more severe, additional medication may be required for treating the patient's diabetes, including injections. An injection of basal insulin, also known as background insulin, may be used by healthcare providers to keep glucose levels at consistent levels during periods of fasting. When fasting, the patient's body steadily releases glucose into the blood to supply the cells with energy. An injection of basal insulin is therefore needed to keep glucose levels under control, and to allow the cells to take in glucose for energy. Basal insulin is usually taken once or twice a day depending on the type of insulin. Basal insulin acts over a relatively long period of time and therefore is considered long acting insulin or intermediate insulin. In contrast, a bolus insulin may be used to act quickly. For example, a bolus of insulin that may be specifically taken at meal times to keep glucose levels under control following a meal. In some instances, when a doctor or healthcare provider generates a treatment plan to manage a patient's diabetes, the doctor creates a basal-bolus dose regimen involving, e.g., taking a number of injections throughout the day. A basal-bolus regimen, which may include an injection at each meal, attempts to roughly emulate how a non-diabetic person's body delivers insulin. A basal-bolus regimen may be applicable to people with type 1 and type 2 diabetes. In addition to the basal-bolus regimen requiring injections of insulin, the treatment plan may be augmented with the use of prescribed oral medications. A patient's adherence to a treatment plan may be important in managing the disease state of the patient. In instances where the patient has been diagnosed with diabetes for more than six months, for example, a very specific treatment regimen must be followed by the patient to achieve healthy, or favorable, levels of glucose. Ultimately, weekly patterns of these medication types of treatments may be important in managing diabetes. mHealth application 1 may recommend treatment plans to help patients manage their diabetes.

Exemplary Methods

Diabetes is a chronic condition that results in a patient unable to keep glucose within a normal or recommended target range. Such fluctuating glucose levels (i.e., outside the normal or recommended target range) can lead to significant health complications. Developing meaningful insights and predictions for health and engagement outcomes is difficult with sporadic blood glucose monitoring (BGM), where only a handful of intermittent readings in a week may not serve a basis to understand patterns, and any underlying causes for those patterns (e.g., determining a rising BGM based on a meal type). A similar issue may exist with respect to flash glucose monitoring (FGM), in that readings are sporadic and non-regular or continuous.

Continuous glucose monitoring (CGM) provides the possibility for dense data (e.g., data based on a collection frequency of every 5 minutes or less) to be automatically gathered through wearable sensors (e.g., sub-cutaneous sensors) that provide a periodic glucose value (e.g., a user 8's glucose levels). CGM can improve diabetes care by providing a continuous (e.g., approximately every five minutes or less) or semi-continuous (e.g., more than approximately every five minutes) readout of glucose data to user 8 or other entities (e.g., healthcare provider 7) so that the user 8 or other entities can be more aware of the user 8's glucose levels at all times of the day. Such data may allow a machine learning model to be trained to predict future health and engagement levels and outcomes based on inputs of glucose levels and engagement data.

A CGM monitor may be a continuous analyte sensor system that includes any sensor configuration that provides an output signal indicative of a concentration of an analyte. The CGM monitor may sense the concentration of the analyte to determine, for example, glucose values, based on a bodily fluid (e.g., interstitial fluid). The bodily fluid may be accessed through a user's skin. The output signal, which may be in the form of, for example, sensor data, such as a raw data stream, filtered data, smoothed data, and/or otherwise transformed sensor data, may be sent to a receiver, which may be connected to the CGM monitor via a wired or wireless connection and may be local or remote from the sensor. According to embodiments, the CGM monitor may include a transcutaneous glucose sensor, a subcutaneous glucose sensor, a continuous refillable subcutaneous glucose sensor, a continuous intravascular glucose sensor, or the like. The CGM monitor may be a compact medical system with one or more sensors that is inserted onto a user 8's abdomen and that includes a small cannula that penetrates the user 8's skin. An adhesive patch may hold the monitor in place. The sensor may sense glucose readings in interstitial fluid on a continuous or semi-continuous basis.

A transmitter may be connected to the sensor to allow the CGM monitor to send the glucose readings wirelessly to a monitoring device. The monitoring device may be a CGM monitor specific monitoring device, may be a third party device, an electronic device 19, or any other applicable device. The monitoring device may be a dedicated monitoring device or an electronic device 19 that provides one or more functions in addition to the CGM monitoring. An application or other software may be used to facilitate the analysis and/or display of the glucose readings and associated data via the monitoring device. The monitoring device may be used to analyze and/or view the data associated with the glucose readings. Alternatively, or in addition, the CGM monitor may include a display to view glucose readings and/or associated data. The CGM monitor and/or external device may be configured to generate and/or provide alerts based on the glucose data (e.g., if blood sugar levels are too high or too low, or showing an unfavorable trend).

By using CGM data, a time in range (TIR) value can be determined where a TIR value is based on an amount of time a user 8's glucose level is within a threshold band over a base time period. The threshold band may be pre-determined, be user specific, or may be dynamically determined.

The threshold band may be a pre-determined value based on, for example, a cohort of patients. The lifestyle, habits, medical test results for each of the patients in a cohort may be used to determine the pre-determined value. For example, one or more cohorts of patients may be determined based on the patient's lifestyle, habits, demographics, or the like, and a threshold band may be generated for each of the one or more cohorts. The threshold band may be determined based on optimal results (e.g., preferred A1C values) based on an analysis of glucose levels over a period of time.

A GRI value may be determined using CGM data where a GRI value may be a composite metric from CGM tracings that may be indicative of a quality of glycemia for a user 8 and may assist with basic clinical interpretation of CGM data. A "quality of glycemia" may be characterized by proportions of time with both low/very low, and high/very high glucose concentrations. A GRI value is based on a hypoglycemia component and a hyperglycemia component. The hypoglycemia component may be associated with an amount of time a user 8 was hypoglycemic during a specified time period and the hyperglycemia component may be associated with an amount of time the user 8 was hyperglycemic during the specified time period.

The following equations may be used to determine a GRI value. In the following equations, "VLow" represents a percentage of time a user experiences very low-glucose hypoglycemia and "Low" represents a percentage of time a user experiences low-glucose hypoglycemia. "VHigh" represents a percentage of time a user experiences very high-glucose hyperglycemia and "High" represents a percentage of time a user experiences high-glucose hyperglycemia. "HypoComponent" represents a hypoglycemia component while "HyperComponent" represents a hyperglycemia component.

$$\text{Hypoglycemia Component} = VLow + (0.8 \times Low)$$

$$\text{Hyperglycemia Component} = VHigh + (0.5 \times High)$$

$$GRI = (3.0 \times HypoComponent) + (1.6 \times HyperComponent)$$

Another equivalent equation for GRI includes:

$$GRI = (3.0 \times VLow) + (2.4 \times Low) + (1.6 \times VHigh) + (0.8 \times High)$$

Figure 4:
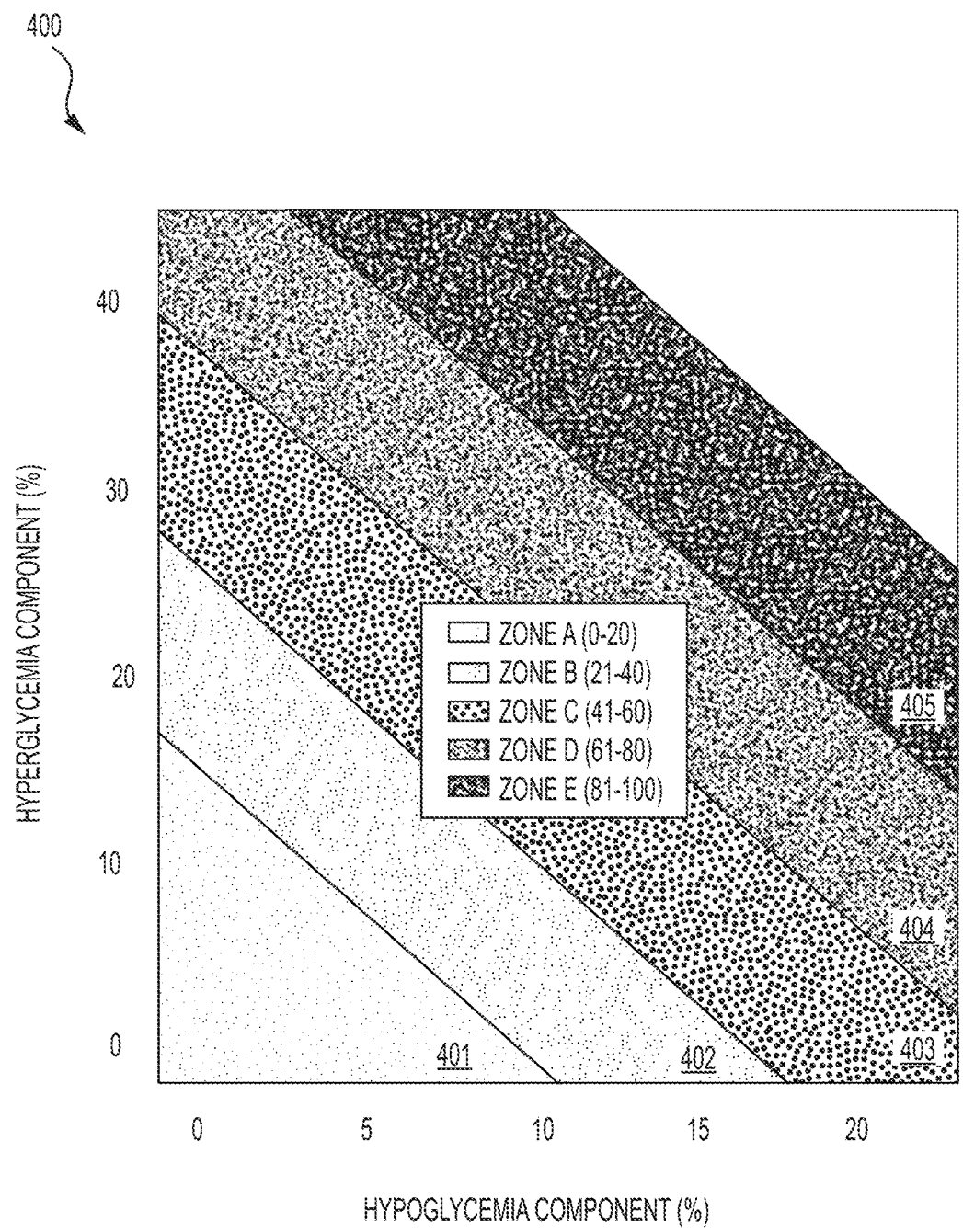
FIG. 4 shows a plot depicting GRI zones, in accordance with one or more embodiments.

FIG. 4 shows a plot 400 depicting five GRI zones, in accordance with one or more embodiments. Because glycemic control is a two-dimensional quality, the GRI's hypoglycemia and hyperglycemia components may be displayed on a two-dimensional plot, as shown in plot 400. In plot 400, the hypoglycemia component is displayed on the horizontal axis and the hyperglycemia component is displayed on the vertical axis. However, it will be understood that the hypoglycemia component and/or hyperglycemia component may be visualized in any applicable manner. A set of diagonal lines divides plot 400 into 5 glycemia risk zones, labeled 401, 402, 403, 404, and 405. Each of these zones corresponds to a quintile for overall quality of glycemia ranging from the best (0-20$^{th}$ percentile, zone A 401) to the worst (81$^{st}$ to 100$^{th}$ percentile, zone E 405). Users with diabetes may receive a GRI score for a given time period and the score may be mapped to one of the five GRI zones. Additional information related to a composite metric for the quality of glycemia from CGM for assisting with basic clinical interpretation of CGM data is provided in Klonoff et al (Klonoff D C, Wang J, Rodbard D et al. A glycemia risk index (GRI) of hypoglycemia and hyperglycemia for continuous glucose monitoring validated by clinician ratings. J Diabetes Sci Technol. 2022 Mar. 29), which is incorporated herein by reference.

Figure 5:
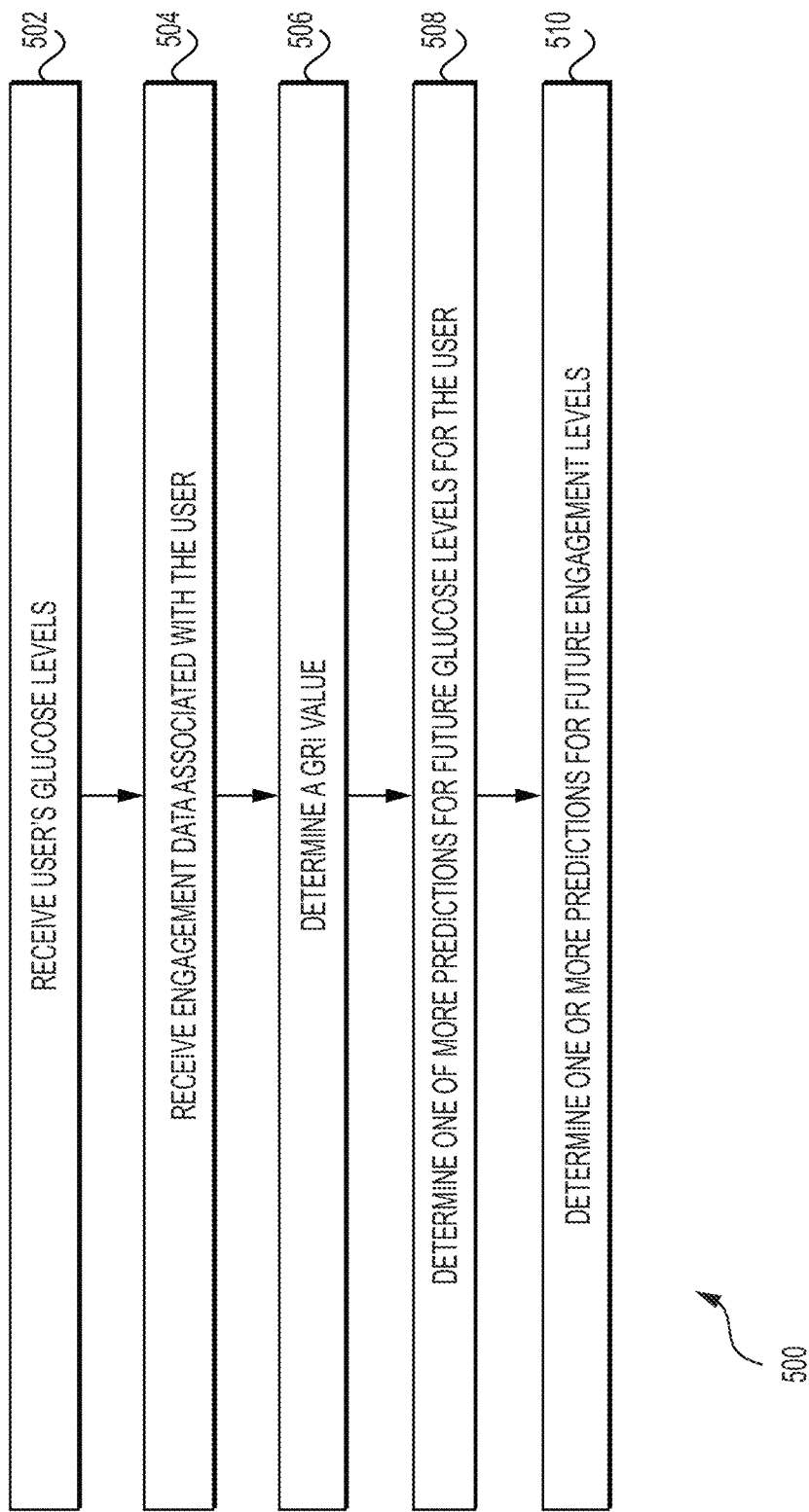
FIG. 5 shows a flowchart for determining one or more predictions for future glucose and engagement levels, in accordance with one or more embodiments.

FIG. 5 shows a flowchart 500 for determining one or more predictions for future glucose and engagement levels, according to one or more embodiments. As used herein, an engagement level may correspond to a level of input or interaction of a user associated with medical, diet, exercise, etc. compliance. At 502, a user 8's blood glucose levels may be received. The blood glucose levels may be provided on a continuous or semi-continuous basis by a CGM monitor, as disclosed herein. The blood glucose levels may also be provided by a standard blood glucose monitor (BGM), by a flash glucose monitor (FGM), or a combination of CGM, BGM, and/or FGM. The blood glucose levels may be received at a component of the CGM monitor itself or may be received at a local or remote component such as an electronic device 19, mHealth application 1, one or more servers 29, or the like. The blood glucose levels may be provided automatically from the CGM monitor to one or more components, may be pushed upon collection of blood glucose levels, or the CGM monitor may be pinged to transmit one or more collected blood glucose levels.

As an example, a user 8 may attach a CGM monitor to her body and the CGM monitor may collect blood glucose level readings approximately every five minutes. The CGM monitor may be connected to the user 8's mobile device (e.g., via a network connection, local area network connection, wide area network connection, WiFi connection, Bluetooth® connection, etc.). According to a first example embodiment, the CGM monitor may automatically transmit a blood glucose level reading to user 8's mobile device each time a reading is collected (e.g., every 5 minutes). Alternatively, or in addition, the CGM monitor may store one or more blood glucose level readings such that they are sent to the user 8's mobile device as a group of multiple readings and/or when the user 8's mobile device or another component requests that the one or more blood glucose level readings are transmitted.

At 504 of FIG. 5, engagement data associated with the user may be received. The engagement data may be collected over a predefined period time (e.g., the same time period for glucose levels collection at step 502) by a computing device, such as electronic device 19. The engagement data may include and/or be associated with user 8's medication intake, diet, physical activity, laboratory results, and/or education activity (e.g., "MEDAL" activities), which are each discussed herein in more detail. The engagement data may also include CGM engagement associated with user 8. CGM engagement may include blood glucose activity which may be collected using a CGM device.

In some cases, engagement data may be collected via user input through an application such as mHealth application 1. For example, user 8 may record, using mHealth application 1, each time any medication is taken by user 8. User 8 may record the time and date of the medication intake as well as the medication name, type, and/or dosage. User 8 may also record a medical intake technique such as whether the medication was taken orally or via some other method of intake (e.g., by injection, inhalation, topical application, etc.). User 8 may record reasons for taking the medication, such as to treat pain or other symptoms. User 8 may further record whether the medication alleviated any of the symptoms, and may further record any side effects that may be experienced from taking the particular medication.

As another example, user 8 may receive a prompt via mHealth application 1 to take a particular medication at a particular time. mHealth application 1 may send a push notification at a prescribed time of medication to remind the user to take the medication. In some cases, mHealth application 1 may prompt user 8 ahead of time (e.g., one hour in advance) to remind user 8 to take a particular medication at a particular time. Following the prompt (e.g., the push notification) to take a medication, mHealth application 1 may follow up requesting input from user 8 that the medication was actually taken. This may be done through a user interface on electronic device 19 via mHealth application 1 that asks for a confirmation of medication intake. In some instances, there may be no prescribed time to take a particular medication and user 8 may not receive a prompt to take a particular mediation. In these instances, user 8 may access mHealth application 1 to enter details about medication intake on a regular basis (e.g., once a week, once a day, multiple times a day).

Medication intake may, in some embodiments, refer to insulin delivery. As discussed herein, insulin delivery may refer to an injection of basal insulin or a bolus of insulin to help the user's body regulate blood sugar levels (i.e., glucose levels). In some cases, user 8 manually performs insulin delivery using a syringe, an insulin pen, an insulin pump, or an insulin inhaler. User 8 may manually calculate and determine when basal and bolus doses are to be administered via any one of these methods. User 8 may also use mHealth application 1 for reminders and calculations regarding the timing and dosage amount of insulin. A combination of manual calculations and automatic reminders and calculations may be employed. For example, a user may receive automatic regular (e.g., hourly) basal doses of insulin via an insulin pump but may need to manually calculate the amount of bolus insulin to administer (often via the same insulin pump) at mealtimes. CGM may be used along with an insulin pump to act as an "artificial pancreas" where a CGM device monitors the blood glucose levels and the basal or bolus dose is determined based on current and predicted glucose levels. As the CGM device and insulin pump work together to administer insulin to user 8, a record of the time, dosage amount, glucose level, and type of insulin for each dose may be stored for future analysis by user 8 or user 8's physician.

Other devices and sensor may be used to measure and record user 8's medication intake. For example, user 8 may place a quantity of pills in a pillbox or pill dispenser, which may be connected to electronic device 19 and/or network 32. The pill dispenser may include one or more sensors to automatically monitor whether the pills (e.g., pills for a particular day) have been removed from the pill dispenser, which may indicate that the medication was taken by user 8. For example, the pill dispenser may include a weight sensor that can sense minute differences in weight and may determine whether a pill is still in the compartment or has been retrieved. The pill dispenser may also include a light sensor that may be blocked by one or more pills, indicating that the pills are still present. There may also be a light that is regularly illuminated and if a full amount of light is received by the light sensor, the pill dispenser may determine that the pills are gone, because one or more pills would block at least some of the light. The light sensor may also determine a color of the pills by measuring the wavelength of any reflected light from the pills. A camera may be used to distinguish shapes and colors of pills which may determine which pills are present and which have been taken. The pill dispenser may also include an automatic dispenser that is programmed to dispense a pill whenever user 8 is supposed to take it. The pill dispenser may keep track of when pills are to be dispensed and may automatically dispense them for user 8. The pill dispenser may keep records of when pills are taken and may transmit these records to electronic device 19 for analysis.

Diet for user 8 may be tracked with user input via mHealth application 1. User 8 may input food eaten during and between meals into mHealth application 1. In some cases, user 8 calculates some or all nutritional information including number of calories, fat content, sugar content, etc. In other cases, mHealth application 1 estimates nutritional information based on a database of foods that includes nutritional information. mHealth application 1 may prompt user 8 at specified times during the day with reminders to record diet information. In one or more embodiments, mHealth application 1 may interact with a CGM device to determine that user 8 has eaten. If glucose levels rise above a threshold or rise at a rate that is above a threshold rate, mHealth application 1 and/or the CGM device may determine that user 8 has eaten. Based on this rise in glucose levels, mHealth application 1 may provide a prompt to user 8 to record diet information. In one or more embodiments, a user may take and provide a photograph of any food before it is eaten as an input for mHealth application 1.

According to an embodiment, mHealth application 1 may use food intake machine learning to determine what the food is and its nutritional details. The food intake machine learning model may be trained using historical or simulated food items and their respective nutritional details. Based on the training, the food intake machine learning model may generate nutritional details based on food intake information such as type of food, type of preparation, ingredients, quantities, and/or the like.

As with medication intake or diet, physical activity may be recorded manually by user 8 via mHealth application 1. Following any kind of physical activity (e.g., workout or exercise), user 8 may record the activity, including the type of activity, the intensity of the activity, feelings and mood before, during, and after the activity, and/or any other notes including unexpected difficulties. User 8 may also record details of the workout related to the particular physical activity. For example, if the activity was a run, user 8 may record the distance covered, time running, percentage of walking during the run, etc.

Physical activity may be collected and recorded automatically via one or more activity trackers (e.g. a smart watch, a smart ring, an activity band, a smart phone, etc.) that utilize one or more sensors to measure one or more metrics related to physical activity. For example, an activity tracker may track a user's steps, elevation gain/loss, heart rate, temperature, etc. The activity tracker may include one or more electronic sensors including an accelerometer, a gyroscope, an altimeter, a photoplethysmography (PPG) sensor, a pulse oximeter sensor (e.g., SpO2 monitor), a bioimpedance sensor (e.g., one or more electrodes or EKG/ECG sensors), an electrodermal activity sensor, a GPS sensor, a light/optical sensor, a compass, a UV sensor, a magnetometer, a gesture sensor, a temperature sensor, a microphone, and/or a skin conductance sensor. One or more of these sensors may work independently or in combination to detect motion, movement, acceleration, elevation, heart rate and/or other heart activity, blood oxygen level, direction, location, orientation and rotation of the device, etc. Raw electronic data may be obtained from these one or more electronic sensors and may be analyzed and synthesized to obtain useful metrics for determining and analyzing physical activity. For example, data related to motion or acceleration may be used to determine a number of steps, the intensity of the steps (e.g., whether the user was walking, jogging, or sprinting). Data related to elevation may be aggregated to the motion data to obtain inferences such as a number of stairs ascended or descended, or distance and elevation gain during a hike.

Other health-related data may be collected, either through user input or automatically via connected electronic devices including, for example, blood pressure and weight. For example, blood pressure may be a useful metric to provide information regarding a user's cardiovascular system and may be measured using an inflatable blood pressure cuff, either manually or automatically. If using a standard blood pressure cuff with manual reading of blood pressure, user 8 may enter the blood pressure in a user interface associated with mHealth application 1. An electronic blood pressure monitor device may measure blood pressure and transmit the value to the mHealth application 1 for storage and analysis. Other methods of measuring blood pressure may include arterial tonometry and oscillometric blood pressure measurement. Similarly, weight of a user may be measured using a standard (e.g., non-electronic) scale with results manually input by user 8 in mHealth application 1. Weight may also be measured using an electronic scale (a "smart scale") that is connected to electronic devices 19 or network 32. Measured weights may be automatically transmitted to mHealth application 1.

Results from lab test or other medical examinations may be collected via user input in mHealth application 1, or by automatic transmission via network 32 directly from the laboratory where lab tests are conducted or the hospital or clinic where the medical examination is conducted. Lab tests or other medical examinations may include A1C tests, lipid profile tests, kidney function tests (e.g., urine albumin tests), eye examinations, foot examinations, liver function tests, thyroid function tests, C-peptide tests, and/or hemoglobin tests.

Education activity may include any activities that a user completes to learn about their condition, management of the condition, and how to prevent or manage complications. By way of example, education activity related to diabetes may take many forms including one-on-one counseling with a healthcare provider or diabetes instructor, group classes or support groups, online resources and apps, and written or audio/visual materials. Diabetes education may cover a variety of topics including understanding the causes and symptoms of diabetes, how to monitor blood sugar levels and interpret the results, the role of medication and insulin therapy in diabetes management, how to manage diet and nutrition to control blood sugar levels, the importance of physical activity and exercise in diabetes management, strategies for preventing or managing diabetes-related complications, such as nerve damage, kidney disease, and vision problems, and tips for coping with the emotional and psychological challenges of living with diabetes.

Education activities may be facilitated via mHealth application 1. For example, user 8 may engage with mHealth application 1 by opening an article about the role of medication and insulin therapy in diabetes management. Another example may include counseling with a healthcare provider or diabetes instructor via mHealth application 1, which may include a videoconference. Engagements with mHealth application 1 such as opening and reading articles or participating in a videoconference with an instructor or provider may be logged and recorded as a completed education activity. User 8 may also manually input in mHealth application 1 completed education activities not facilitated by mHealth application 1.

Engagement data related to medication intake, diet, physical activity, lab results, and education activity (e.g., "MEDAL" data), as discussed above, may be aggregated and synthesized to generate an engagement score (e.g., engagement state) of user 8 over a predefined time period. Engagement, as discussed herein, refers to engagement with mHealth application 1 by manually inputting data into mHealth application 1, by directly interacting with mHealth application 1, and/or by engaging with one or more entities that transmit data to mHealth application 1 on behalf of a user (e.g., automated engagement). For example, the one or more entities may include a laboratory, a support group, a device, a platform, an activity tracker, a pill dispenser, an online calorie tracker, etc. Engagement data, therefore, refers to any data indicating engagement with mHealth application 1, such as manual user inputs from user 8 in mHealth application 1, automated inputs (e.g., using one or more electronic devices 19), received transmissions from third-party sources that received any interaction with user 8 regarding medication intake, diet, physical activity, lab results, and education activity.

In some embodiments, an engagement state may be binary and may be classified as either a high engagement state or a low engagement state. An engagement state may be classified as a high engagement state if user 8 engages with mHealth application 1 or an entity that transmits data to mHealth application 1 at or above a threshold amount. An engagement state may be classified as a low engagement state if user 8 engages with mHealth application 1 or an entity that transmits data to mHealth application 1 below the threshold amount. In some embodiments, an engagement state may be determined based on the number of "engagement activities" that user 8 participates in over a period of time. An engagement activity may be a single activity or interaction with application 1 or an entity that transmits data to mHealth application 1 on behalf of user 8. For example, an engagement activity may include a single user input or entry in mHealth application 1 of a medication taken, a meal and its nutritional information, a workout, lab test results, and/or an education activity. As further examples, an engagement activity may include a transmission received by mHealth application 1 from an activity tracker regarding activity for user 8, from a network-connected pill dispenser, from a third-party lab with lab test results, and/or from a network-connected educational website. According to an embodiment, any time user 8 interacts with mHealth application 1 may be an engagement activity. Any educational activity facilitated via mHealth application 1 or other applicable platform may be recorded as an engagement activity.

By way of example of binary engagement states, a threshold for high engagement may be approximately five engagement activities over a period of ten days. Using this example threshold, if user 8 performs approximately five or more engagement activities during a ten day period, then it may be determined that user 8's engagement state is a "high engagement state." If user 8 performs less than approximately five or more engagement activities over the ten day period, then the engagement state may be determined to be a "low engagement state."

There may be more than two engagement states. In one example, there may be three engagement states including a "high engagement state," a "low engagement state," and a "no engagement state." In this example, the high engagement and low engagement states may be the same as for the example above with two engagement states. The difference may be that the no engagement state is registered whenever the number of engagement activities during the time period is zero. There may be a scale of engagement such that instead of a discrete number of engagement states, the number of engagement activities is stored and used for analysis and predictions. Furthermore, in some embodiments, engagement activities may have different weights such that some engagement activities count for a greater level of engagement while others count for a lower level of engagement. The weights of each engagement activity may be accounted for when determining an engagement state.

Engagement data received at 504 may also include a measure of CGM device usage by user 8 ("CGM engagement"). For example, if user 8 continuously uses (e.g., wears) a CGM device day and night, with minimal gaps to switch out a sensor, the received engagement data may indicate a high CGM engagement. In some embodiments, a state of CGM engagement is determined based on a threshold number of CGM readings collected. For example, if user 8's CGM device recorded approximately 70% or more of possible CGM readings during the time period, the CGM engagement state may be classified as a "high engagement state." If user 8's CGM device recorded less than approximately 70% of possible CGM readings during the time period, the CGM engagement state may be classified as a "low engagement state." The number of possible CGM readings in a time period may be approximately 288 readings per day (e.g., one reading approximately every five minutes), and may refer to a frequency at which a CGM device is configured to take a reading of a blood glucose level.

At 506 of FIG. 5, a GRI value may be determined based on hypoglycemia component and a hyperglycemia component according to one or more techniques disclosed herein. The hypoglycemia component may be associated with the amount of time user 8 was hypoglycemic during a time period (e.g., the time period for collecting glucose and engagement levels at steps 502 and 504 respectively). The hyperglycemia component is associated with the amount of time user 8 was hyperglycemic during the same time period. A GRI zone may also be determined based on the GRI value and the hypoglycemia and hyperglycemia components.

In some embodiments, time in range (TIR) values associated with the blood glucose level readings are determined. In-range blood glucose values may correspond to the amount of time blood glucose level readings are within a given range, ratio of blood glucose level readings within range to out of range, count of blood glucose level readings in range to out of range, or the like. For example, TIR values may be based on blood glucose level readings that are between approximately 70 mg/dl and approximately 180 mg/dL. The TIR values may distinguish the user 8's blood glucose levels from the times when they are within the range to the times when they are outside of the range. The determined TIR value may be based on an amount of time user 8's blood glucose level is within a threshold band over a base period of time. The base period of time may be a single 24-hour day or may be a different base period. The base period may be pre-determined (e.g., by user 8, by a healthcare provider 7, pre-programmed, etc.), or may be dynamically determined based on one or more factors. The one or more factors may be patient vectors, patient attributes, a current or previous TIR state, or the like.

According to an embodiment, the TIR value may be for the base period or may be a TIR value associated with the patient over a number of base periods. For example, a TIR value for user 8 may be determined for each day for a total of ten days. The TIR value from each of the ten days may be combined using any applicable technique (e.g., an average) such that the TIR associated with the user 8 over the ten days is the combined TIR value.

At 508 of FIG. 5, one or more predictions for future glucose levels are determined based on user 8's glucose levels and engagement data received at steps 502 and 504. The one or more predictions may be based on user 8's glucose levels and engagement data over a given period of time (e.g., ten days), which may be considered an initial period of time. The one or more predictions may be determined using a machine learning model trained to determine predictions of glucose and/or engagement levels, in accordance with one or more techniques disclosed herein. A prediction may be an estimated or calculated value based on current or historical values (e.g., values determined during the initial period).

Predicted values may include quantitative measurements, such as blood glucose levels, or qualitative metrics derived from the quantitative measurements, such as GRI values. Accordingly, the one or more predictions may include a prediction of one or more future GRI values. A future GRI value may be predicted based on current and historical received and/or determined GRI values. Further, it may be determined whether a future GRI value is greater than or less than the first GRI value determined at step 506. A future GRI zone may also be determined based on the future GRI value. The future GRI zone may be compared to the current determined GRI zone and it may be determined whether the future GRI zone is the same as, or is different from the current determined GRI zone.

In some embodiments, predictions regarding user 8's future glucose levels are based on both the user's current and historical glucose levels and engagement levels. In other embodiments, predictions regarding user 8's future glucose levels are based only on the user's current and historical glucose levels without regard to engagement levels.

The one or more predictions for future glucose levels of step 508 may also include predictions for one or more future TIR values. The predictions may include a prediction of whether a future TIR value is greater than or less than the determined current or historical TIR value responsive to a comparison between the current/historical TIR value and the predicted future TIR value. In some embodiments, the predictions regarding a future TIR value include a prediction of whether the future TIR value is within a certain percentage of the current determined TIR value, or is greater by more or less by more than the certain percentage. For example, it may be predicted that a future TIR value will be within approximately 5% of the current determined or historic TIR value, greater by more than approximately 5%, or less by more than approximately 5%.

At 510 of FIG. 5, one or more predictions for future engagement levels (e.g., future MEDAL levels) are determined based on received engagement levels that were collected over a period of time. According to an embodiment, one or more predictions for future engagement levels may be based on received glucose levels collected over the period of time. The one or more predictions for future engagement levels may be determined using a trained machine learning model trained to take current and/or historical engagement levels and output a prediction for future engagement levels. In some embodiments, the predictions for future engagement levels may be based on current and historical values of glucose levels and engagement levels, or in some cases may be based only on current and historical values of engagement levels, or only on current and historical values of glucose levels. A prediction for future engagement levels may include a prediction of a future engagement state. For example, a predicted future engagement state may be a high engagement state, a low engagement state, no engagement state, an engagement state value or tier, etc. Further, a future predicted engagement state may be compared to the current received or determined engagement state to determine whether the states are different or the same. A prediction for future engagement levels may include predictions for how user 8 may interact and/or engage with mHealth application 1, tracking devices, and/or the like as discussed herein. For example, a machine learning model may receive input engagement data reflecting that user 8 engaged with mHealth application 1 in specific ways (e.g., MEDAL values), and make predictions on how user 8 will engage with mHealth application 1, tracking devices, etc., such as how will user 8 engage with certain foods, certain medications, certain exercise routines, etc.

Future engagement level predictions may also include one or more predictions for future CGM engagement. For example, if user 8's CGM engagement was classified as a high engagement state during the time period of engagement data collection, it may be predicted that user 8 will continue to exhibit high engagement or usage of a CGM device, or additionally based on other factors, that user 8 will in the future exhibit a low engagement state.

One or more sets of features may be derived from the user's glucose levels and/or the engagement data, according to one or more embodiments of the present disclosure. More details regarding features derived from CGM data and engagement data is disclosed herein with respect to FIGS. 8A-8D. The derived set(s) of features may be provided as inputs to the machine learning model to determine the predictions for future glucose levels and future engagement levels. For example, a machine learning model may be trained to extract derived features based on glucose levels and/or engagement data and/or make feature based predictions based on the derived features.

Figure 6:
FIG. 6 shows a flowchart for training a machine learning model for predicting health and engagement outcomes, in accordance with one or more embodiments.

FIG. 6 shows a flowchart 600 of training a machine learning model for predicting health and engagement levels for a user, according to one or more embodiments. At 602, a first set of glucose levels collected by a CGM device over a first time period are received. In one or more embodiments, two or more first sets of glucose levels is received. For example, a first set of glucose levels may be received for multiple users including user 8. The two or more first sets of glucose levels may also refer to multiple iterations of collecting glucose levels for the same user (e.g., user 8) over multiple fixed time periods. According to an embodiment, the glucose levels received at 602 may be simulated (e.g., using a simulation model configured to output representative glucose levels).

At 604, a second set of glucose levels collected by the CGM device over a second time period are received. The second time period may be subsequent to the first time period and may be the same length of time as the first time period or a different length of time than the first time period. In one or more embodiments, two or more second sets of glucose levels are received, where each set of glucose levels are associated with the same user (e.g., user 8) or, in some cases, a different user. Each first set of glucose levels and each second set of glucose levels corresponding to the same user may be correlated so patterns and relationships between the two may be analyzed and determined.

According to an embodiment, the CGM device used to collect the glucose levels during the first time period and the CGM device used to collect the glucose levels during the second time period may be the same. According to another embodiment, the CGM device used to collect the glucose levels during the first time period and the CGM device used to collect the glucose levels during the second time period may be different. According to this embodiment, differences in CGM devices may be accounted for during training of a machine learning model. For example, the machine learning model may be provided technical information (e.g., drift values, calibration metrics, etc.) associated with each CGM device and may be configured to normalize the CGM values output by each respective CGM device. The first and second set of glucose levels may include the same or substantially similar number of glucose level measurements, but in some cases, the first and second set of glucose levels may include a different amount of glucose level measurements.

At 606, a first set of engagement data is received. In some embodiments, two or more first sets of engagement data are received, where each set is associated with one user (e.g., user 8). Additional sets may be associated with multiple different users or may be engagement data collected multiple times for the same user over multiple fixed time periods. The first set of engagement data is collected by a computing device (e.g., electronic device 19) over the first time period. The first time period over which the first set of engagement data is collected may correspond to the first time period over which the first set of glucose levels were collected (e.g., an initial time period).

At 608, a second set of second engagement data is received. In some embodiments, two or more second sets of engagement data are received, where each set is associated with one user (e.g., user 8). Additional sets may be associated with multiple different users or may be engagement data collected multiple times for the same user over multiple fixed time periods. The second set of engagement data is collected by a computing device (e.g., electronic device 19) over a second time period. The second time period over which the second set of engagement data is collected may correspond to the second time period over which the second set of glucose levels were collected. Both the first and the second sets of engagement data may be associated with one or more of the user's medication intake, diet, physical activity, laboratory results, and education activity (e.g., MEDAL activity).

At 610, one or more machine learning models (e.g., a glucose and engagement machine learning model) is trained based on a machine learning algorithm. A machine learning model may be trained using training data which includes the first glucose levels received at step 602, second glucose levels received at step 604, the first engagement data received at step 606, and second engagement data received at step 608.

According to an embodiment, a first machine learning model may be trained specifically for users with type 1 diabetes and a second machine learning model may be trained specifically for users with type 2 diabetes. In some cases, a single machine learning model may be trained for all users with diabetes, regardless of the type.

Sets of features may be derived from the first set of glucose levels received at step 602 and the first engagement data received at step 606. In some cases, features may be derived from the second set of glucose levels received at step 604 and the second engagement data received at step 608. The derived features may be included as a part of the training data or may be determined by the one or more machine learning models based on the input training data from steps 602-608.

According to an embodiment, before being input as training data, the data received at steps 602-608 may be cleaned. Cleaning the data includes identifying and correcting or removing any errors, inconsistencies, or irrelevant information from the dataset. Missing data may be handled by identifying any missing values in the dataset and determining data modifications, including removing a row or column with the missing value, replacing the missing value with an estimate, or using a machine learning algorithm to impute the missing values. Duplicates are removed to avoid skewed results. Data may be standardized if received from multiple different sources, which includes converting the data to a consistent format and/or unit. Outliers (e.g., extreme values that may significantly affect the training) may be modified (e.g., removed or corrected). The data received at steps 602-608 may be examined for human or technical errors and corrected if such errors are identified. Irrelevant data may be removed to target the training on data that is most relevant and important for predicting future health and engagement outcomes.

Relevant features are identified and selected, as discussed herein. According to an embodiment, relevant features may include those that are most important in predicting future health and engagement outcomes (e.g., glucose levels and engagement levels). Irrelevant and/or redundant features may negatively affect the performance of the machine learning model and may increase its complexity, and may be removed. Selecting relevant features may involve exploratory data analysis, correlation analysis, feature importance ranking, and domain knowledge.

Exploratory data analysis may include visualizing the training data and analyzing relationships between different variables, which may be used to identify the features that are highly correlated with the target variable, along with those with a weak relationship. Correlation analysis may involve calculating the correlation coefficient between each feature and the target variable. Features with a high correlation coefficient may be more relevant than those with a low correlation coefficient. Feature importance ranking includes using statistical algorithms such as decision trees or Random Forests to rank the importance of each feature based on their contribution to the accuracy of the model. Domain knowledge may be used to identify relevant features that are not captured by statistical methods. For example, in the present disclosure, it may be known by those in the art that food and medication features are the most relevant for glucose level predictions while comment features (e.g., user input comments in mHealth application 1) and education activity features are not as relevant, and therefore may only add to the complexity of the model, decreasing it usefulness. Once the most relevant features are selected, the training dataset may be transformed to include only those features that are ranked as most important for the model. This reduces the complexity of the model, reduces the risk of overfitting, and improves the overall accuracy of the model in making predictions. In some embodiments, feature selection may be automatic and the most relevant features are selected without manual intervention.

According to an embodiment, any applicable features may be identified such that relevant features are not extracted. Accordingly, such features may include known relevant features as well as features not known to be relevant. The one or more machine learning models may be trained to apply all or a subset of such features based on their applicable weights, layers, biases, synapses, training algorithm and/or the like. According to this embodiment, the one or more machine learning models may be provided or may determine any such applicable features for training or for generating predictive outputs.

According to embodiments disclosed herein, features may be determined based on any applicable attribute such as a category, variance, segment, or the like associated with given data. Such attributes may be based on, but are not limited to, a time or time range (e.g., time of day, hour, day, etc.), type of data (e.g., CGM data, MEDAL data, TIR data, TBR data, GRI data, glucose management indicator (GMI) data, etc.), type of analysis associated with data (e.g., mean, sum, value, etc.), and/or the like.

The model is trained using the training dataset, in accordance with one or more techniques of the present disclosure, including those discussed with respect to FIG. 3B. Training includes using statistical algorithms to find patterns and relationships (e.g., associations, correlations, dependencies, connections, similarities, etc.) in the data that can be used to make predictions. For example, the model is trained with inputs including the first and second sets of glucose levels and the first and second sets of engagement data as discussed in reference to steps 602-608. The model may be trained to, using statistical algorithms, determine patterns and relationships between the first set of glucose levels received at step 602 and the second set of glucose levels received at step 604. Alternatively, or in addition, the model may be trained to determine patterns and relationships between the first set of engagement data received at step 606 and the second set of engagement data received at step 608.

At 612, one or more patterns in the training data are determined. For example, the model may be trained to determine patterns and relationships between the first sets of glucose levels and engagement data and the second sets of glucose levels and engagement data. Determining patterns in the training data may include determining a relationship between the first set of glucose levels received at step 602 and the second set of glucose levels received at step 604. Determining patterns may also include determining a relationship between the first set of engagement data received at step 606 and the second set of engagement data received at step 608. Weights, layers, biases, and/or synapses associated with the machine learning model may be updated based on the determined patterns. Further, testing data may be provided to the machine learning model to determine its accuracy, and the model may be retrained, updated, or tuned based on the results of one or more of the accuracy tests.

In one or more embodiments, as disclosed herein, the machine learning model trained based on the method provided in flowchart 600 may be implemented to make one or more predictions for a new set of unseen data. For example, a third set of glucose levels may be received, where the third set of glucose levels are collected by a CGM device over a third time period that is subsequent to the second time period. A third set of engagement data may also be received, as collected by a computing device over the third time period. Both the third set of glucose levels and the third set of engagement data may be associated with the same user, such as user 8. Using the third set of glucose levels and the third set of engagement data as inputs, the trained machine learning model may be used to determine one or more predictions for future glucose levels or engagement levels (e.g., for a future "fourth" subsequent time period).

Figure 7A:
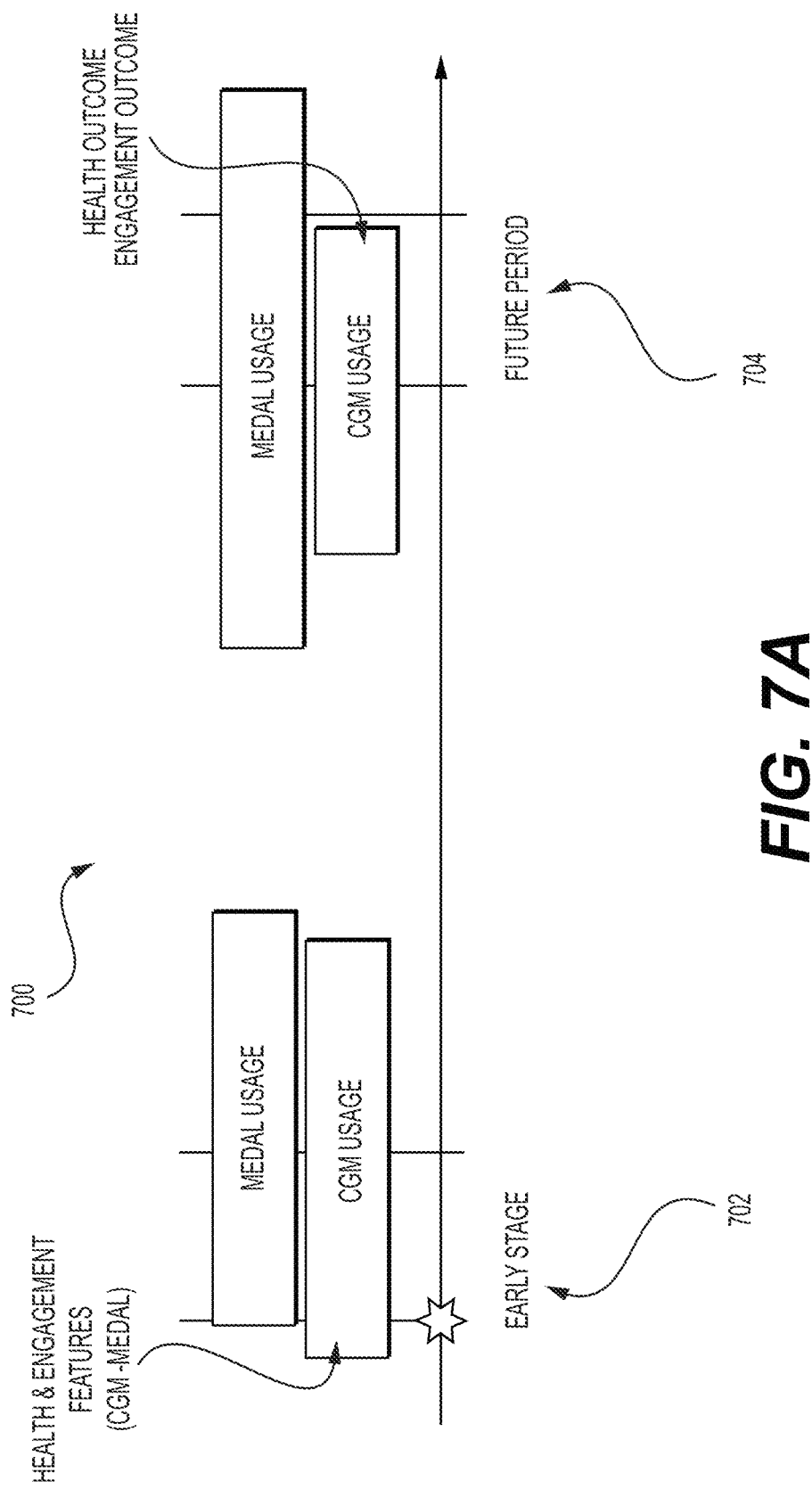

FIG. 7A is a diagram depicting the use of glucose ("CGM usage") and engagement data ("MEDAL usage") to predict future health and engagement outcomes, according to one or more embodiments. Diagram 700 is a timeline with an "early stage" time period 702 (e.g., an initial time period, such as approximately ten days) and a "future period" time period 704. The early stage time period 702 may be a predefined time period where glucose and engagement data is collected to make predictions about glucose and engagement levels during the future period 704. In some embodiments, both the early stage time period 702 and the future period 704 may be the same amount of time, but in some cases they may be different lengths of time. As an example, the early stage time period 702 may range from ten to thirty days and the future period 704 range from approximately five to ninety days. The early stage time period 702 may be directly before the future time period 704, or there may be a gap of time between the early stage period 702 and the future period 704. There may be a pattern displayed during the early stage period 702 that is indicative of behavior and outcomes during the future period 704.

FIG. 7B is a table 710 depicting embodiments for future outcome predictions, in accordance with one or more embodiments. Column 712 includes questions about how early stage data may be used to predict different kinds of future health and engagement outcomes. Column 714 includes outcome variables that may be observed to determine respective outcome predictions. Column 716 includes an assigned number for each question asked and the different scenarios that may be output. Column 718 includes a description of different possible outcome predictions for each observed variable. As shown in FIG. 7B, in some embodiments, there may be nine different categories of outcome predictions based on, for example, three different outcome possibilities (e.g., as shown via the questions in column 712). The outcome predictions may be, for example, based on two and three-state direction or value predictions based on a relative difference from a historical input (e.g., based on CGM data, based on compliance data, based on MEDAL data, based on time information, etc.) as compared to a predicted outcome or two state predictions based on value predictions based on a value of a metric (e.g., TIR value, GRI value, MEDAL engagement value, etc.).

Figure 7C:
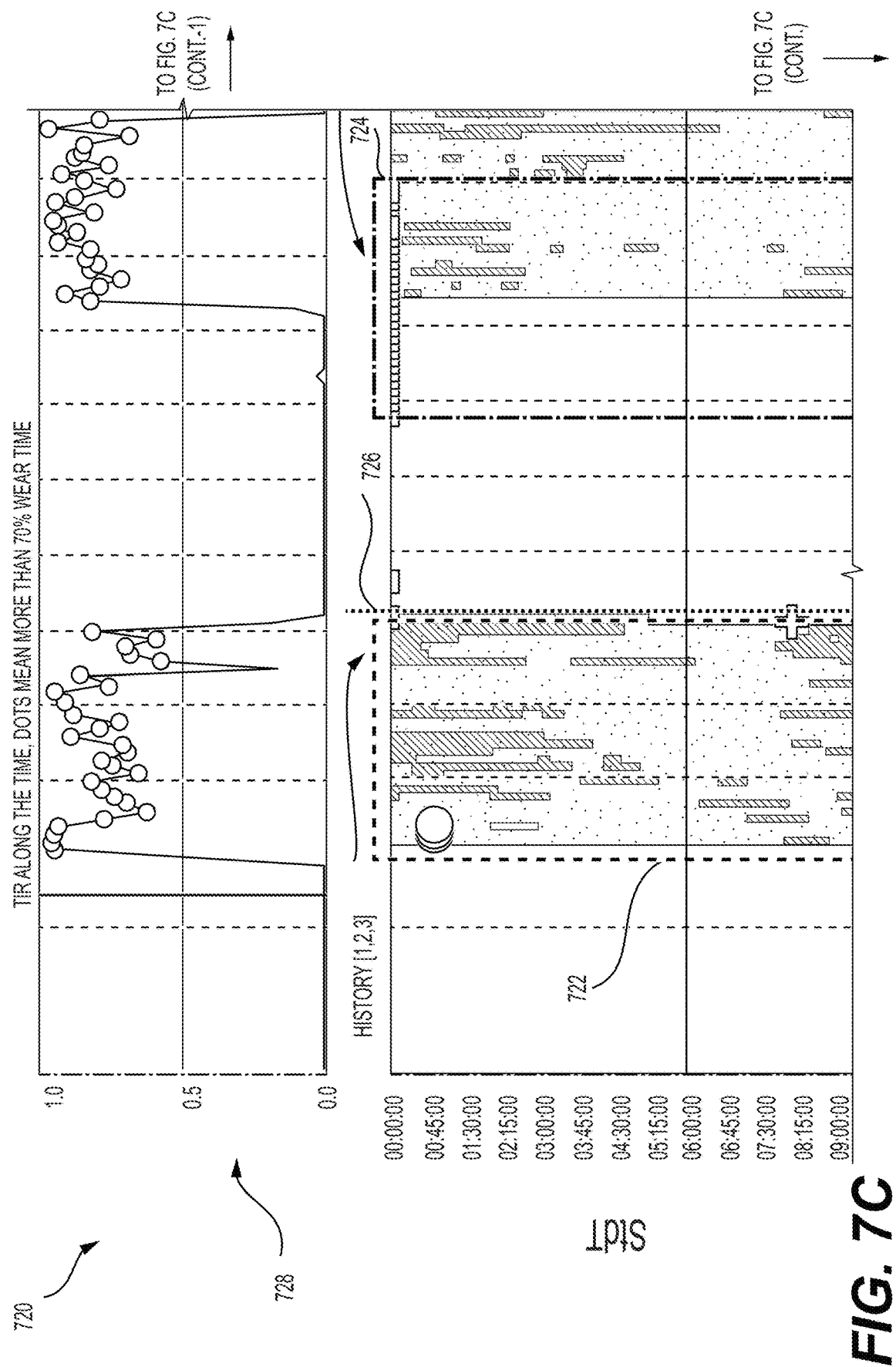
Figure 7C:
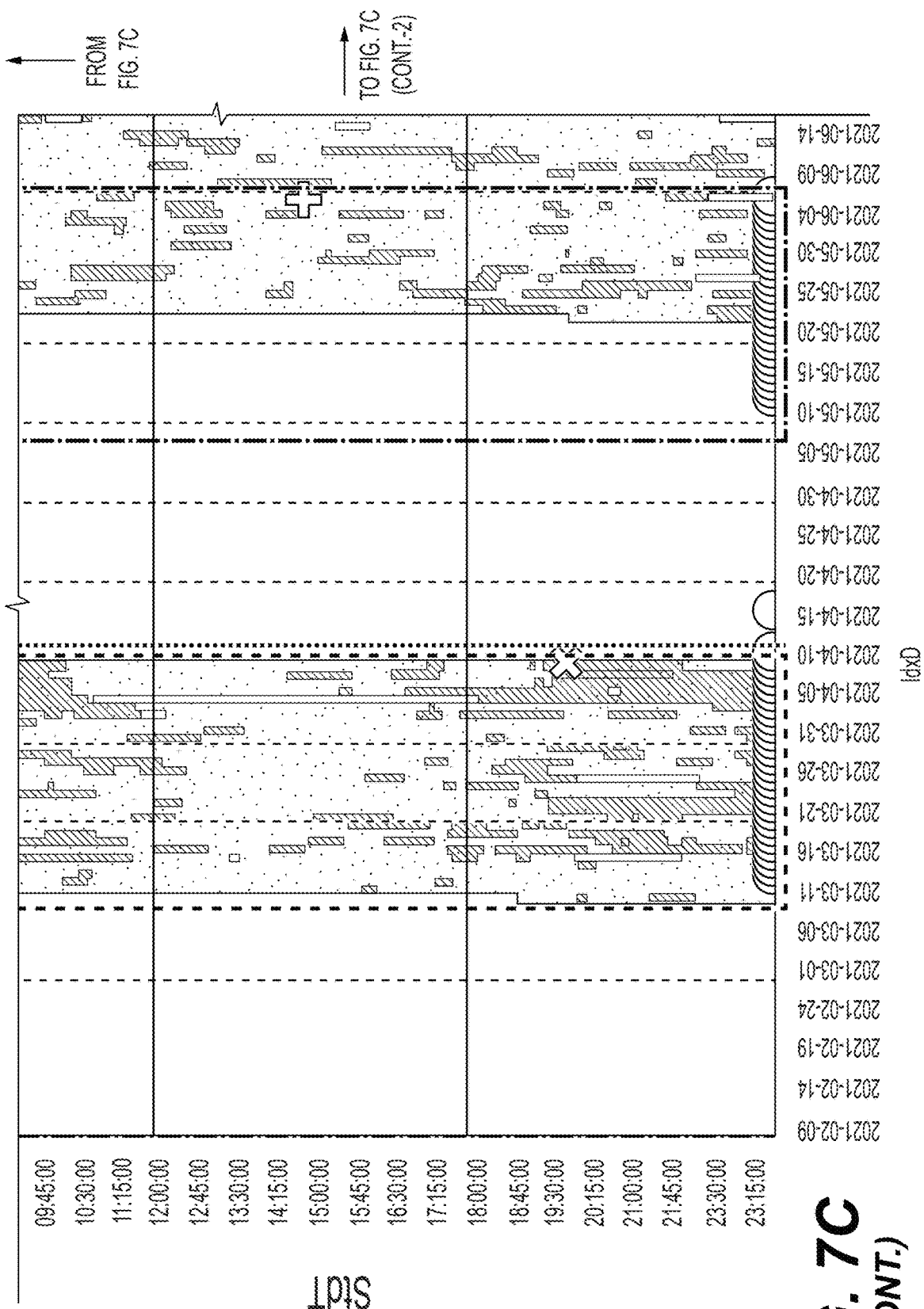

FIG. 7C is a diagram depicting example MEDAL and CGM data collected for an example user, in accordance with one or more embodiments. Each entry for the horizontal axis represents five days while each entry for the vertical axis represents a 45-minute section of a day. For example, at index point 726, values for a historical period 722 of thirty days (e.g., three ten-day periods) are input to a machine learning model to determine predictions for a future period 724 of thirty days. Diagram 720 also shows MEDAL data input in a mHealth application 1 including exercise/activity, height, step, and weight inputs. The top portion 728 of diagram 720 depicts TIR, where a dot indicates that the user used (e.g., wore) a CGM device more than 70% of the time.

Figure 8A:
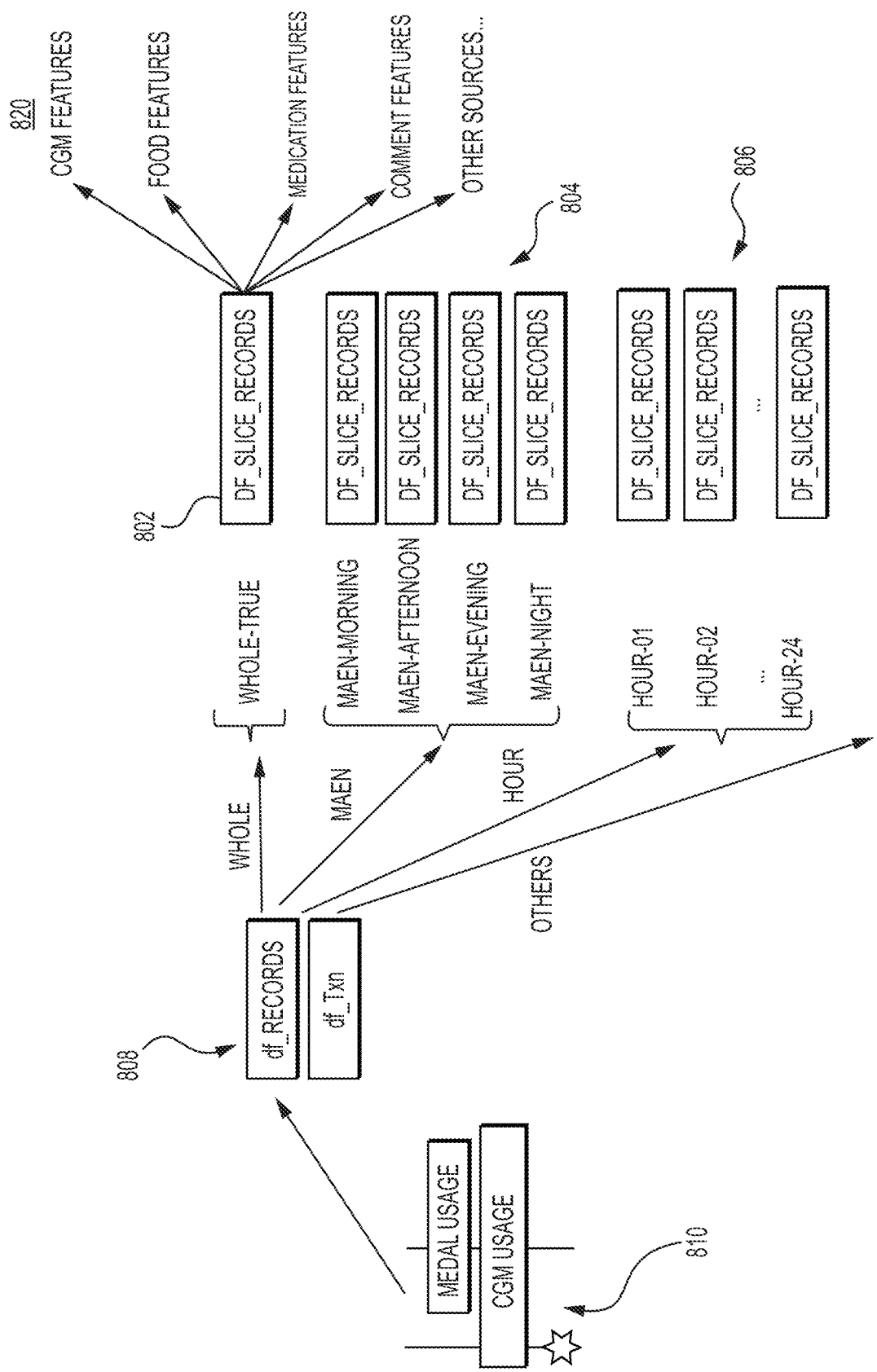
FIGS. 8A-8D show diagrams depicting feature selection in an early stage period, in accordance with one or more embodiments.

FIGS. 8A-8D show diagrams depicting feature selection in the early stage period, according to one or more embodiments of the present disclosure. Records may be data extracted based on glucose values (CGM usage) and/or engagement data (MEDAL usage) 810. Glucose values and/or engagement data 810 may be separated into known and unknown data 808. Records may be aggregated and represented by a single value or record, represented in FIG. 8A by whole records 802, which may represent mean values for glucose levels and other potential features. Records may be sliced into smaller segregated sections (e.g., segregated by time) represented by aggregated slices such as MAEN values (e.g., morning, afternoon, evening, night mean values) for records 804 and hourly records 806. From each record, one or more features 820 may be extracted, including, for example as shown in FIG. 8A, CGM features, food features, medication features, comment features, etc.

Figure 8B:
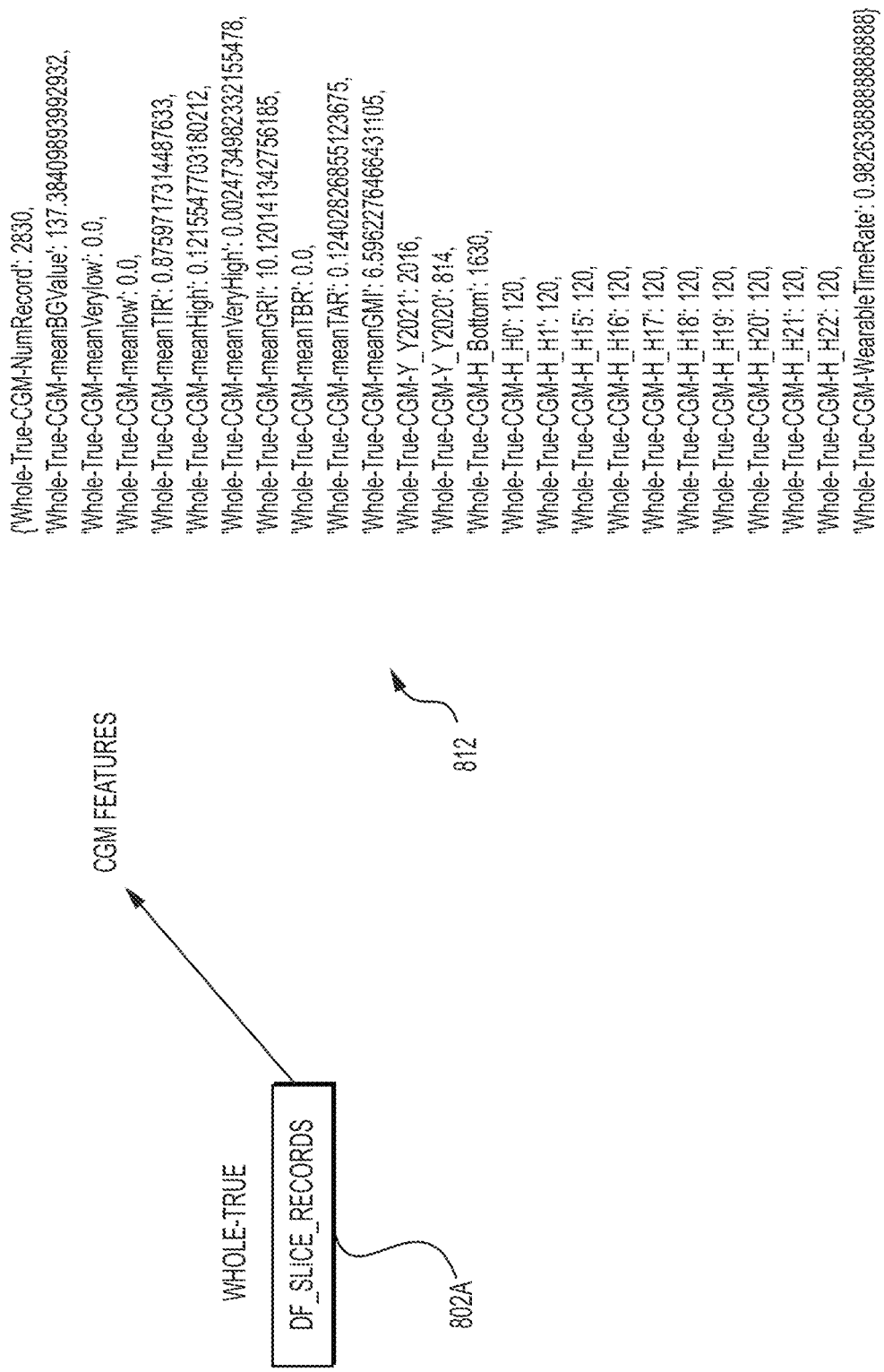
Figure 8C:
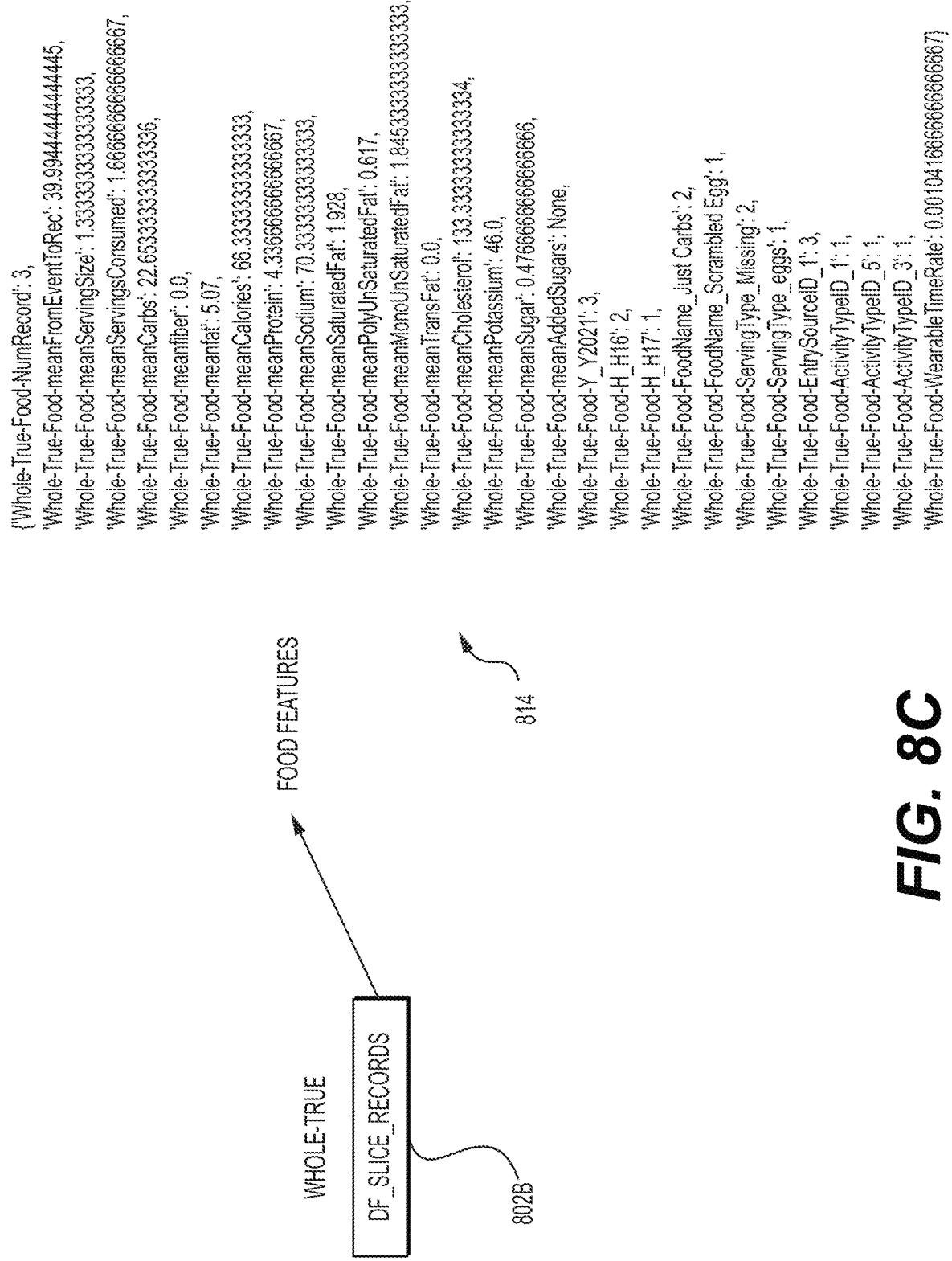
Figure 8D:
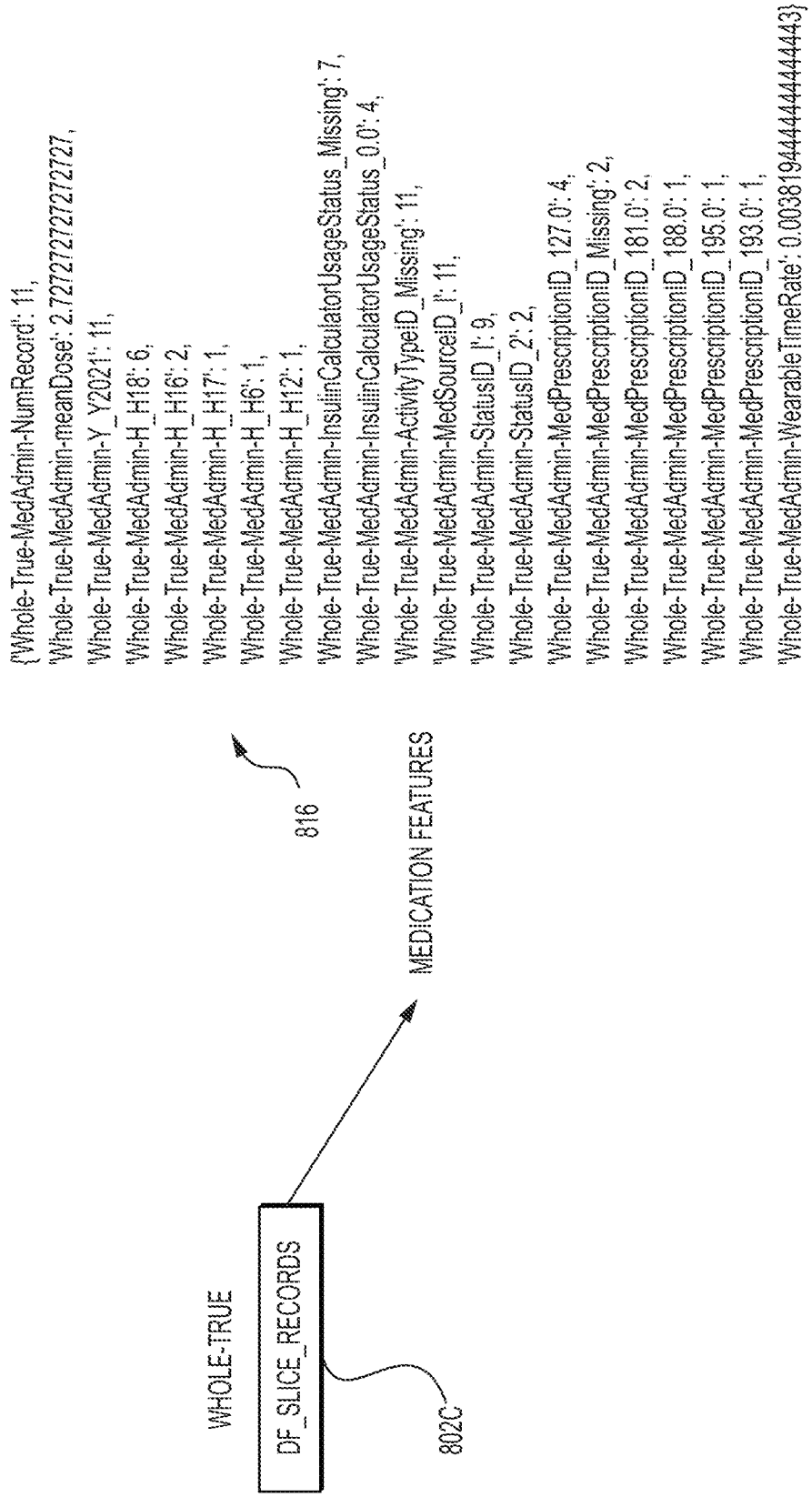

In some embodiments, a single feature may include several attributes, which may be used as features themselves, as shown in FIGS. 8B-8D. This feature expansion may be useful in improving the accuracy of a machine learning model used to predict future health and engagement outcomes. For example, as shown in FIG. 8B, metadata related to CGM glucose values and/or mean values may be attributes or subfeatures 812 of a single CGM glucose value feature 802A. A single CGM glucose value feature 802A may include several subfeatures 812 of features, such as meanBGValue (mean blood glucose value over a period of time), meanVeryLow (mean percentage of time with very low blood glucose values), meanLow (mean percentage of time with low blood glucose values), meanTIR (mean percentage of time in range), meanHigh (mean percentage of time with high blood glucose values), meanVeryHigh (mean percentage of time with very high blood glucose values), meanGRI (mean GRI value over a period of time), meanTBR (mean percentage of time below range), meanTAR (mean percentage of time above range), meanGMI (mean glucose management indicator value), and wearable TimeRate (percentage of time spent wearing a wearable CGM device). In some embodiments, subfeatures are predefined and categorized with supervision. A machine learning model may rank each of the features to determine which are most influential in the results. In some embodiments, a machine learning model may determine features and subfeatures without manual intervention. For example, a machine learning model may provide predicted glucose and/or engagement levels based on historical glucose and/or engagement levels (e.g., collected during an initial period). The machine learning model may further output a ranking of the features (or subfeatures) in order based on the reliance of each feature in determining the predicted glucose and/or engagement levels. The ranking of the features may be provided, for example, as an ordered list via a graphical user interface (GUI). The list may be ordered based on the ranking and may be updated based on updated machine learning outputs.

According to an embodiment, an instance of mHealth application 1 for user 8 may be automatically updated based on the ranking of the features associated with user 8. For example, the ranking of the features may be used to identify one or more features that meet a threshold for affecting favorable predicted glucose levels and/or engagement for that user. Accordingly, the instance of mHealth application 1 for user 8 may be automatically updated to generate alerts (e.g., medication, diet, activity, etc. based alerts) that encourage performance based on the one or more features that meet the threshold for affecting favorable predicted glucose levels and/or engagement. For example, mHealth application 1 may be updated to generate alerts and/or notifications, or more frequent alerts and/or notifications, based on the one or more features that meet the threshold for affecting favorable predicted glucose levels and/or engagement.

FIG. 8C shows subfeatures 814 that may be extracted from a single example food feature 802B. For example, a single food feature may be a user entry that user 8 ate a sandwich. Several subfeatures may be extracted from a user entry of a food eaten. For example, the number of calories and other nutritional metrics (e.g., carbohydrates, fiber, fat, protein, sodium, types of fat, vitamins, minerals, sugars, etc.) may be used as features for a machine learning model.

FIG. 8D shows subfeatures 816 that may be extracted from an example single medication feature 802C. For example, a single medication feature may include a use entry that user 8 took a particular medication. Several subfeatures may be included in the user entry including mean dosage, time of medication, type of medication, prescription class, etc. Similar principles of feature expansion apply to other features such as education activities, physical activity, and/or lab test results.

FIGS. 9A-9E show charts depicting experimental results of an application of a machine learning model, according to one or more embodiments disclosed herein. FIG. 9A shows the results of several different machine learning models trained to predict a difference in TIR. In this example, a sample of three ten-day periods [1,2,3] of time with more than approximately 2880 total CGM readings and at least one engagement activity was input to various machine learning models. The models with the highest accuracy for this experiment are listed in FIG. 9A, while several models with lesser accuracy are not listed. Table 902 depicts models that predicted three different states of TIR (e.g., more than approximately 5% worse TIR from input periods, within approximately 5% of measured TIR, more than approximately 5% better TIR), separated by the type of diabetes and the number of future periods predicted. By way of explanation, "DT1" and "DT2" refer to type 1 diabetes and type 2 diabetes, respectively. "AUC" refers to area under a curve, which may indicate a model's ability to distinguish classes. As shown in table 902, accuracy ranged in this example experiment from 43% to approximately 55%. Other metrics including recall, precision, and F1 score are included in table 902, and all subsequent tables shown in FIGS. 9A-9E. Recall is a performance metric used to measure the ability of a model to correctly identify all positive instances from a dataset. It is the proportion of true positive instances that are correctly identified by the model out of all the positive instances present in the dataset. Precision is a performance metric used to measure the ability of a model to correctly identify positive instances that are correctly identified by the model out of all the instances that the model identifies as positive. It is the proportion of true positive instances that are correctly identified by the model out of all the instances that the model has identified as positive. An F1 score is a performance metric that combines precision and recall into a single measure of overall model performance. Table 904 depicts models that predicted two different states (e.g., better TIR or worse TIR from measured TIR in input periods). The accuracy is increased for these predictions, ranging from 58.33% to 64.33%.

FIG. 9B shows the results of several models' ability to predict engagement outcomes. In this example, a sample of three ten-day periods [1,2,3] of time with at least some record of CGM activity and other engagement (MEDAL) activity was input to various machine learning models to predict different engagement outcomes for three ten-day periods [7,8,9]. Table 910 depicts models that predicted future CGM engagement (e.g., a high engagement state or a low engagement state) with 76.25% accuracy for type 1 diabetes, and with 79.29% for type 2 diabetes. Table 912 depicts models that predicted future engagement (e.g., a high engagement state or a low engagement state) with a mobile application, such as mHealth application 1, with around 90% accuracy for both type 1 and type 2 diabetes.

FIG. 9C shows the results of several models' ability to predict health outcomes (e.g., TIR values and changes). In this example, a sample of three ten-day periods [1,2,3] of time with more than approximately 2880 total CGM readings and, in some cases, at least one engagement activity were input to various machine learning models. As shown in table 920, including the engagement data (MEDAL data) improved the accuracy of a model's output from 47.58% to 51.59%, considering a three-state TIR prediction. As shown in table 922, including the engagement data (MEDAL data) improved the accuracy of a model's output from 61.21% to 62.95%, considering a two-state TIR prediction.

FIG. 9D shows the results of several models' ability to predict health outcomes (TIR values and changes). The primary difference between the examples in FIG. 9C and FIG. 9D is that the input for the tests in FIG. 9D include more than 5 engagement activities, indicating a higher engagement with a mobile application (e.g., mHealth application 1). Table 930 shows that if a user 8 has a higher initial engagement state with mHealth application 1 and a higher CGM engagement, then prediction accuracy may be improved to over approximately 68%, when considering a three-state TIR prediction. Table 932 shows that if a user 8 has a higher initial engagement state with mHealth application 1 and a higher CGM engagement, then prediction accuracy may be improved to over approximately 61%, when considering a two-state TIR prediction.

FIG. 9E shows further results of several models' ability to predict engagement outcomes (CGM engagement and mHealth application 1 engagement). This experiment differs from the experiment depicted in FIG. 9B as the input for the tests in FIG. 9E include more than 5 engagement activities. Table 940 shows a model accuracy of approximately 78% for predicting a two-state CGM engagement, while table 942 shows a model accuracy of approximately 68-69% for predicting a two-state engagement with mHealth application 1.

FIGS. 9F and 9G show further results of a model's proficiency (accuracy, AUC value, precision value, recall value, and F1 value) when predicting TIR values based on an initial set of data (e.g., CGM data, compliance data, MEDAL data, etc.). Table 950 of FIG. 9F shows the model's proficiency in determining whether a future TIR value will be one of three states: worse (e.g., less than a current value by more than approximately 5%); the same (e.g., within approximately 5% of a current value); or better (e.g., greater than a current value by more than approximately 5%). Table 952 of FIG. 9G shows the model's proficiency in determining whether a future TIR value will be one of two states: worse than a current/historical TIR value or better than the current/historical TIR value.

Figure 9H:
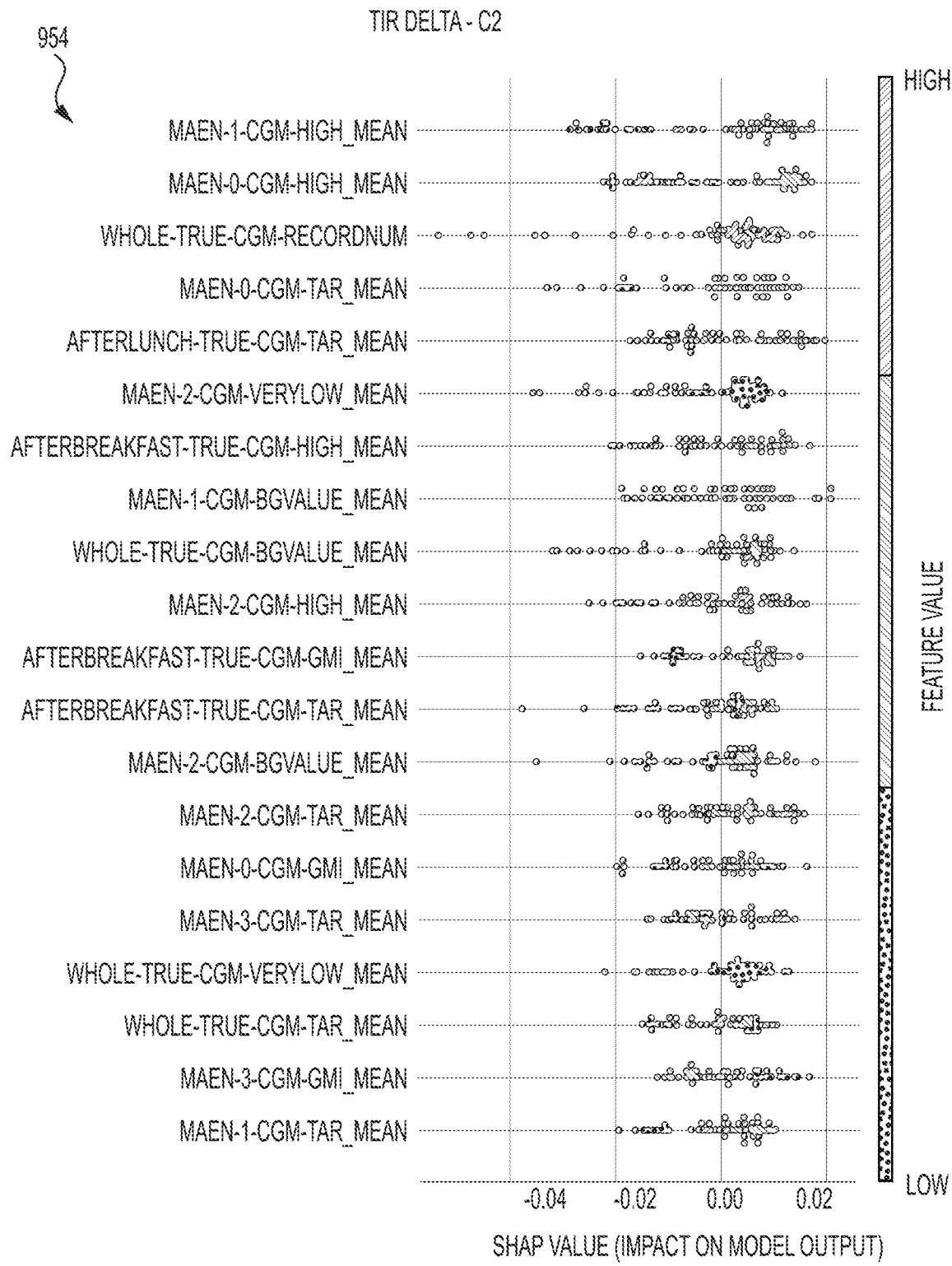
FIGS. 9A-9X show charts depicting results of a machine learning model, in accordance with one or more embodiments.

FIG. 9H is a diagram 954 depicting Shapley additive explanation (SHAP) values and feature values for a set of features and/or subfeatures used in a model to predict TIR value differences, in accordance with one or more embodiments. For example, the horizontal axis of diagram 954 depicts SHAP values, which indicate a value of impact a given feature or subfeature had on a model output. Each dot in diagram 954 represents an individual (e.g., a user). The pattern of each dot represents a feature value with first patterns representing small feature values, second patterns representing medium feature values, and third patterns representing large feature values. In the example diagram 954, the features with the highest impact on model output were related to CGM values. For example, when there are many high CGM glucose values (e.g., greater than 180 mg/dL), the user is more likely to have better TIR values in the future relative to current or historical TIR values. As another example, when there are relatively low CGM glucose values (e.g., less than 54 mg/dL) indicated in the historical data, the user is more likely to have worse TIR values in the future.

FIG. 9I shows results of a model's ability to predict absolute (e.g., nonrelative) TIR values in a future period. Table 956 of FIG. 9I shows the model's proficiency in determining whether a future TIR value will be one of two states: greater than or equal to a target TIR value (e.g., approximately 70% TIR); or less than the target TIR value.

Figure 9J:
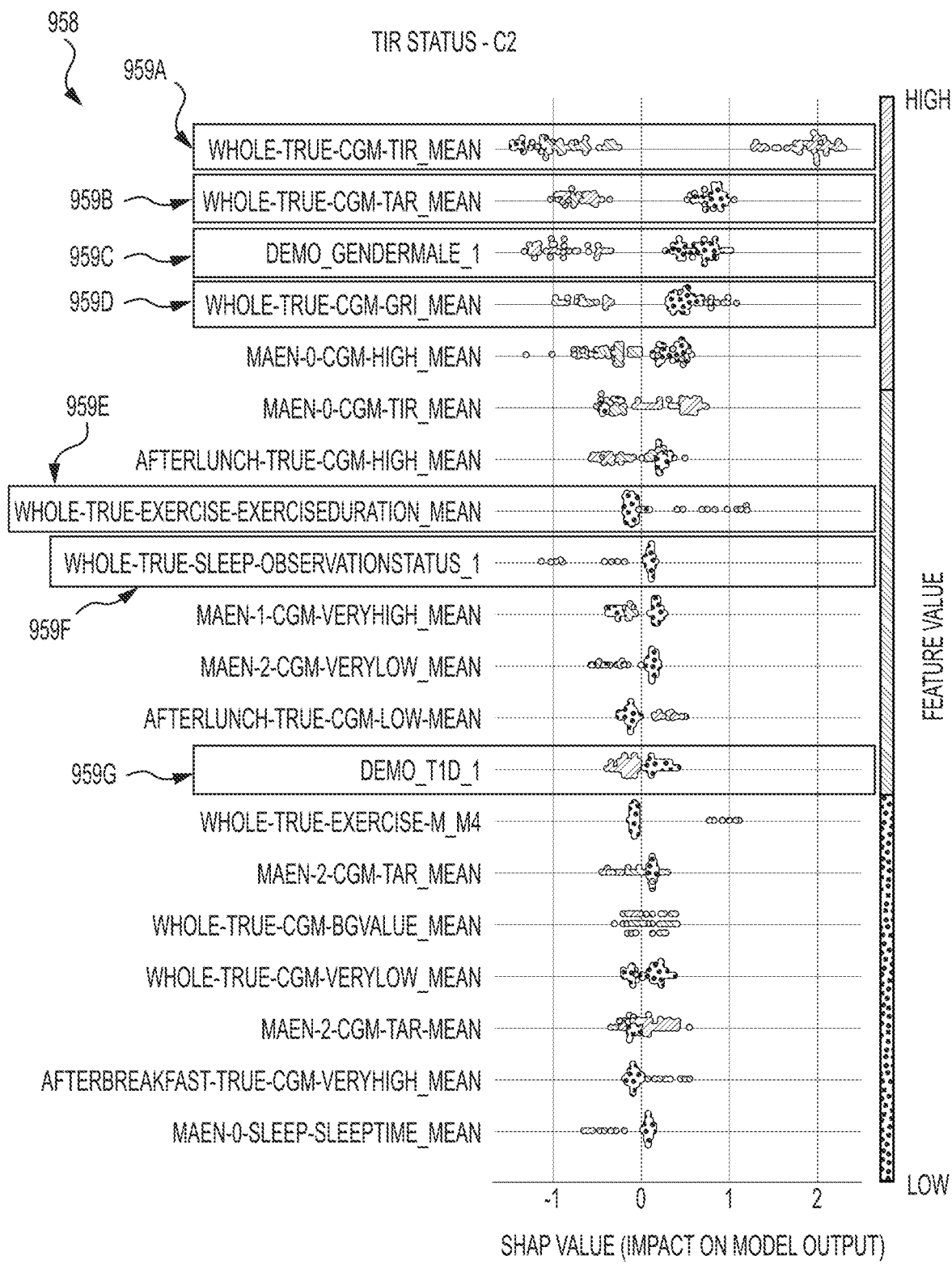

FIG. 9J is a diagram 958 depicting SHAP values and feature values for a set of features and/or subfeatures used in a model to predict TIR values, in accordance with one or more embodiments. For example, high historical TIR values 959A and high historical exercise duration 959E may have a positive impact on TIR values in future periods. However, high historical TAR values 959B, male status 959C, high historical GRI values 959D, more sleep in history 959F, and type 1 diabetes status 959G may have a negative impact on TIR values in future periods.

FIGS. 9K and 9L show results of a model's ability to predict future GRI value differences relative to a current/historical GRI value. Table 960 of FIG. 9K shows the model's proficiency in determining whether a future GRI value will be one of two states: worse than a current/historical TIR value or better than the current/historical TIR value. Table 962 of FIG. 9L shows the model's proficiency in determining whether a future GRI value will be one of three states: worse (e.g., less than a current value by more than approximately 5%); the same (e.g., within approximately 5% of a current value); or better (e.g., greater than a current value by more than approximately 5%).

FIG. 9M shows results of a model's ability to predict absolute (e.g., nonrelative) GRI values in a future period. Table 964 of FIG. 9M shows the model's proficiency in determining whether a future GRI value will be one of two states: greater than or equal to a target GRI value (e.g., GRI value of approximately 40); or less than the target GRI value.

FIG. 9N shows results of a model's ability to predict engagement of mHealth application 1 in a future period. Table 966 shows the model's proficiency in determining whether a user's future engagement of mHealth application 1 will be one of two states: high engagement (e.g., more than or equal to approximately five engagement activities); or low engagement (e.g., less than approximately five engagement activities).

Figure 9O:
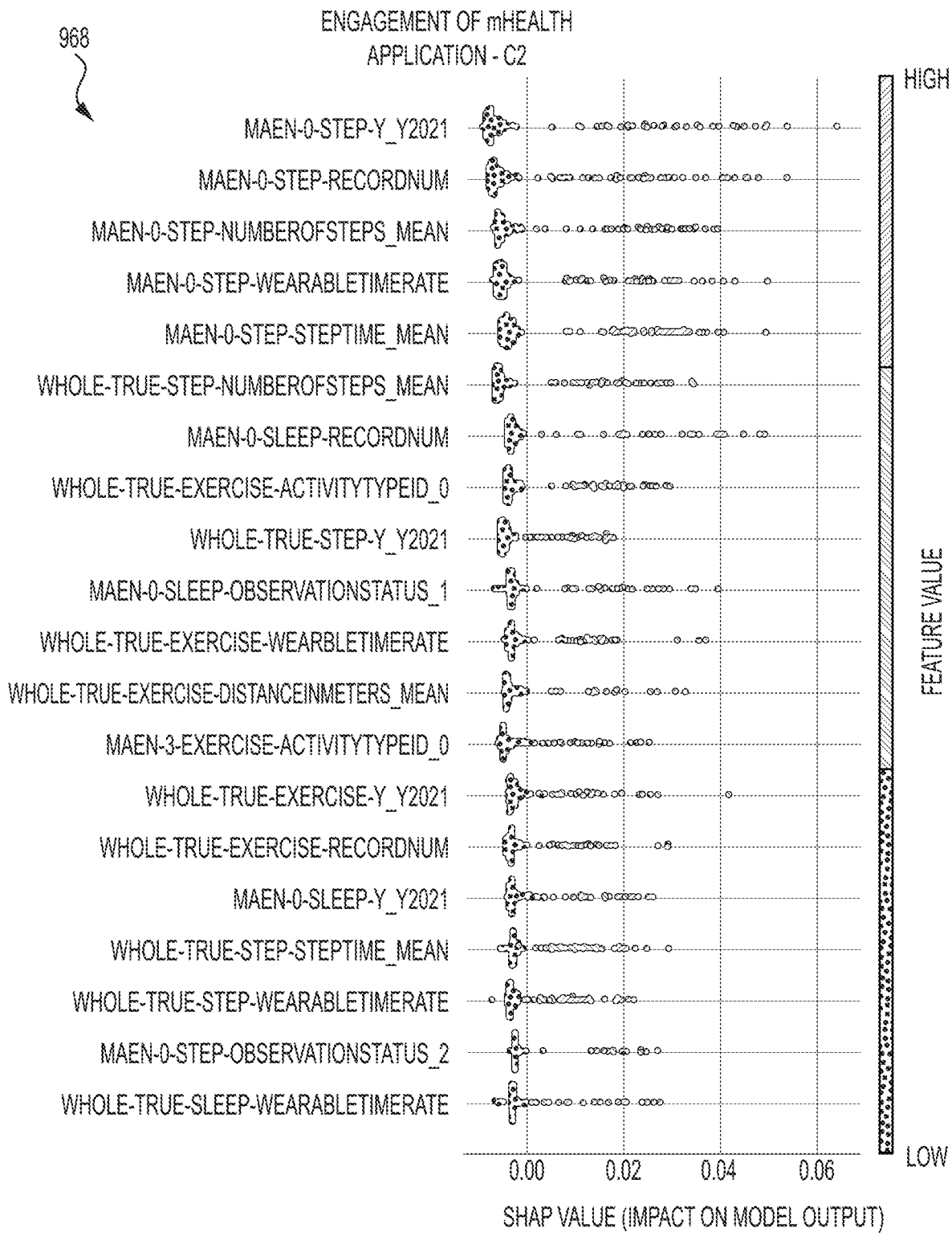

FIG. 9O is a diagram 968 depicting SHAP values and feature values for a set of features and/or subfeatures used in a model to predict engagement levels, in accordance with one or more embodiments. For example, a number of steps, an amount of sleep, and exercise are found to have an impact on accurately determining engagement levels in the future. A greater number of step records and a greater number of steps may have a positive impact on morning engagement while wearing a wearable more during the morning hours may have a positive impact on engagement overall.

FIG. 9P shows results of a model's ability to predict manual engagement of mHealth application 1 in a future period. Manual engagement refers to engagement activities that generally require a manual user input in mHealth application 1. Therefore, since many engagement activities are automatically measured by a wearable, when determining manual engagement, activity engagement may be excluded. Table 970 shows the model's proficiency in determining whether a user's future manual engagement of mHealth application 1 will be one of two states: high manual engagement (e.g., more than or equal to approximately five engagement activities including medication intake, education activities, diet, and lab results); or low manual engagement (e.g., less than approximately five engagement activities including medication intake, education, diet, and lab result activities).

Figure 9Q:
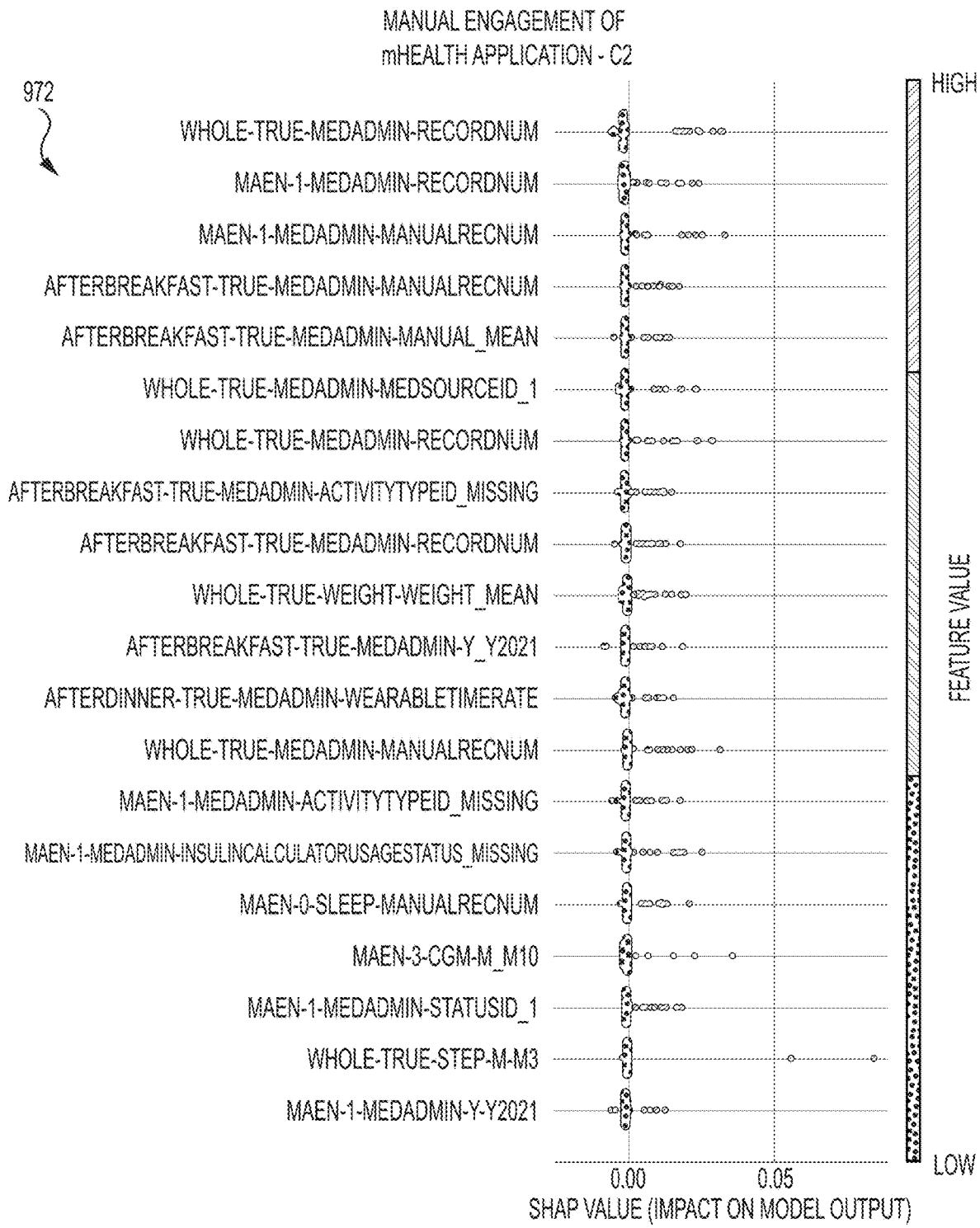

FIG. 9Q is a diagram 972 depicting SHAP values and feature values for a set of features and/or subfeatures used in a model to predict manual engagement levels, in accordance with one or more embodiments. For example, as shown in diagram 972, medication administration, weight inputs, and manually entered sleep records are found to have an impact on accurately determining manual engagement levels in the future.

FIG. 9R shows results of a model's ability to predict CGM engagement in a future period. Table 974 of FIG. 9R shows the model's proficiency in determining whether a future CGM engagement level will be one of two states: greater than or equal to a target CGM device wear time (e.g., approximately 70% of time, or approximately 70% or total 2880 possible readings in one week); or less than the target CGM device wear time.

Figure 9S:
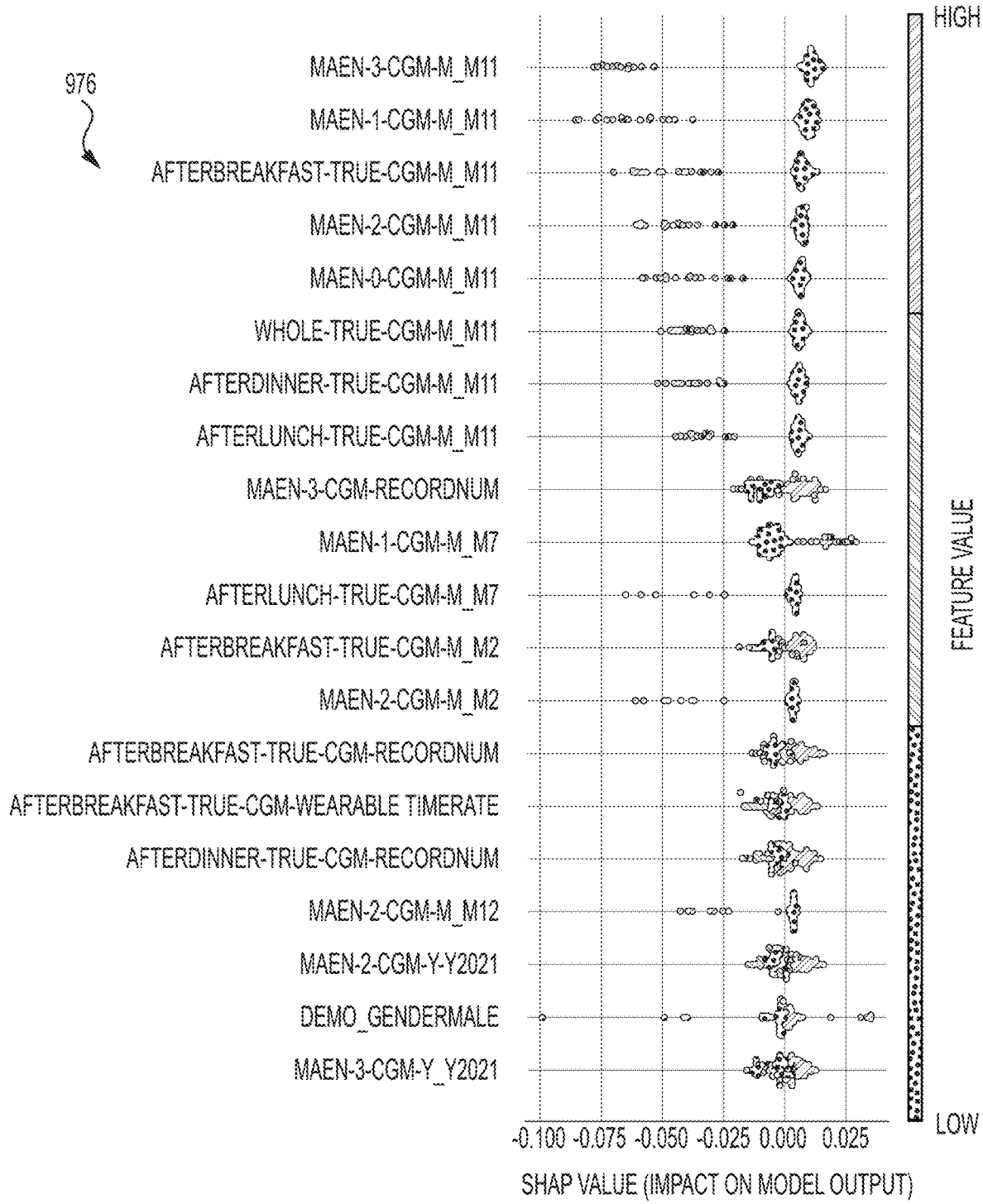

FIG. 9S is a diagram 976 depicting SHAP values and feature values for a set of features and/or subfeatures used in a model to predict CGM engagement levels, in accordance with one or more embodiments. For example, as shown in diagram 976, in M11 (e.g., month 11, or November), a greater number of night-time CGM records, as well as evening, afternoon, morning, after breakfast, after lunch, and after dinner CGM records may have a negative impact on CGM engagement. However, in M7 (July), a greater number of CGM records may have a positive impact on CGM engagement. A greater number of night records generally may have a positive impact on CGM engagement as well as individuals that are categorized as male may exhibit a positive impact in future periods.

FIG. 9T shows results of a model's ability to predict CGM engagement in a future period based on historical engagement data. Table 978 of FIG. 9T shows the model's proficiency in determining whether a future CGM engagement level, as determined based on using engagement data as inputs to the model, will be one of two states: greater than or equal to a target CGM device wear time (e.g., approximately 70% of time, or approximately 70% or total 2880 possible readings in one week); or less than the target CGM device wear time.

Figure 9U:
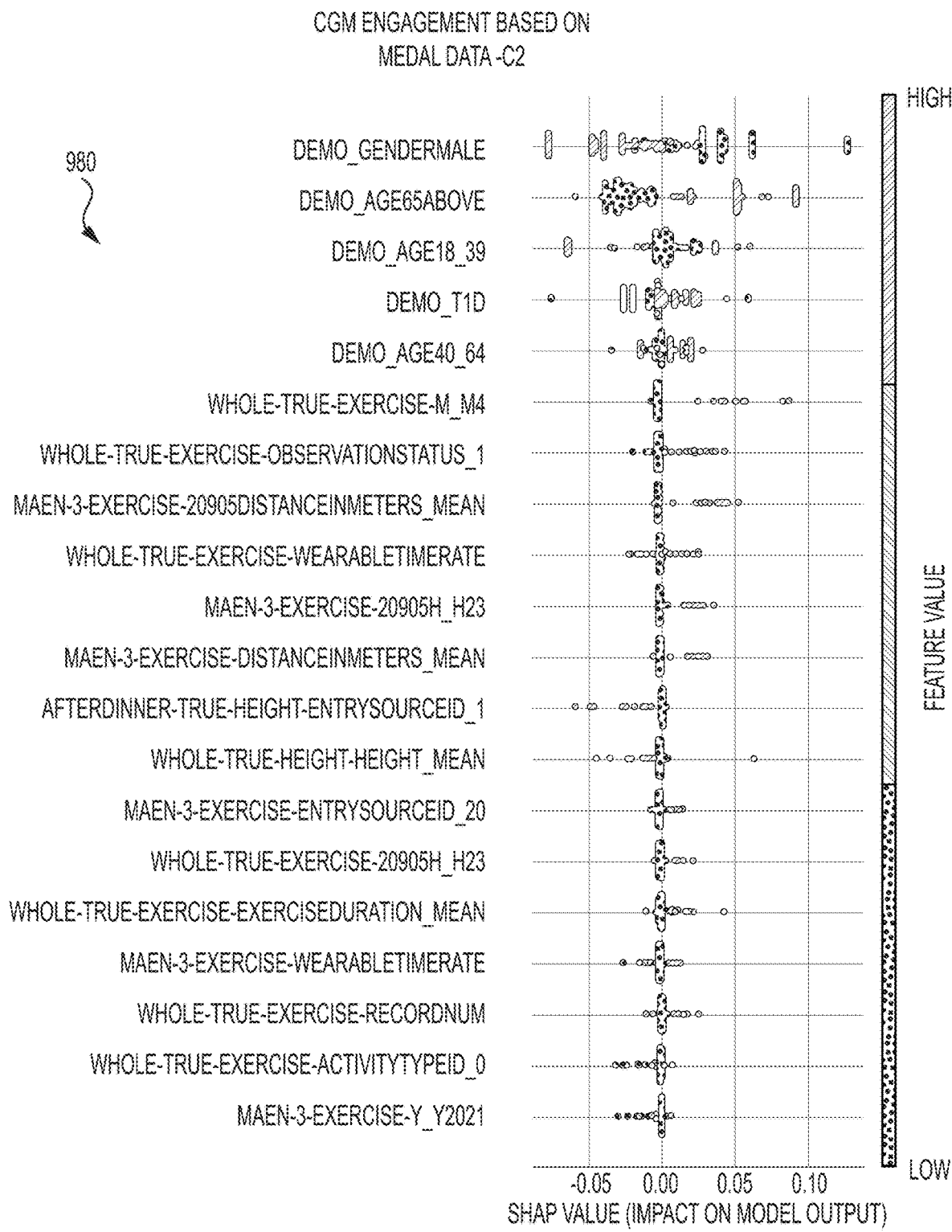

FIG. 9U is a diagram 980 depicting SHAP values and feature values for a set of features and/or subfeatures used in a model to predict CGM engagement levels, in accordance with one or more embodiments. For example, a male status may have a negative relationship with CGM engagement while patients over age 65 and type-1 diabetes status may have a positive relationship with CGM engagement. Individuals with more exercise records may have positive relationship with CGM engagement. Other features including exercise distance, evening exercise, and exercise duration have impacts on the model output, but demographic features tend to influence the output more significantly.

Figure 9V:
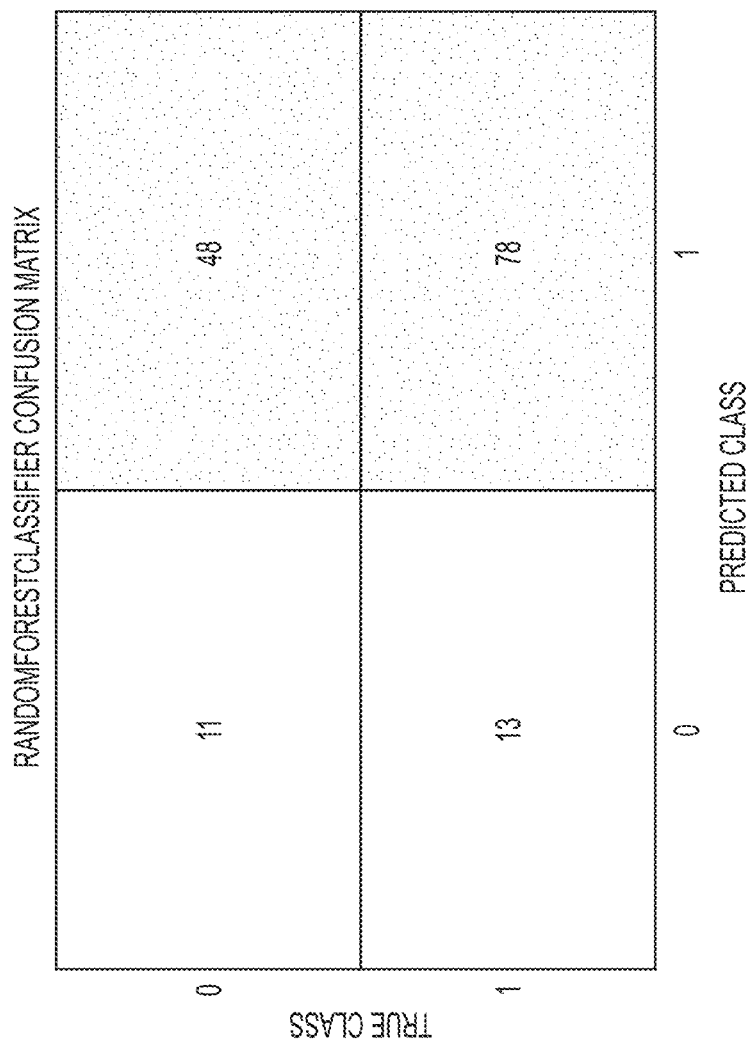

FIG. 9V is a confusion matrix 982 based on predicted CGM engagement levels and actual CGM engagement levels, in accordance with one or more embodiments. As shown in random forest classifier confusion matrix 982, the model tends to make more positive predictions that users are more likely to engage with a CGM device in the future than the number of actual users that engage with a CGM device.

Figure 9W:
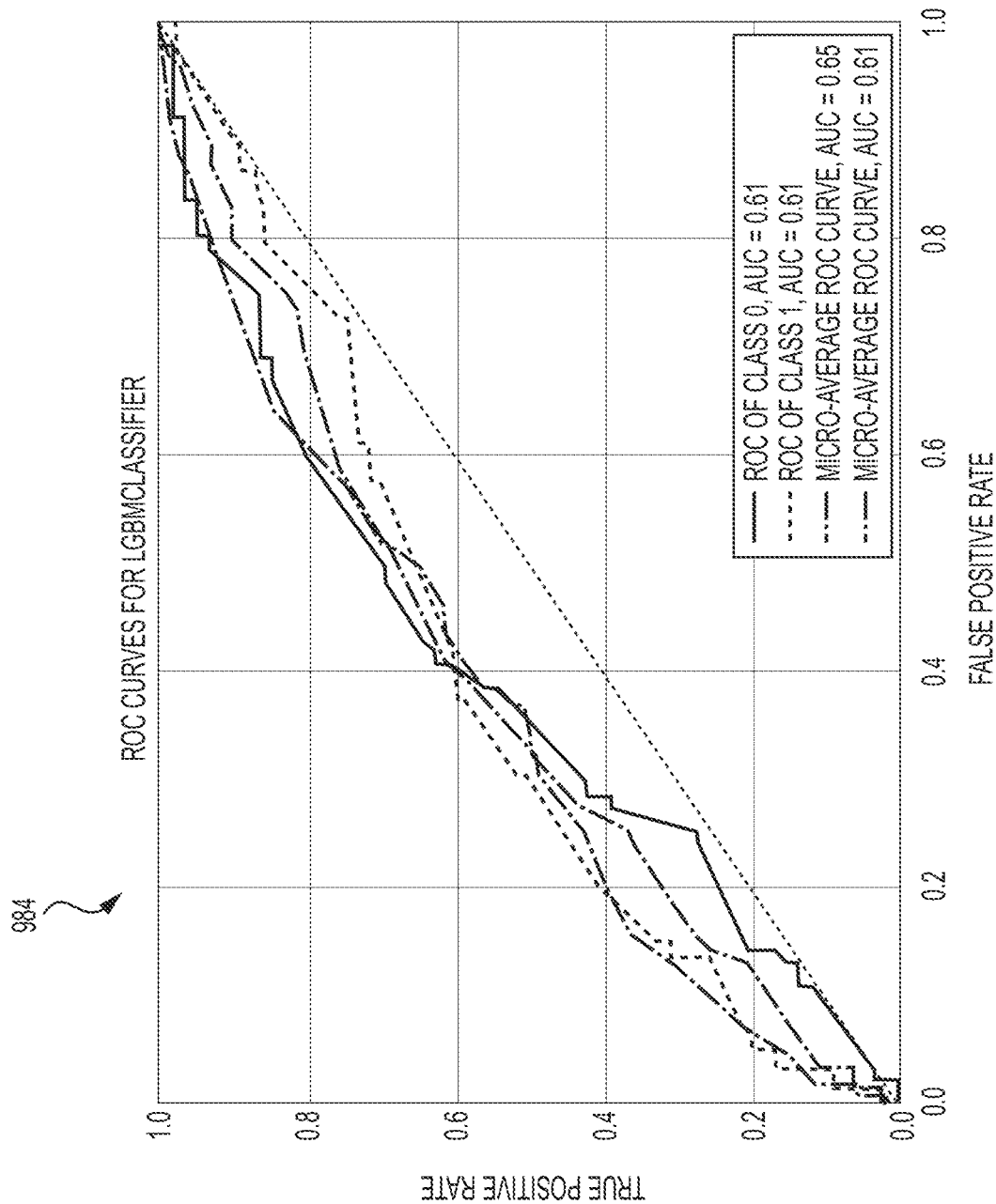
Figure 9X:
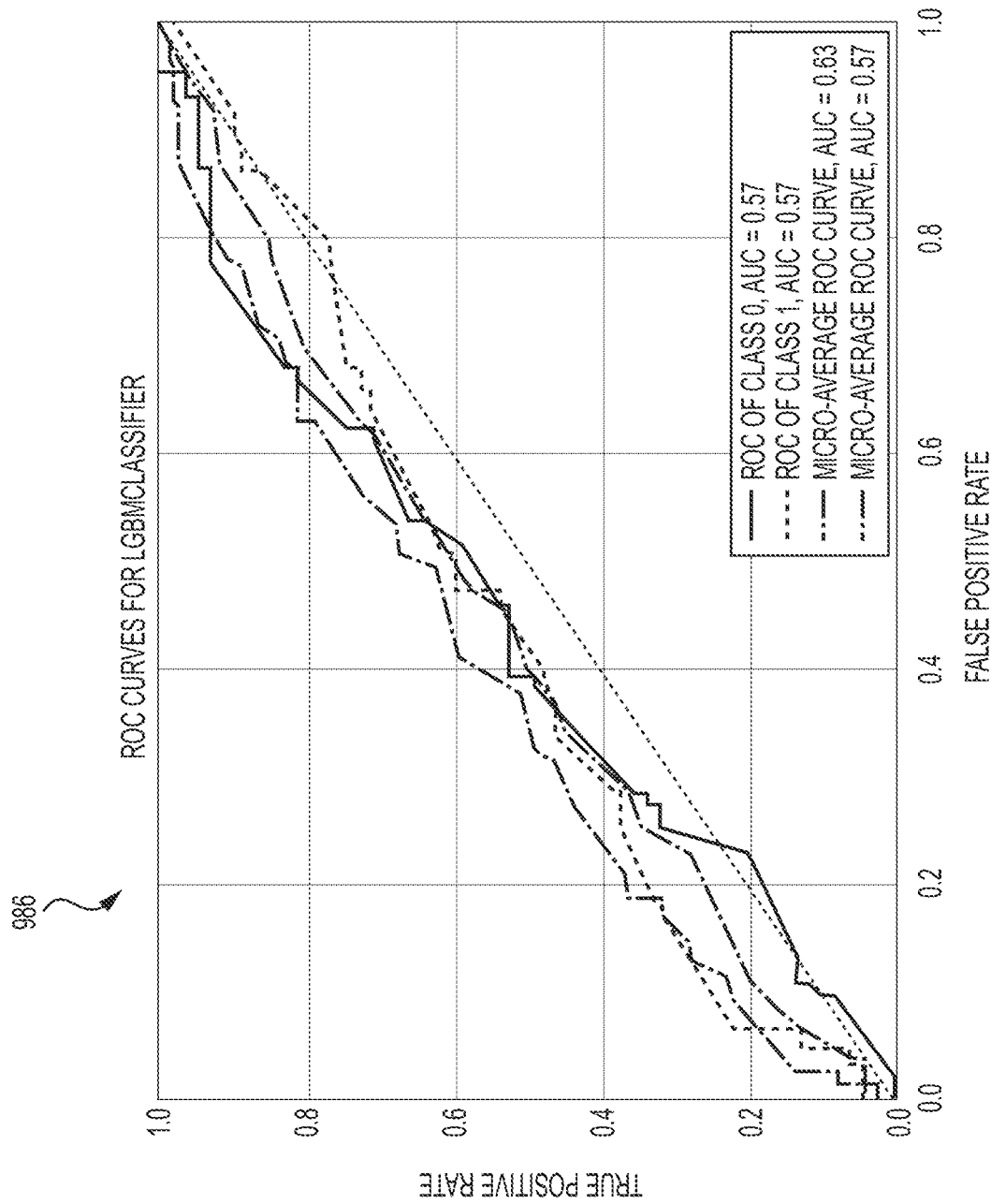

FIGS. 9W and 9X are examples of plots depicting an AUC for different models, in accordance with one or more embodiments. For example, plot 984 of FIG. 9W depicts an AUC for a random forest classifier model and plot 986 of FIG. 9X depicts an AUC for a light gradient boosting machine (LGBM) model. While both models have comparatively similar accuracies and recall values, the random forest classifier has a higher AUC which shows a better ability to distinguish between classes and may be used as a summary of a receiver operating characteristic (ROC) curve.

In some embodiments, a TIR value of approximately 0.7 or greater may be a clinically meaningful target for optimal diabetes management. Accordingly, a binary outcome variable for TIR may be set to be a first state for TIR being greater than or equal to approximately 0.7 and a second state for TIR being less than approximately 0.7. Different types of models may be implemented including, for example, LGBM, Random Forest Classifiers, Quadratic Discriminant Analysis, Naïve Bayes, and/or Logistic Regression models to predict whether TIR in a prediction period will be greater than approximately 0.7. In an experiment among the different models (e.g., five different models) that were implemented, test results from 304 individuals show that the LGBM model had a prediction accuracy of 0.80 and an AUC of 0.88. Random Forest Classifier had a model performance with accuracy of 0.77 and AUC of 0.82. Quadratic Discriminant Analysis model had a recall score of 0.94. As for feature importance, a high baseline TIR and long exercise duration were shown to increase the probability of future TIR being over 0.7. High baseline TAR, male gender, and Type 1 Diabetes negatively impacted TIR, meaning they reduced the probability of TIR being over 0.7. The various model output statistics show that decision tree based models like LGBM and Random Forest classifier may be suited for predicting health outcome variables like TIR above or below clinically meaningful thresholds. Feature importance analysis may help to understand which baseline CGM and MEDAL features are important and their impact on future health outcomes. These features may be used in designing meaningful personalized interventions for population and individual health management.

Figure 10A:
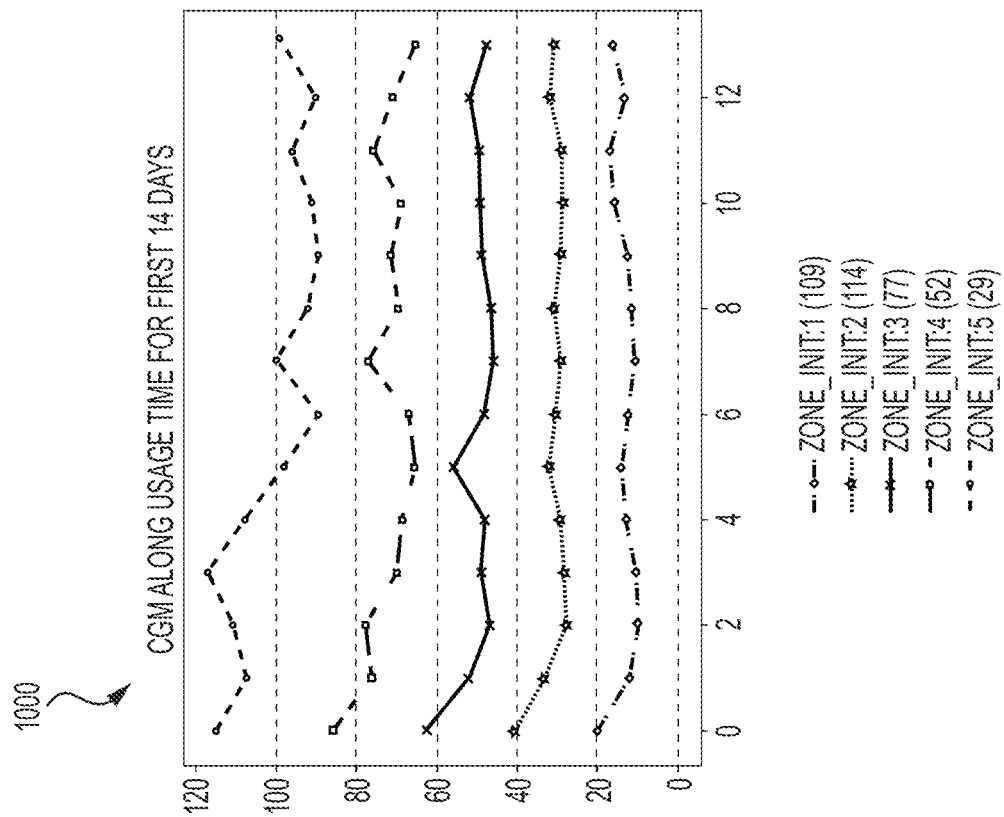
FIGS. 10A-10D show example plots of mean GRI values over time for groups of individuals, in accordance with one or more embodiments.

FIGS. 10A-10D depict example plots of mean GRI values over time for various groups of individuals, according to one or more embodiments. FIG. 10A depicts an example plot 1000 of mean GRI values over time for a group of individuals, according to one or more embodiments. GRI values for CGM users is displayed on the vertical axis. The number of days where a GRI value was determined for the CGM user is displayed on the horizontal axis. Each line in example plot 1000 represents a mean GRI value for a group of individuals that started in each of the five zones. As shown in the example illustrated by plot 1000, the individuals whose baseline GRI value started in zones A and B generally ended with higher GRI values but stayed in the same respective zones (zone A and zone B). However, the individuals whose respective baseline GRI values started in zones C, D, and E generally improved their GRI value such that, at the end of the 14-day period, each group of individuals had improved to a higher zone. In other words, individuals who started in zone C generally ended in zone B, the individuals who started in zone D generally ended in zone C, and the individuals who started in zone E generally ended in zone D. In some cases, one or more improvements were a result of one or more techniques disclosed herein.

Figure 10B:
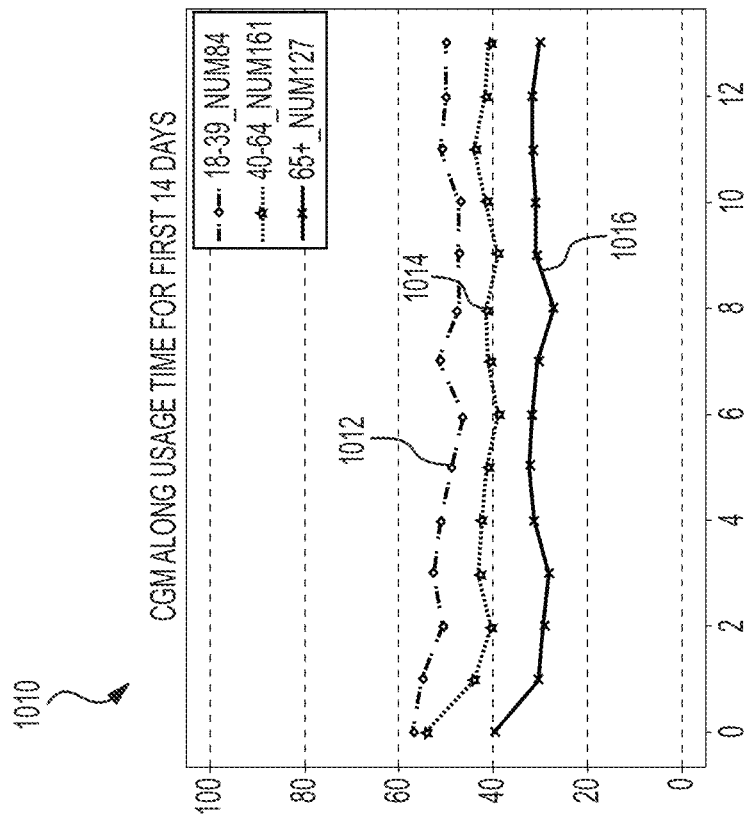

FIG. 10B depicts another example plot 1010 of mean GRI values over time for a group of individuals, according to one or more embodiments. Example plot 1010 displays three different groups of individuals, grouped by age. The top line 1012 represents individuals aged 18-39. The middle line 1014 represents individuals aged 40-64. The bottom line 1016 represents individuals aged 65 and older. The mean GRI value for individuals aged 65 or older remained in zone B and the mean GRI value for individuals aged 18-64 remained in zone C. As shown by the data captured in plot 1010, GRI values appear to be increasingly lower with age.

Figures 10C, 10D:
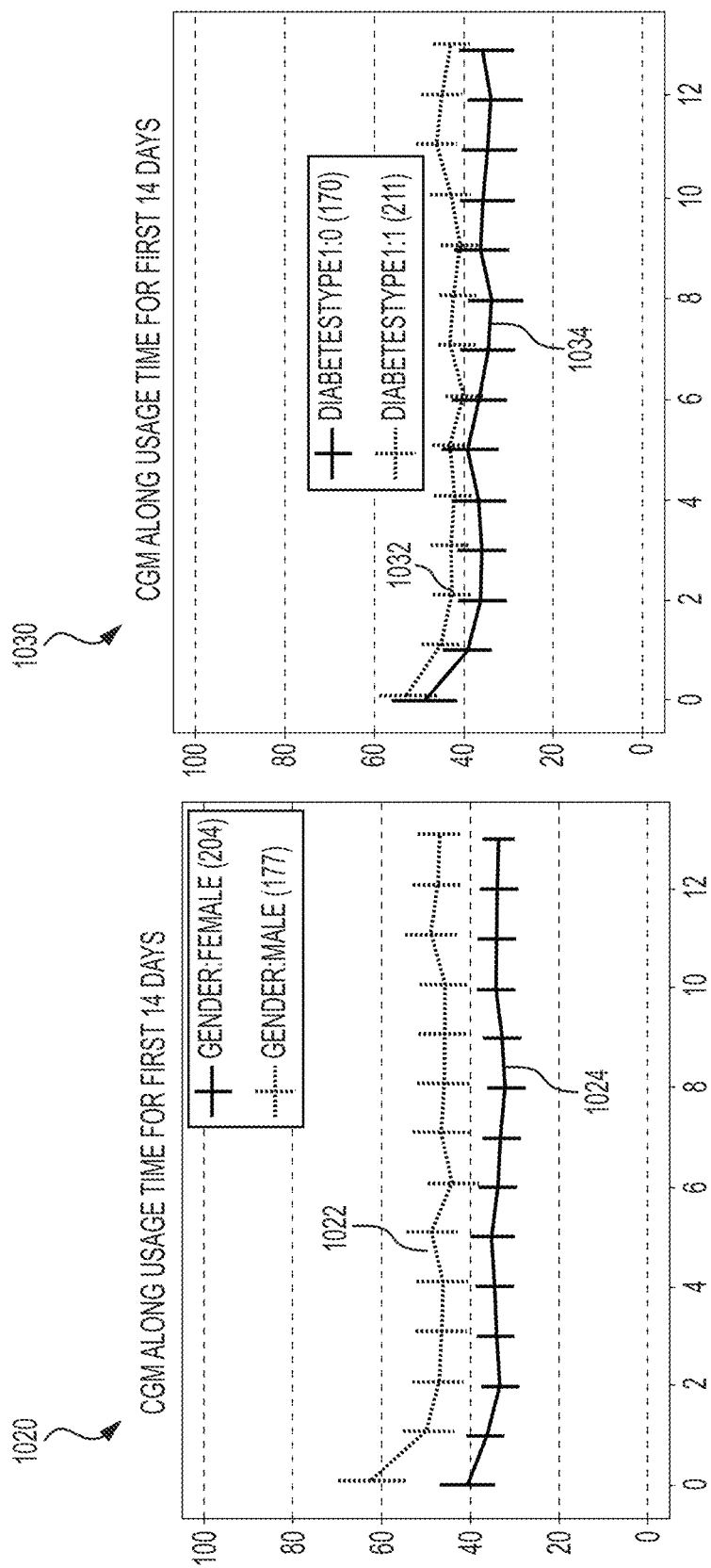

FIG. 10C depicts another example plot 1020 of mean GRI values over time for a group of individuals, according to one or more embodiments. Example plot 1020 displays two different groups of individuals, as grouped by gender. Upper line 1022 represents males and lower line 1024 represents females. As shown by the data captured in plot 1020, GRI values were lower for females than they were for males.

FIG. 10D depicts another example plot 1030 of mean GRI values over time for a group of individuals, according to one or more embodiments. Example plot 1030 displays two different groups of individuals, as grouped by type of diabetes. Line 1032 represents individuals with type 2 diabetes and line 1034 represents individuals with type 1 diabetes. As shown by the data captured in plot 1030, GRI values did not differ significantly by type of diabetes.

FIGS. 11A-11C are diagrams depicting relationships between precision, recall, specificity, and sensitivity, in accordance with one or more embodiments. In FIG. 11A, diagram 1102 shows that a population of positive and negative values may be classified and predicted as to their value.

FIG. 11B is a chart 1104 that depicts results of the classification shown in diagram 1102 of FIG. 11A. The results depicted in chart 1104 show that there were two negative values that were falsely predicted to be positive. FIG. 11C depicts equations 1106 that show how precision, recall, specificity, and sensitivity may be determined. In this example, recall may be the same as sensitivity, but precision is not the same as specificity.

Figure 12:
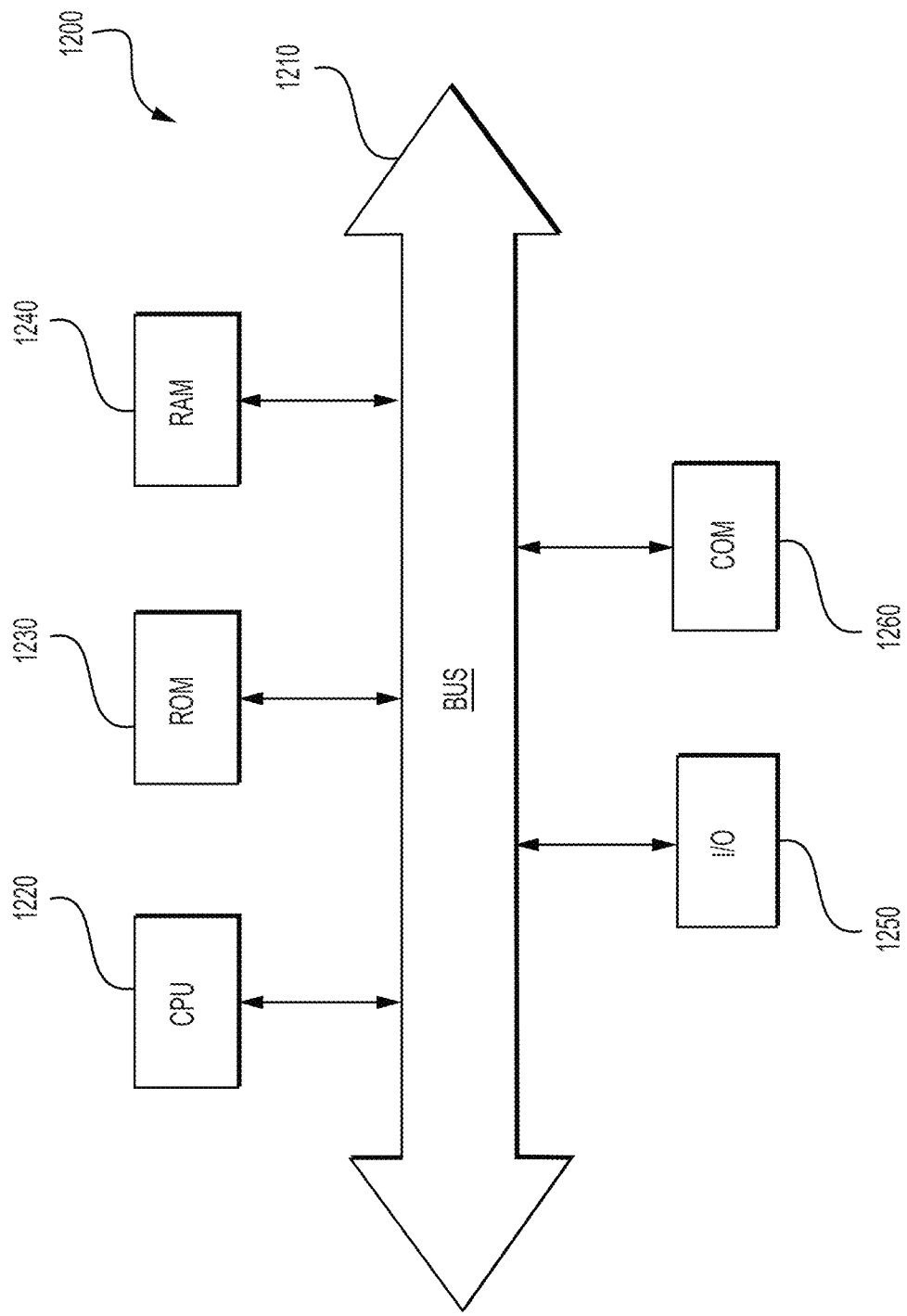
FIG. 12 is a simplified functional block diagram of a computer, in accordance with one or more embodiments.

FIG. 12 depicts a high-level functional block diagram of an exemplary computer device or system, in which embodiments of the present disclosure, or portions thereof, may be implemented, e.g., as computer-readable code. Additionally, each of the exemplary computer servers, databases, user interfaces, modules, and methods described above with respect to FIGS. 1-11C can be implemented in device 1200 using hardware, software, firmware, tangible computer readable media having instructions stored thereon, or a combination thereof and may be implemented in one or more computer systems or other processing systems. Hardware, software, or any combination of such may implement each of the exemplary systems, user interfaces, and methods described above with respect to FIGS. 1-11C.

If programmable logic is used, such logic may be executed on a commercially available processing platform or a special purpose device. One of ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, at least one processor device and a memory may be used to implement the above-described embodiments. A processor device may be a single processor or a plurality of processors, or combinations thereof. Processor devices may have one or more processor "cores."

Various embodiments of the present disclosure, as described above in the examples of FIGS. 1-11C, may be implemented using device 1200. After reading this description, it will become apparent to a person skilled in the relevant art how to implement embodiments of the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

A device 1200 for a computer or server or the like, for example, may include a data communication interface ports 1260 for packet data communication. The device also may include a central processing unit (CPU) 1220, in the form of one or more processors, for executing program instructions. The platform typically includes an internal communication bus 1210, program storage, and data storage for various data files to be processed and/or communicated by the platform such as ROM 1230 and RAM 1240 or the like. The hardware elements, operating systems, and programming languages of such equipment are conventional in nature, and it is presumed that those skilled in the art are adequately familiar therewith. The device 1200 also may include input and output ports 1250 to connect with input and output devices such as keyboards, mice, touchscreens, monitors, displays, etc., and communication ports 1260. Of course, the various server functions may be implemented in a distributed fashion on a number of similar platforms to distribute the processing load. Alternatively, the servers may be implemented by appropriate programming of one computer hardware platform.

It would be apparent to one of skill in the relevant art that the present disclosure, as described herein, can be implemented in many different examples of software, hardware, firmware, and/or the entities illustrated in the figures. Any actual software code with the specialized control of hardware to implement examples is not limiting of the detailed description. Thus, examples are described herein with the understanding that modifications and variations of the examples are possible, given the level of detail presented herein. Aspects of the described subject matter may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

It is to be understood that both the foregoing general description and the following detailed description are exemplary and explanatory only and are not restrictive of the disclosed examples, as claimed.

Other examples of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for predicting health and engagement levels for a user, the method comprising:
   sensing a user's glucose levels using a continuous glucose monitoring (CGM) device over a time period;
   receiving the user's glucose levels collected by the CGM device;
   receiving engagement data associated with the user, the engagement data collected by a computing device over the time period, wherein the engagement data is associated with the user's medication activity, diet activity, physical activity, laboratory results, education activity, and CGM device usage, wherein at least some of the engagement data is collected using one or more sensors associated with the user, the one or more sensors including at least one of a weight scale, a blood pressure monitor, an activity tracker, a heart rate monitor, a multi-purpose wearable device, the CGM device, and a ketone tracking device;
   determining a first glycemia risk index (GRI) value based on a first amount of time the user is hypoglycemic during the time period and a second amount of time the user is hyperglycemic during the time period;
   determining a time in range (TIR) value of the user's glucose level, wherein the determined TIR value is based on an amount of time the user's glucose level is within a threshold band over the time period, wherein the threshold band is determined based on lifestyle, habits, and medical test results of the user;
   inputting the user's glucose levels and the engagement data into a machine learning model;
   outputting, by the machine learning model and responsive to the user's glucose levels and the engagement data collected over the time period, one or more predictions for future glucose levels for the user including a prediction that a future GRI value is greater than or less than the first GRI value, wherein the one or more predictions for future glucose levels for the user further comprise a prediction that a future TIR value is one of within a threshold value of the determined TIR value, greater by more than threshold value, or less by more than the threshold value, wherein the one or more predictions for future glucose levels for the user further comprise a prediction that a future GRI value is in a higher GRI zone than the first GRI zone or in a lower GRI zone than the first GRI zone, wherein the one or more predictions for future glucose levels for the user further comprise a prediction that the future GRI value is in the first GRI zone, is in a second GRI zone higher than the first GRI zone, or is in a third GRI zone lower than the first GRI zone, wherein the one or more predictions for future glucose levels for the user further comprise a prediction that the future GRI value is greater than a threshold GRI value or less than the threshold GRI value;

outputting, by the machine learning model and responsive to the user's engagement data collected over the time period, one or more predictions for future engagement levels, wherein the one or more predictions for future engagement levels comprises a prediction that a future CGM device engagement level is above a threshold amount of CGM device engagement or below the threshold amount of CGM device engagement, wherein CGM device engagement includes a measure of CGM device use by the user, wherein the one or more predictions for future engagement levels further comprise a prediction that a future engagement level is a high engagement state or a low engagement state, and wherein the one or more predictions for future engagement levels further comprise a prediction that a future manual engagement level is a first manual engagement state or a second manual engagement state;

calculating, by the machine learning model, a timing and a dosing amount of basal insulin for the user at regular intervals;

administering, via an insulin pump, in response to an output of the machine learning model, at the timing of basal insulin at the regular intervals, the dosing amount of basal insulin to the user;

calculating, by the machine learning model, a timing and a dosing amount of bolus insulin for the user, the timing corresponding to mealtimes;

administering, via the insulin pump, in response to an output of the machine learning model, at the timing of bolus insulin at the mealtimes, the dosing amount of bolus insulin to the user;

providing, by the machine learning model, notifications to the user in response to calculating the timing and the dosing amount of basal insulin and the timing and the dosing amount of bolus insulin, wherein the notifications are provided based on the one or more predictions of future engagement levels; and synchronizing administration, via the insulin pump, in response to an output of the machine learning model, the dosing amount of basal insulin and the dosing amount of bolus insulin to the user.

2. The computer-implemented method of claim 1, further comprising:
wherein the one or more predictions for future glucose levels for the user further comprise a prediction that a future TIR value is greater than or less than the TIR value.

3. The computer-implemented method of claim 1, wherein the prediction of the low engagement state is indicative of the user engaging with one or more applications below a threshold amount.

4. The computer-implemented method of claim 1, further comprising:
deriving a set of features from the user's glucose levels and the engagement data; and providing the set of features as inputs to the machine learning model to determine the one or more predictions for future glucose levels for the user and the one or more predictions for future engagement levels.

5. The computer-implemented method of claim 1, wherein at least some of the engagement data is collected through user input from one or more applications on the computing device.

6. The computer-implemented method of claim 1, wherein the prediction of the high engagement state is indicative of the user engaging with one or more applications above a threshold amount.

7. A computer-implemented method for training a machine learning model for predicting health and engagement levels for a user, the method comprising:
receiving first glucose levels of the user collected by a continuous glucose monitoring (CGM) device over a first time period;
receiving second glucose levels of the user collected by the CGM device over a second time period subsequent to the first period of time;
receiving first engagement data associated with the user, the first engagement data collected by a computing device over the first time period;
receiving second engagement data associated with the user, the second engagement data collected by the computing device over the second time period, wherein the first engagement data and the second engagement data are associated with one or more of the user's medication intake, diet, physical activity, laboratory results, education activity, and CGM device usage, wherein at least some of the first engagement data and second engagement data is collected using one or more sensors associated with the user, the one or more sensors including at least one of a weight scale, a blood pressure monitor, an activity tracker, a heart rate monitor, a multi-purpose wearable device, a blood glucose monitor, and a ketone tracking device;
deriving one or more sets of features from the first glucose levels, the second glucose levels, the first engagement data, and second glucose levels, wherein the training data comprises the derived one or more sets of features;
extracting one or more sub features from each of the one or more sets of features;
training a machine learning model to generate a trained machine learning model based on a machine learning algorithm and using training data comprising the one or more sub features, the first glucose levels, the second glucose levels, the first engagement data, and the second engagement data;
determining one or more patterns in the training data, wherein determining one or more patterns in the training data comprises determining a relationship between the first glucose levels and the second glucose levels, and determining a relationship between the first engagement data and the second engagement data;
receiving third glucose levels for the user collected by the CGM device over a third time period subsequent to the second time period;
receiving third engagement data associated with the user, the third engagement data collected by the computing device over the third time period, wherein the third engagement data are associated with the user's medication intake, diet, physical activity, laboratory results, and education activity, wherein at least some of the third engagement data is collected using one or more sensors associated with the user, the one or more sensors including at least one of a weight scale, a blood pressure monitor, an activity tracker, a heart rate monitor, a multi-purpose wearable device, a blood glucose monitor, and a ketone tracking device;

receiving, from the trained machine learning model and responsive to the third glucose levels and the third engagement data collected over the third time period, one or more predictions for future glucose levels for the user;

receiving, from the trained machine learning model and responsive to the user's third engagement data collected over the third time period, one or more predictions for future engagement levels;

calculating, by the machine learning model, a timing and a dosing amount of basal insulin for the user at regular intervals;

administering, via an insulin pump, in response to an output of the machine learning model, at the timing of basal insulin at the regular intervals, the dosing amount of basal insulin to the user;

calculating, by the machine learning model, a timing and a dosing amount of bolus insulin for the user, the timing corresponding to mealtimes;

administering, via the insulin pump, in response to an output of the machine learning model, at the timing of bolus insulin at the mealtimes, the dosing amount of bolus insulin to the user;

providing, by the machine learning model, notifications to the user in response to calculating the timing and the dosing amount of basal insulin and the timing and the dosing amount of bolus insulin, wherein the notifications are provided based on the one or more predictions of future engagement levels; and synchronizing administration, via the insulin pump, in response to an output of the machine learning model, the dosing amount of basal insulin and the dosing amount of bolus insulin to the user.

8. The computer-implemented method of claim 7, wherein training the machine learning model further comprises:
updating one of weights, layers, biases, or synapses of the machine learning model based on the determined patterns to generate the trained machine learning model.

9. The computer-implemented method of claim 7, wherein the first glucose levels and the second glucose levels have a different amount of glucose measurements.

10. The computer-implemented method of claim 7, wherein at least some of the first engagement data, the second engagement data, and third engagement data is collected through user input from one or more applications on the computing device.

11. A system for predicting future glucose levels and engagement, the system comprising:
a memory having processor-readable instructions stored therein; and
a processor configured to access the memory and execute the processor-readable instructions, which, when executed by the processor configures the processor to perform a method, the method comprising:
sensing a user's glucose levels using a continuous glucose monitoring (CGM) device over a time period;
receiving the user's glucose levels collected by the CGM device;
receiving engagement data associated with the user, the engagement data collected by a computing device over the time period, wherein the engagement data is associated with the user's medication activity, diet activity, physical activity, laboratory results, education activity, and CGM device usage, wherein at least some of the engagement data is collected using one or more sensors associated with the user, the one or more sensors including at least one of a weight scale, a blood pressure monitor, an activity tracker, a heart rate monitor, a multi-purpose wearable device, the CGM device, and a ketone tracking device;

determining a first glycemia risk index (GRI) value based on a first amount of time the user is hypoglycemic during the time period and a second amount of time the user is hyperglycemic during the time period;

determining a time in range (TIR) value of the user's glucose level, wherein the determined TIR value is based on an amount of time the user's glucose level is within a threshold band over the time period, wherein the threshold band is determined based on lifestyle, habits, and medical test results of the user;

inputting the user's glucose levels and the engagement data into a machine learning model;

outputting, by the machine learning model and responsive to the user's glucose levels and the engagement data collected over the time period, one or more predictions for future glucose levels for the user including a prediction that a future GRI value is greater than or less than the first GRI value, wherein the one or more predictions for future glucose levels for the user further comprise a prediction that a future TIR value is one of within a threshold value of the determined TIR value, greater by more than threshold value, or less by more than the threshold value, wherein the one or more predictions for future glucose levels for the user further comprise a prediction that a future GRI value is in a higher GRI zone than the first GRI zone or in a lower GRI zone than the first GRI zone, wherein the one or more predictions for future glucose levels for the user further comprise a prediction that the future GRI value is in the first GRI zone, is in a second GRI zone higher than the first GRI zone, or is in a third GRI zone lower than the first GRI zone, wherein the one or more predictions for future glucose levels for the user further comprise a prediction that the future GRI value is greater than a threshold GRI value or less than the threshold GRI value;

outputting, by the machine learning model and responsive to the user's engagement data collected over the time period, one or more predictions for future engagement levels, wherein the one or more predictions for future engagement levels comprises a prediction that a future CGM device engagement level is above a threshold amount of CGM device engagement or below the threshold amount of CGM device engagement, wherein CGM device engagement includes a measure of CGM device use by the user, wherein the one or more predictions for future engagement levels further comprise a prediction that a future engagement level is a high engagement state or a low engagement state, and wherein the one or more predictions for future engagement levels further comprise a prediction that a future manual engagement level is a first manual engagement state or a second manual engagement state;

calculating, by the machine learning model, a timing and a dosing amount of basal insulin for the user at regular intervals;

administering, via an insulin pump, in response to an output of the machine learning model, at the timing of basal insulin at the regular intervals, the dosing amount of basal insulin to the user;

calculating, by the machine learning model, a timing and a dosing amount of bolus insulin for the user, the timing corresponding to mealtimes;

administering, via the insulin pump, in response to an output of the machine learning model, at the timing of bolus insulin at the mealtimes, the dosing amount of bolus insulin to the user;

providing, by the machine learning model, notifications to the user in response to calculating the timing and the dosing amount of basal insulin and the timing and the dosing amount of bolus insulin, wherein the notifications are provided based on the one or more predictions of future engagement levels; and synchronizing administration, via the insulin pump, in response to an output of the machine learning model, the dosing amount of basal insulin and the dosing amount of bolus insulin to the user.

12. The system of claim 11, wherein the one or more predictions for future glucose levels for the user further comprise a prediction that a future TIR value is greater than or less than the TIR value.

13. The system of claim 12, wherein the prediction of the low engagement state is indicative of the user engaging with one or more applications below a threshold amount.

14. The system of claim 11, further comprising:

deriving a set of features from the user's glucose levels and the engagement data; and providing the set of features as inputs to the machine learning model to determine the one or more predictions for future glucose levels for the user and the one or more predictions for future engagement levels.

15. The system of claim 11, wherein at least some of the engagement data is collected through user input from one or more applications on the computing device.

16. The system of claim 11, wherein the classification of the high engagement state is indicative of the user engaging with one or more applications above a threshold amount.

17. The system of claim 11, wherein the classification of the low engagement state is indicative of the user engaging with one or more applications below a threshold amount.

* * * * *